US010641779B2

(12) United States Patent
Steyaert et al.

(10) Patent No.: US 10,641,779 B2
(45) Date of Patent: May 5, 2020

(54) METHODS TO SELECT FOR AGENTS THAT STABILIZE PROTEIN COMPLEXES

(71) Applicants: VIB VZW, Ghent (BE); Vrije Universiteit Brussel, Brussels (BE)

(72) Inventors: Jan Steyaert, Beersel (BE); Alexandre Wohlkönig, Brussels (BE); Sarah Triest, Tielt-Winge (BE)

(73) Assignees: VIB VZW, Ghent (BE); Vrije Universiteit Brussel, Brussels (BE)

( * ) Notice: Subject to any disclaimer, the term of this patent is extended or adjusted under 35 U.S.C. 154(b) by 327 days.

(21) Appl. No.: 15/327,992

(22) PCT Filed: Jul. 17, 2015

(86) PCT No.: PCT/EP2015/066405
§ 371 (c)(1),
(2) Date: Jan. 20, 2017

(87) PCT Pub. No.: WO2016/012363
PCT Pub. Date: Jan. 28, 2016

(65) Prior Publication Data

US 2017/0160285 A1 Jun. 8, 2017

(30) Foreign Application Priority Data

Jul. 22, 2014 (EP) .................................... 14178012

(51) Int. Cl.
*G01N 33/68* (2006.01)
*G01N 33/49* (2006.01)

(52) U.S. Cl.
CPC ..... *G01N 33/6845* (2013.01); *G01N 33/6854* (2013.01); *G01N 33/6857* (2013.01); *G01N 33/492* (2013.01); *G01N 33/4915* (2013.01)

(58) Field of Classification Search
CPC ........... G01N 33/6845; G01N 33/6854; G01N 33/6857; G01N 33/4915; G01N 33/492
See application file for complete search history.

(56) References Cited

U.S. PATENT DOCUMENTS 9,453,065 B2 9/2016 Steyaert et al.

FOREIGN PATENT DOCUMENTS

WO 9404678 A1 3/1994
WO 9425591 A1 11/1994
(Continued)

OTHER PUBLICATIONS

Pardon et al. A general protocol for the generation of Nanobodies for structural biology. Nature Protocols 9 (3): 671-693 (Feb. 2014).*
(Continued)

*Primary Examiner* — Gailene Gabel
(74) *Attorney, Agent, or Firm* — Patent Law Works LLP

(57) ABSTRACT

The application relates to the field of structural biology. More specifically, the disclosure relates to methods for the identification and characterization of biomolecular tools allowing the selective recognition and/or stabilization of distinct conformational states of protein complexes, including transient protein-protein interactions and protein-nucleic acid complexes. Such tools can then be used for purification purposes, crystallization and structure determination of these stabilized protein complexes, for drug discovery, as research tools, as well as for diagnosis and treatment of diseases.

18 Claims, 21 Drawing Sheets

Specification includes a Sequence Listing.

Fluorescent label 1
Fluorescent label 2
Q1
Q2
Q3
Q4
Fluorescence protein A
Fluorescence protein B

(56) References Cited

FOREIGN PATENT DOCUMENTS

| | | | | |
|---|---|---|---|---|
| WO | 9504079 A1 | | 2/1995 | |
| WO | 9634103 A1 | | 10/1996 | |
| WO | 9749805 A2 | | 12/1997 | |
| WO | 9937681 A2 | | 7/1999 | |
| WO | 0040968 A1 | | 7/2000 | |
| WO | 0043507 A1 | | 7/2000 | |
| WO | 0065057 A1 | | 11/2000 | |
| WO | 0121817 A1 | | 3/2001 | |
| WO | 0140310 A2 | | 6/2001 | |
| WO | 0144301 A1 | | 6/2001 | |
| WO | 03035694 A2 | | 5/2003 | |
| WO | 03054016 A2 | | 7/2003 | |
| WO | 03055527 A2 | | 7/2003 | |
| WO | 2004041862 A2 | | 5/2004 | |
| WO | 2004041863 A2 | | 5/2004 | |
| WO | 2004041865 A2 | | 5/2004 | |
| WO | 2004041867 A2 | | 5/2004 | |
| WO | 2004062551 A2 | | 7/2004 | |
| WO | 2005044858 A1 | | 5/2005 | |
| WO | 2006079372 A1 | | 8/2006 | |
| WO | 2006122786 A2 | | 11/2006 | |
| WO | 2006122787 A1 | | 11/2006 | |
| WO | 2006122825 A2 | | 11/2006 | |
| WO | 2008020079 A1 | | 2/2008 | |
| WO | 2008101985 A2 | | 8/2008 | |
| WO | 2008142164 A2 | | 11/2008 | |
| WO | 2010066740 A1 | | 6/2010 | |
| WO | 2010070145 A2 | | 6/2010 | |
| WO | WO 2011/042398 | * | 4/2011 | ............ C07K 16/28 |
| WO | 2011083141 A1 | | 7/2011 | |
| WO | 2016012363 A1 | | 1/2016 | |

OTHER PUBLICATIONS

Ring et al. Adrenaline-activated structure of B2-adrenoreceptor stabilized by an engineered antibody. Nature 502: 575-580 (Oct. 24, 2013).*

De Meyer et al., Nanobody-based products as research and diagnostic tools, Trends in Biotechnology May 2014, vol. 32, No. 5 , 2014.

Guilliams et al., Nanobodies Raised against Monomeric a-Synuclein Distinguish between Fibrils at Different Maturation Stages, Nanobodies and a-Synuclein Fibril Formation, Elsevier Ltd., JMB 2013.

PCT International Search Report and Written Opinion, PCT/EP2015/066405, dated Sep. 22, 2015.

PCT International Search Report, PCT/EP2015/PCT/EP2015/066405, dated Sep. 22, 2015.

Khamrui et al., The structure of the D3 domain of Plasmodium falciparum myosin tail interacting protein MTIP in complex with a nanobody, Molecular & Biochemical Parasitology 190 (2013) 87-91, 2013.

Kruse et al., Activation and Allosteric Modulation of a Muscarinic Acetylcholine Receptor, doi:10.1038/nature12735, 2013.

Mujic-Delic et al., GPCR-targeting nanobodies: attractive research tools, diagnostics, and therapeutics, cell press, Amsterdam Institute for Molecules, 2014.

Paalanen et al., the development of activating and inhibiting camelid VHH domains against human protein kinase C epsilon, European Journal of Pharmaceutical Sciences 42 (2011) 332-339, 2011.

Pardon et al., A General Protocol for the Generation of Nanobodies for Structural Biology, nature protocols, (2014).

Ring et al., Adrenaline-activated structure of B2-adrenoceptor stabilized by an engineered nanobody, doi:10.1038/nature12572, 2013.

Staus et al., Regulation of B2-Adrenergic Recepto Function by Conformationally Selective Single-Domain Intrabodies, Mol Pharmacol 85:472-481, Mar. 2014.

* cited by examiner

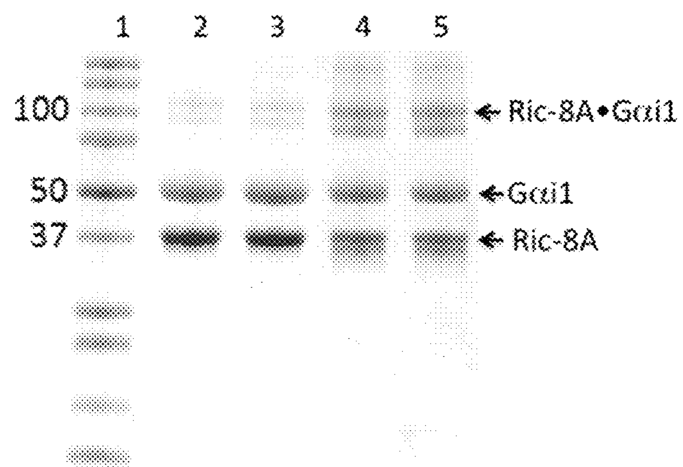
FIG. 3
Round 1
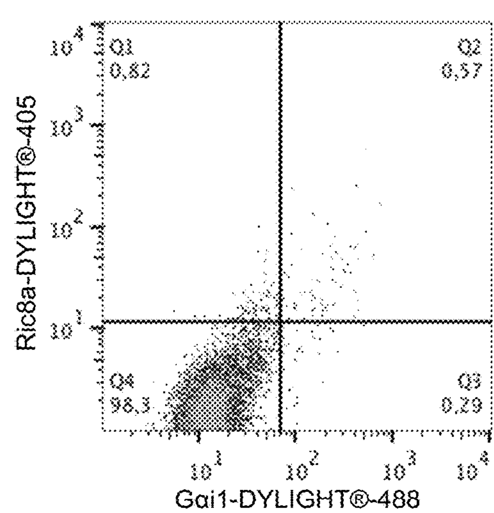
Round 2
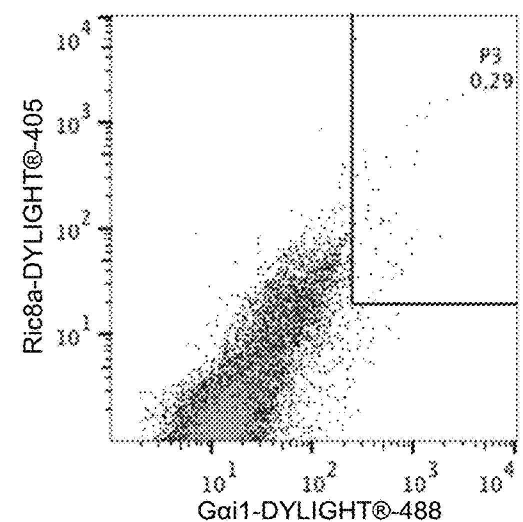
Round 3
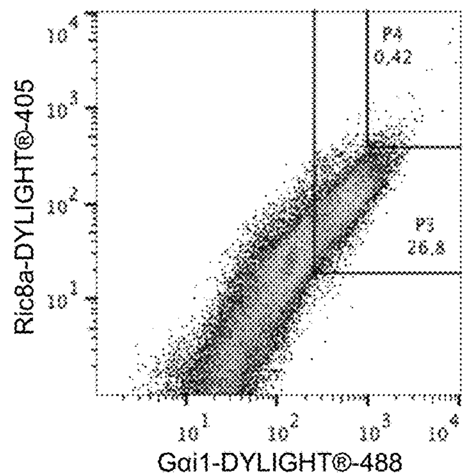
FIG. 4

```
                        20                  40                  60                  80                  100                 120
                        |                   |                   |                   |                   |                   |
CA9312  QVQLVESGGGLVQAGGSKRLSCAASGRPFSNSAMGWFRQAPGKEREFVAAISWSGGNTYYADSVKGRFTISRDNAKNAVYLRMNSLEPEDTAVYYCAGDRQPYVYDLPTAQYQYDYWGQGTQVTVSSGSEQKLISEEDL 139
CA9402  QVQLVESGGGLVQAGGSLRLSCAASGRTFSNYAMGWFRQAPGKEREFVAAISWSGGKTLYAESVKGRFTISRDNAKNTVYLQMNSLKPEDTAVYYCAATPADLTVVAGPPRIEMNYWGQGTQVTVSSGSEQKLISEEDL 139
CA8418  QVQLVESGGGLVQAGGSLRLSCAASGRTFSNYAMGWFRQAPGKEREFVAALTWSGGNTVYRDSVKGRFIITRDNAKNAVYLQMNSLKPEDTAVYYCASDRRPYRYNIGTAEGEYNYWGQGTQVTVSSGSEQKLISEEDL 139
CA8315  QVQLVESGGGLVQAGGSLRLSCAASGRTFSNYAMGWFRQTPGKEREFVAAITWSGGATYYADSVKGRFIISRDNTKNTVYLQMNSLKPEDTAVYYCAADRKPYSY-YPS---DFGSWGQGTQVTVSSGSEQKLISEEDL 135
CA8421  QVQLVESGGGLVQAGGSLRLSCAASGRTFSNYAMGWFRQAPGKEREFVAHITWTGGITYYSDSVKGRFIISRDNAKNTVNLQMNSLKAEDTAVYYCAADRVPYRFGVPSIN-EYDYWGQGTQVTVSSGSEQKLISEEDL 138
CA8403  QVQLVESGGGLVQAGGSLRLSCAASTRTFSNYVMGWFRQAPGKEREFVSAITSSGRGTSYADSVKGRFTISRDNAKNTVFLQMNSLKPEDTAVYYCAATAADYV--LRSRPSVYSYWGQGTQVTVSSGSEQKLISEEDL 137
CA8411  QVQLVESGGGLVQAGGSLRLSCAASARTFSRYGAGWFRQAPGKEREFVGAITWGGGRTKYADSVKGRFTISRDNSKNTVYLQMNSLKSEDTAVYYCASSSIEF----GPLEDTYDYWGQGTQVTVSSGSEQKLISEEDL 135
CA8314  QVQLVESGGGLVQAGDSLRLSCTASERAFSRYAMGWFRQAPGKERELVAAVSWAGGTTYYGDSVKGRFTISRDNAKITVYLQMNSLKPEDTAVYYCAAEAREFSVGSYYAT-EYDYWGQGTQVTVSSGSEQKLISEEDL 138
CA8318  QVQLVESGGGRVQAGDSLRLSCAASGRTFSPYAMGWFRQAPGKEREFVATINWSGDYTYYTDSVKGRFTTSRDNAKNTLYLEMNSLNAEDTAVYYCVARVGSPS----SSDRAYQYWGQGTQVTVSSGSEQKLISEEDL 135
CA8405  QVQLVESGGGLVQDGGSLRLSCTASGRTFSNNAMGWFRQEPGREREFVAAIRWNG--IANYADSVKGRFTISGDNAKNTVYLQMNSLKPDDTAVYYCAAAIRDGHNYYASDMRRYDYWGQGTQVTVSSGSEQKLISEEDL 138
CA8316  QLQLVESGGGLVQAGGSLRLSCAASGDTFSRYVMGWFRQAPGKERTFVVGISGGGGITRYADSVKGRFTISRDNAENTLYLEMNTLNPEDTAVYYCAATPADSAF--MRNLRVYDYWGQGTQVTVSSGSEQKLISEEDL 137
CA8319  QVQLVESGGGLVQAGGSLRLSCEASGRTSSSYVMGWFRRVSGKEREFVAAINPTGSSTYYADSVKGRFTISRDNSKNTVYVQMNGLKPEDTAVYYCAATRRDF-YIIRNSRPQFDYWGQGTQVTVSSGSEQKLISEEDL 138
CA8322  QVQLVESEGGLVQPGGSLRLSCAASGFTFKYYYMNWVRQAPGKGLEWVSRINQLGG-TSYGDSVKGRFTISRDNAKNTLYLQMNSLVPEDTAVYYCARCPAGAA------CKVEYDYRGQGTQVTVSSGSEQKLISEEDL 133
CA8419  QVQLVESGGGLVQPGGSLXLSCAASGFTFSRFVMNWARQAPGKGLEWVSTINSDGDVTSYADSVKGRFTISRDNAKNTLYLQMNSLKPEDTAVYYCGK---GWF------LNRRDESRGQGTQVTVSSGSEQKLISEEDL 131
CA8424  QVQLVESGGDLVQAGGSLXLSCAASGGIFIINNMGWYRQTPGNQRELVAEITRAGN-SNYADSVKGRFTISRDNAKNTVYLQMNRLKPEDTAVYYCNFNVRYYG-----------EYWGQGTQVTVSSGSEQKLISEEDL 128
```

FIG. 5

Round 1
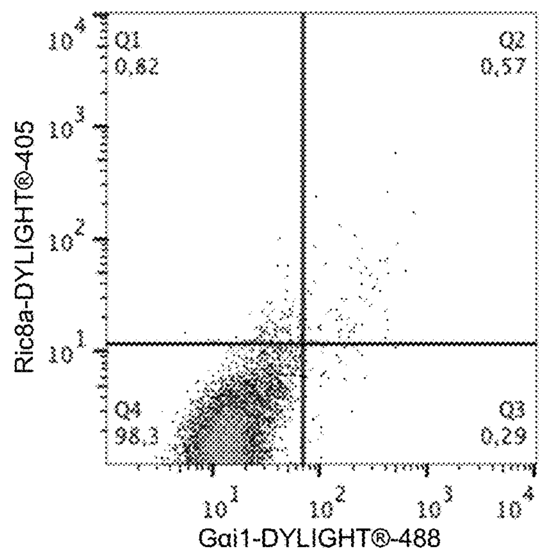
Round 2
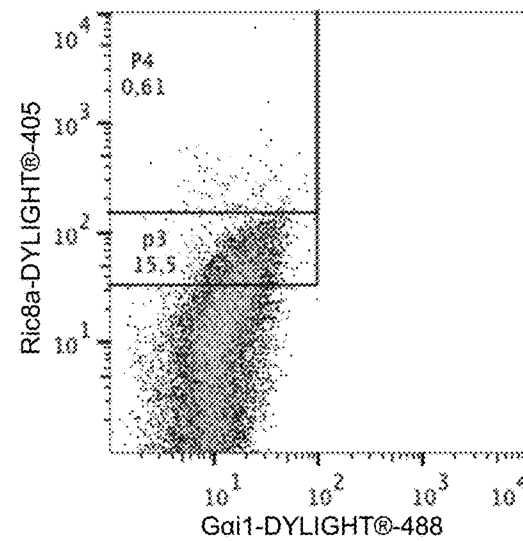
FIG. 6

Ric8A/ Type 1
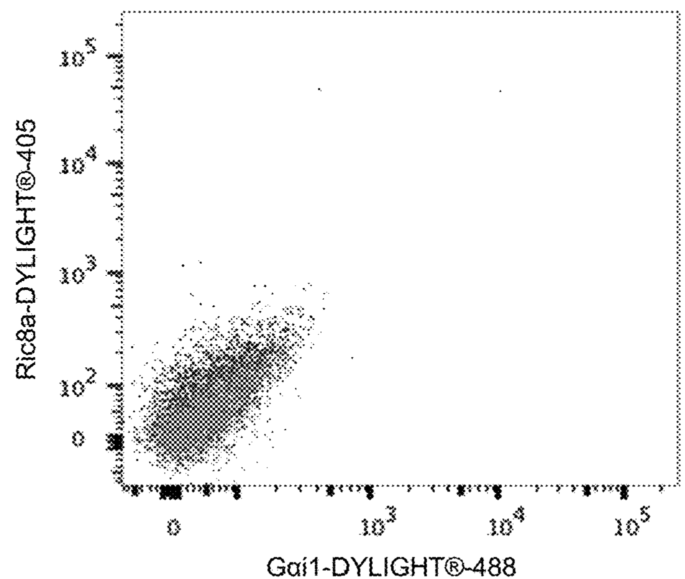
Gαi1 (GDP)/ Type 1
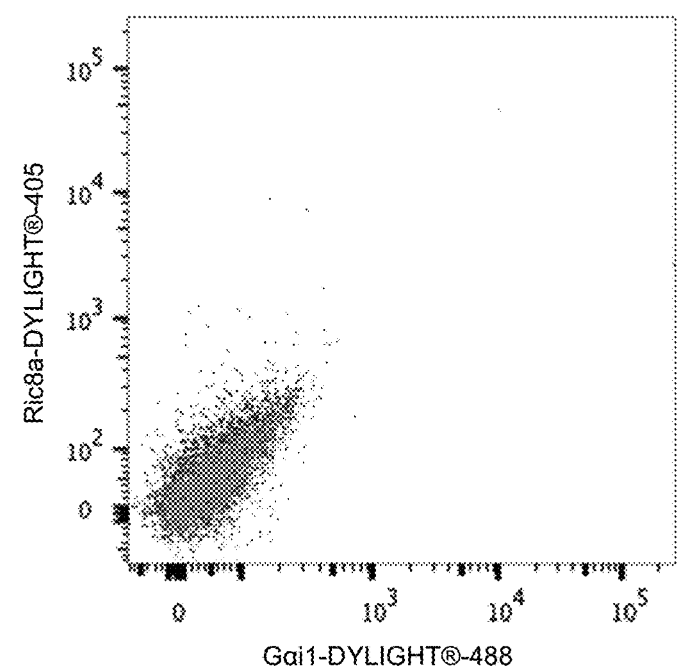
FIG. 8A

Ric8A/ Gαi1/ Type 1
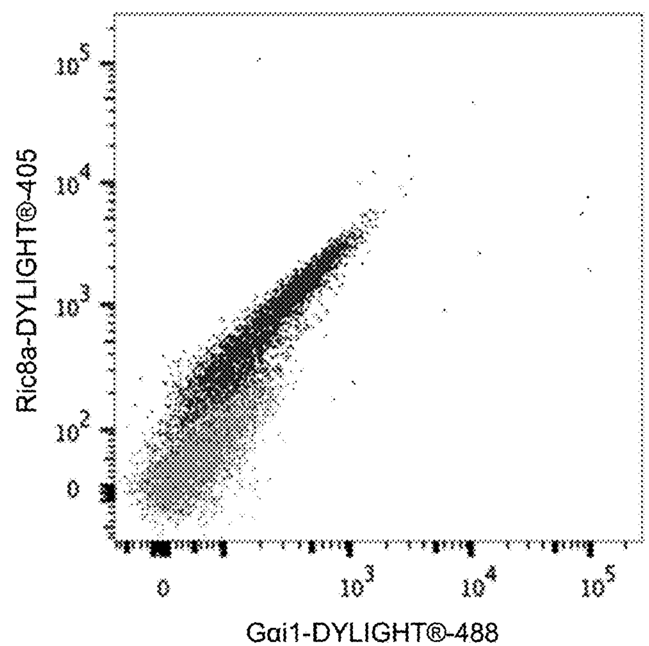
Ric8A /Type 2
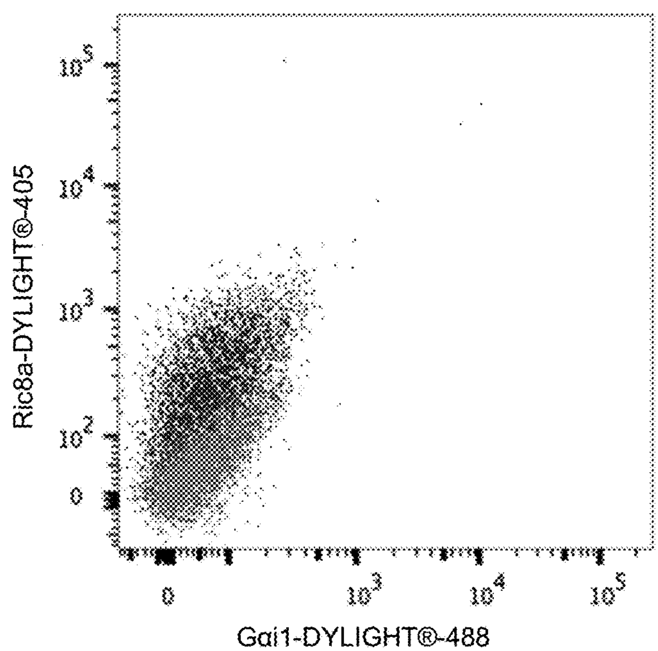
FIG. 8B

Gαi1 (GDP)/ Type 2
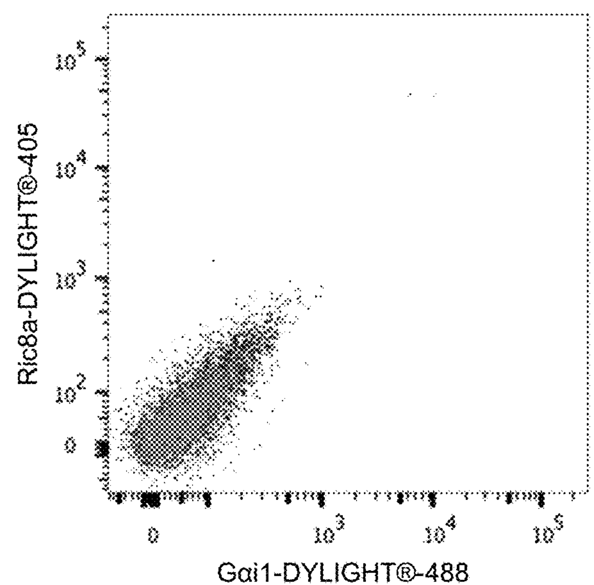
Ric8A/ Gαi1/ Type 2
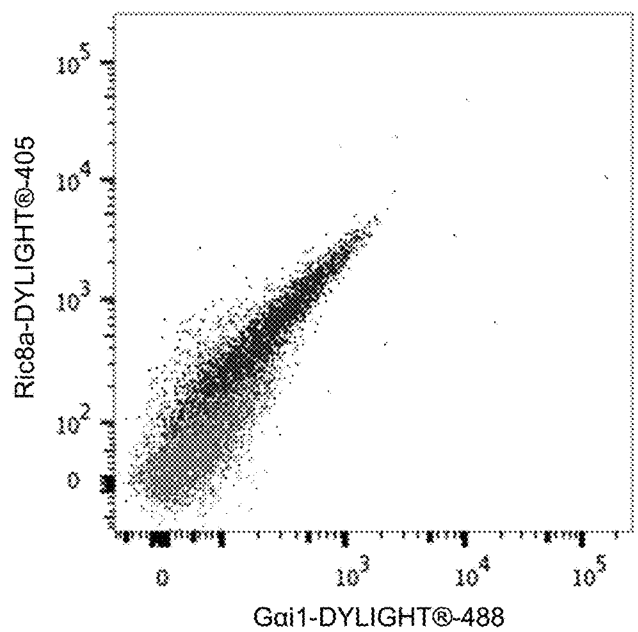
FIG. 8C

Ric8A/ Type 3
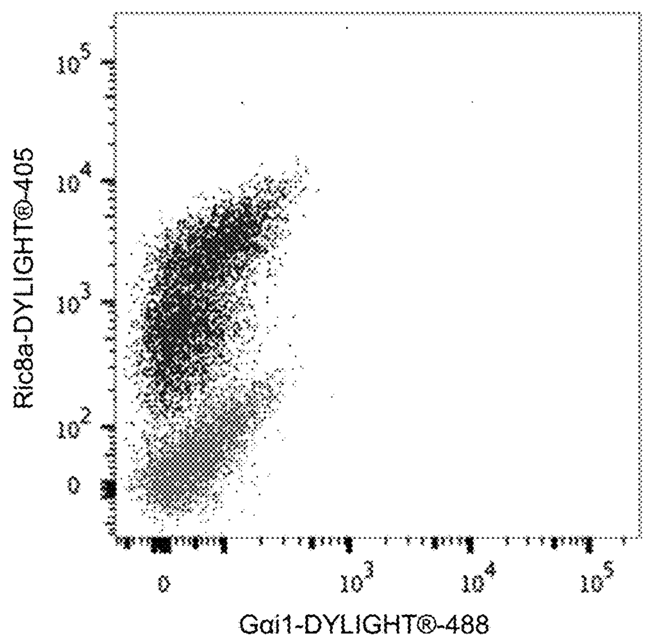
Gαi1 (GDP)/ Type 3
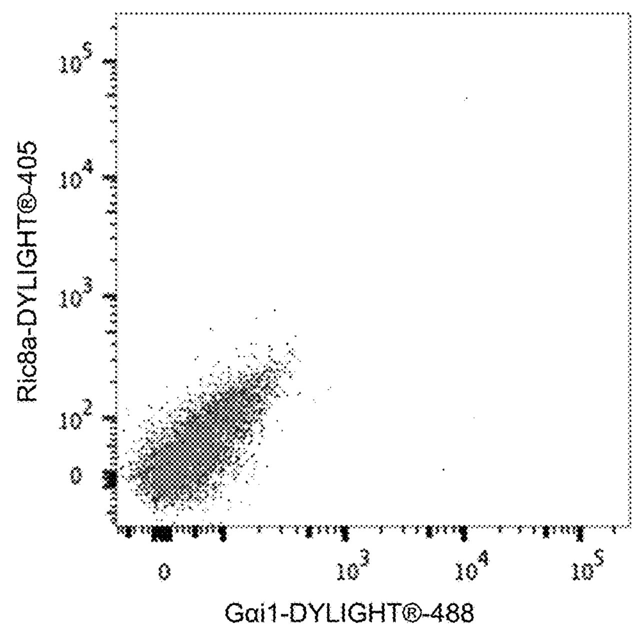
FIG. 8D

Ric8A/ Gαi1/ Type 3

Round 1
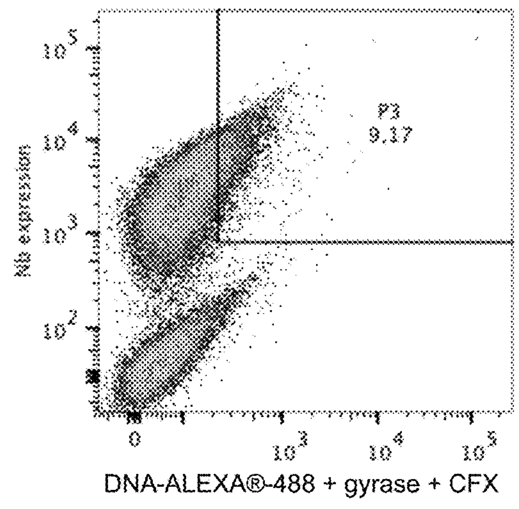
Round 2
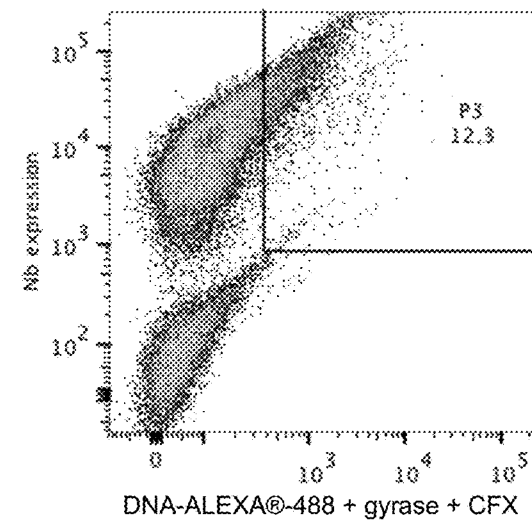
Round 3a
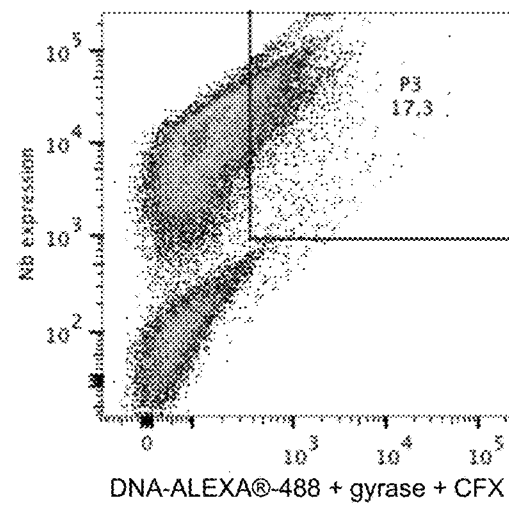
Round 4a
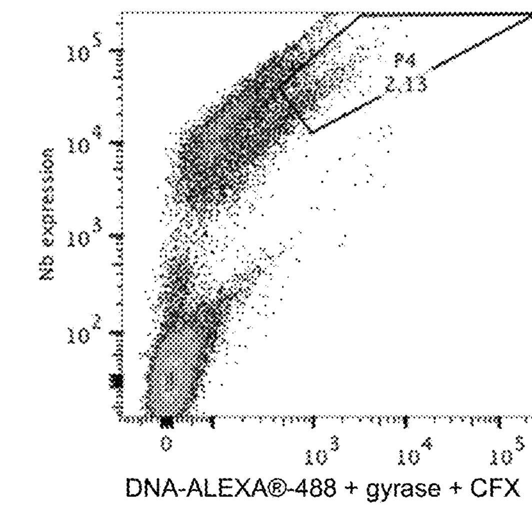
FIG. 11A Round 3b
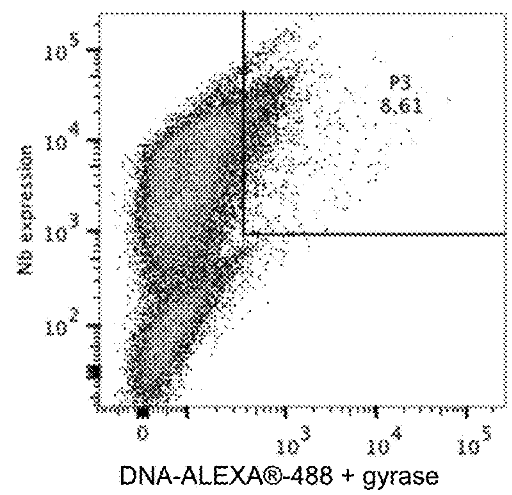
Round 4b
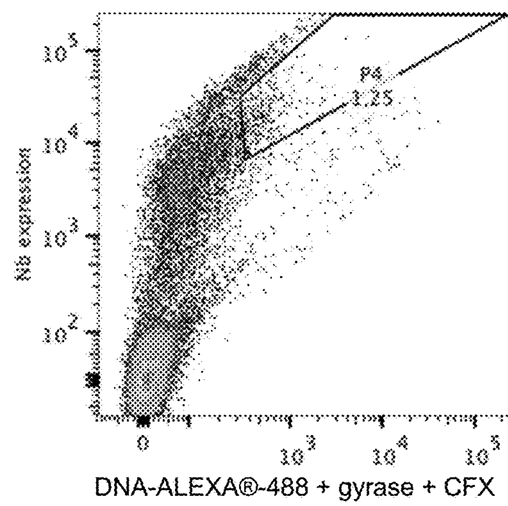
FIG. 11B

```
                          20                  40                  60                  80                  100                 120                 140
                          |                   |                   |                   |                   |                   |                   |
CA9304 QVQLVESGGGLVQAGGSLRLSCVASGLTLTNYVMGWFRQAPGKEREFVAAISRSGSGTDYVDSVKGRFTISRDNAKNTVYLQMNSLKPEDTAVYYCGADSAGWF--RIRQVPADYDYWGQGTQVTVSSGSEQKLISEEDL 138
CA9305 QVQLVESGGGLVQAGGSLRLSXAASGRSFDIHAMGWFRQAPGKEREFVAAISWNSGNTEYADVVKGRFTISRDNAKDTVYLQMNGLKPEDTAVYYCARGAFSF----ATTVQSDYNYWGQGTQVTVSSGSEQKLISEEDL 136
CA9302 QVQLVESGGGLVQPGGSLRLSCTASEGTFSVYNLAWFRQAPGKERELVASINWSGSVTYYTDSVKGRFTVSRDNAKNTVYLQMNSLKPEDTAVYYCAA-ALRPN--SVQ-----YKYWGQGTQVTVSSGSEQKLISEEDL 132
CA9303 QVQLVESGGGLVQAGGSLRLSCAASGRTFSNYRMGWFRQPPGKEREFVARISPNGGSTYYTDSMRGRFIISRDNVKNTVYLQMNSLKHEDTAVYYCAA-TPGYT--SASKVPSDYAYWGQGTQVTVSSGSEQKLISEEDL 137
CA9307 QVQLVESGGGLVQAGGSLRLSCAASGRTFSSDYMAWIRQPPGKESEFVAVIARSNAGTFYADSVKGRFTISRDNAKNTVYLQMNSLNREDTAVYYCTADHA--L--RLSSRLTDYDYWGQGTQVTVSSGSEQKLISEEDL 136
CA9309 QVQLVESGGGVVQAGGSLRLSCAASGRTLGSYDVGWFRQAPGKEREFLSISRQSGASIYCADSVKGRFTVSRDNAKNLVYLQMNSLKPEDTAVYYCAADPSRWYFCSSDSNPNTFDSWGQGTQVTVSSGSEQKLISEEDL 140
```

FIG. 12

Round 1
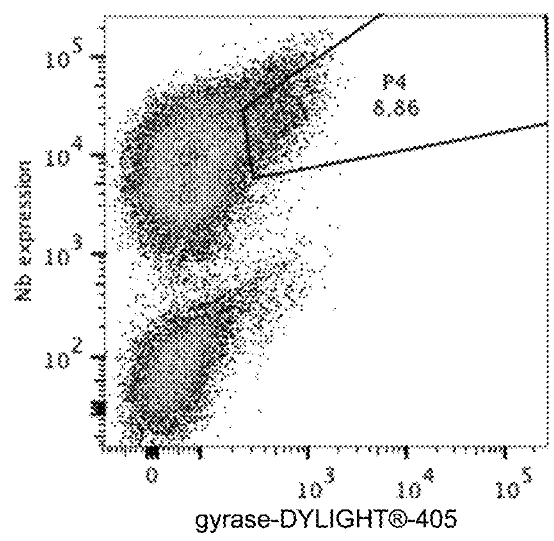
Round 2
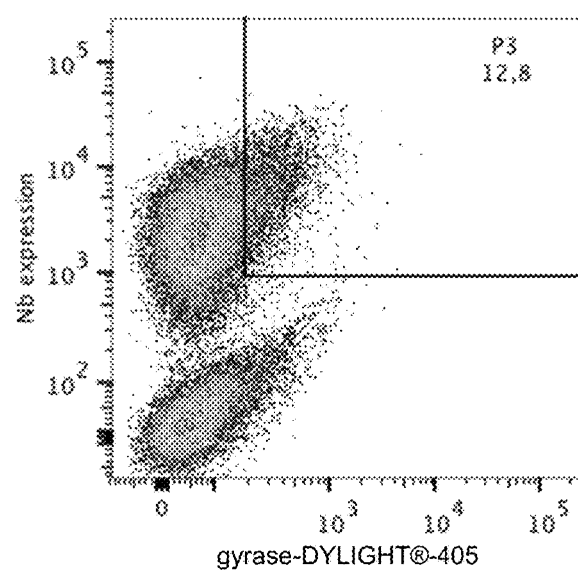
FIG. 13

```
                            20                  40                  60                  80                  100                 120                 140
CA9304 QVQLVESGGGLVQAGGSLRLSCVASGLTLTNYVMGWFRQAPGKEREFVAAISRSGSGTDYVDSVKGRFTISRDNAKNTVYLQMNSLKPEDTAVYYCGADSAGWFRIRQVPA--DYDYWGQGTQVTVSSGSEQKLISEEDL 138
CA9305 QVQLVESGGGLVQAGGSLRLSXAASGRSFDIHAMGWFRQAPGKEREFVAAISWNSGNTEYADVVKGRFTISRDNAKDTVYLQMNGLKPEDTAVYYCARGAFSF--ATTVQS--DYNYWGQGTQVTVSSGSEQKLISEEDL 136
CA9308 QVQLVESGGGLAQAGASLRLSCVASGRTFESYPMGWFRQAPGKEREFVGAISWNGGVIDYADSVKGRFTISRDNAKNTVYLQMNNLKPEDTAIYYCATKTRG--GDWRSGK--NWNYWGQGTQVTVSSGSEQKLISEEDL 136
CA9306 QVQLVESGGGLVQAGGSLRLSCAASGHASSTYTMGWFRQAPGKEREFVSGINWSDDSTSYAESVKGRFTISRDGAKNTVYLQMNSLKPEDTAVYYCALQ-YGWRWSWDDGSARDMRYWGKGTQVTVSSGSEQKLISEEDL 139
CA9302 QVQLVESGGGLVQPGGSLRLSCTASEGTFSVYNLAWFRQAPGKERELVASINWSGSVTYYTDSVKGRFTVSRDNAKNTVYLQMNSLKPEDTAVYYCAA-ALRPNSVQ-------YKYWGQGTQVTVSSGSEQKLISEEDL 132
CA9303 QVQLVESGGGLVQAGGSLRLSCAASGRTFSNYRMGWFRQPPGKEREFVARISPNGGSTYYTDSMRGRFIISRDNVKNTVYLQMNSLKHEDTAVYYCAA-TPGYTSASKVPS--DYAYWGQGTQVTVSSGSEQKLISEEDL 137
CA9310 QVQLVESGGGLVQAGGSLRLSCAAAGRTFSTYARGWFRQAPGKEREFVAILT-RGSDAYYADSVRGRFTISRDSATNTVYLQMTSLKPEDTAVYYCAAST-----GYGTNSRYDYDYWGQGTQVTVSSRSEQKLISEEDL 134
CA9309 QVQLVESGGGVVQAGGSLRLSCAASGRTLGSYDVGWFRQAPGKEREFLSISRQSGASIYCADSVKGRFTVSRDNAKNLVYLQMNSLKPEDTAVYYCAADPSRWYFCSSDSNPNTFDSWGQGTQVTVSSGSEQKLISEEDL 140
```

FIG. 14

METHODS TO SELECT FOR AGENTS THAT STABILIZE PROTEIN COMPLEXES

CROSS-REFERENCE TO RELATED APPLICATIONS

This application is a national phase entry under 35 U.S.C. § 371 of International Patent Application PCT/EP2015/066405, filed Jul. 17, 2015, designating the United States of America and published in English as International Patent Publication WO 2016/012363 A1 on Jan. 28, 2016, which claims the benefit under Article 8 of the Patent Cooperation Treaty to European Patent Application Serial No. 14178012.2, filed Jul. 22, 2014.

TECHNICAL FIELD

The application relates to the field of structural biology. More specifically, the disclosure relates to methods for the identification and characterization of biomolecular tools allowing the selective recognition and/or stabilization of distinct conformational states of protein complexes, including transient protein-protein interactions and protein-nucleic acid complexes. Such tools can then be used for purification purposes, crystallization and structure determination of these stabilized protein complexes, for drug discovery, as research tools, as well as for diagnosis and treatment of diseases.

BACKGROUND

Transient molecular interactions between macromolecules provide a powerful mechanism in biology to regulate function and cell processes. A crucial step toward the full understanding of cellular systems consists of mapping the networks of physical DNA-, RNA- and protein-protein interactions of an organism of interest as completely and accurately as possible, the "interactome network." Recently, a large number of biological pathway and network databases have been developed to capture the expanding knowledge of molecular interactions. However, the complete understanding of molecular interactions requires high-resolution 3D structures as they provide key atomic details about binding interfaces and information about structural changes that accompany molecular interactions.

The interactions of two or more dissimilar proteins, the so-called protein-protein interactions (PPIs), are central to most biological processes. Critical cellular functions, including cell growth, DNA replication, transcription activation, translation and transmembrane signal transduction, are all regulated by multiprotein complexes and, therefore, quaternary protein structures represent a large and attractive emerging class of targets for human therapeutics.[1-4] It is now well established that human diseases can be caused by aberrant PPIs, either through the loss of an essential interaction or through the formation and/or stabilization of a protein-protein interaction at an inappropriate time or location. Proteins themselves are dynamic and can exist in multiple conformations, often induced by interaction with another protein in a (transient) protein-protein interaction. These conformational changes are often functionally important and reflect allosteric regulation that activate or inactivate specific protein functions. The diversity and complexity of these highly dynamic PPIs present many opportunities and challenges for the identification of drug-like molecules with the ability to modulate the PPI with the necessary selectivity and potency.

PPIs can occur between identical or non-identical chains (homo- or hetero-oligomers). Besides composition, non-obligate and obligate complexes can be distinguished. In an obligate PPI, the protomers are not found as stable structures on their own in vivo. The components of non-obligate complexes are independently stable. In contrast to a permanent interaction that only exists in its complexed form, a transient interaction associates and dissociates in vivo. Weak transient interactions that feature a dynamic oligomeric equilibrium in solution, where the interaction is broken and formed continuously and strong transient associations that require a molecular trigger to shift the oligomeric equilibrium are distinguished. Many PPIs do not fall into distinct types. Rather, there is a continuum between obligate and non-obligate interactions, and the stability of transient complexes varies much depending on physiological conditions and environment.[5]

Yeast two-hybrid screens have been used extensively to map binary transient interactions and tandem affinity purification run in conjunction with mass spectroscopy and chemical cross-linking has been developed to detect transiently formed complexes. A large number of biological network databases have been developed to capture the expanding knowledge of protein-protein interactions but rigorous assessment of high-throughput as well as literature-curated PPI data has shown that experimental data can be prone to error and are not completely comprehensive.[5] Therefore, computational methods can be applied to increase confidence and predict interactions currently hidden from the experimental techniques.[6]

Ultimately, the complete understanding of molecular interactions requires high-resolution 3D structures as they provide key atomic details about binding interfaces and information about structural changes that accompany protein-protein interactions. The structural details of these interactions, often necessary to understand their function, are only available for a tiny fraction and this gap is growing.[7] Modern overexpression and purification procedures can usually supply sufficient material for structural studies on a single protein, but obtaining sufficient material can be an enormous problem for large multiprotein complexes. But even if expression and purification problems can be overcome, we are still confronted with the intrinsic property that these complexes are transient, complicating their structural characterization X-ray crystallography, Nuclear Magnetic Resonance (NMR), Small Angle X-ray Scattering (SAXS) or Electron microscopy (EM). The transient nature of these PPIs also makes them difficult targets for drug discovery.

The structural characterization of multiprotein complexes is currently limited to permanent protein-protein interactions or to transient interactions that can be stabilized by i) binding of small molecule effectors (such as nucleotides, substrates, ions, or analogs thereof), ii) naturally occurring ligands, or iii) introduction of stabilizing mutations to the interacting protomers of the PPI. Antibodies and fragments derived thereof have been identified that are able to bind quaternary protein structures.[8] However, none of these antibodies (or fragments) selectively stabilize the PPI, i.e., preferentially interact with the protein complex versus one of the interacting protomers. Camelid single-domain antibody fragments (VHHs or NANOBODIES®) have been identified that bind conformational epitopes of (membrane) proteins and complexes thereof (Pardon et al., 2014). For example, NANOBODIES® that stabilize a complex composed of agonist-occupied monomeric β2-adrenergic receptor and nucleotide-free Gs heterotrimer were identified by (i) immunizing llamas with the complex after chemical cross-linking of the associating proteins to mature NANOBODIES® that bind allosteric epitopes on the transient complex, and (ii) two different panning strategies. These NANOBODIES® were able to protect the complex from dissociation by GTPγS and provide stabilization to the G protein subunits, which was essential for determining its crystal structure. Conformational antibodies that stabilize particular conformers of single proteins and methods to identify these have also been described (Rasmussen et al., 2011; Kruse et al., 2013). However, generic methods to identify allosteric modulators that bind at a site orthogonal to the protein-protein interface, inducing conformational changes that affect the protomers' propensity to form a complex, are lacking.

There is, thus, a need for straightforward methods for the selection of novel tools that selectively stabilize transient protein complexes, making them amenable for structural investigation and drug discovery.

BRIEF SUMMARY

Many protein-protein interactions (PPIs) are regulated by allosteric modulators that bind at a site orthogonal to the protein-protein interface, inducing/stabilizing conformational changes that affect the protomers' propensity to form a complex. Here provided is a generic method for the generation and selection of allosteric binding agents that stabilize transient protein complexes. Such binding agents are instrumental in purifying, crystallizing and solving the structures of transient complexes that have been resistant to structural investigation by conventional methods. These binding agents are also useful for drug discovery against a target protein complex, as research tools, as well as for diagnosis and treatment of diseases that are associated with a particular protein complex conformation.

Owing to the cooperative nature of structural transitions in proteins, the molecular mechanisms behind protein association are poorly understood. However, thermodynamic cycles are a well-established approach for analyzing the energetics of interactions within or between macromolecules. The thermodynamic cycle presented in FIG. 1 is useful for quantifying the contribution of a binding agent (a NANOBODY® is taken as the example) to the stability of a transient complex.

The association of two proteins (A and B in FIG. 1) generates new conformational epitopes in the transient complex A-B. On the one hand, new epitopes are formed by the A-B interface. On the other hand, A and B may undergo significant conformational changes upon association, generating new conformational epitopes that are not represented in the protomers. Protein-protein interaction (PPI) stabilizing tools (for example, a NANOBODY® in FIG. 1) selectively bind epitopes that are unique to the transient complex.

Thermodynamics imply that any binding agent that preferentially binds an allosteric structural feature, unique to the transient complex ($K_{binding\ agent}/K'_{binding\ agent}>1$), will stabilize this complex proportionally:

$$K_{binding\ agent} \times K'_d = K'_{binding\ agent} \times K_d \text{ or } K_{binding\ agent}/K'_{binding\ agent} - K_d/K'_d$$

This means that, for example, an allosteric antibody raised against a (conformational) epitope, unique to the transient complex, will stabilize this complex by the principle of mass action. This thermodynamic concept can be expanded beyond binary interactions.

Thus, here provided is a selection method for binding agents that specifically bind to a protein complex and not to the constituting members of the protein complex. It should be clear that the transient protein complex within the context of this disclosure can be formed from the association of two or more constituting members (as defined further herein). Binding agents that are selected by the method of the disclosure are able to selectively stabilize distinct conformations of a protein complex.

Preferably, these binding agents not only can be used to stabilize the protein complex itself, but will also stabilize one of the constituting members in the protein complex conformation, in absence of its interacting partner(s).

Notably, the selection method that is provided herein can simultaneously be used to:

(i) select binding agents that selectively bind to one of the constituting members of the protein complex (and not to the protein complex itself nor the other constituting member(s) of the protein complex), and/or (ii) select binding agents that selectively bind to one of the individual members of a protein complex and to the protein complex (and not to the other individual member(s) of the complex).

Thus, according to a first aspect, the disclosure relates to a method to select conformation-selective binding agents of a protein complex, the method comprising the steps of:

a) Displaying a collection of binding agents at the extracellular surface of a population of cells;

b) Using cell sorting to separate, from the population of cells of b), cells displaying binding agents that:
   i. specifically bind to a protein complex conformation and not to the individual members of the complex; and/or
   ii. specifically bind to one of the individual members of a protein complex and not to the protein complex conformation nor to the other individual member(s) of the complex; and/or
   iii. specifically bind to one of the individual members of a protein complex and to a protein complex conformation and not to the other individual member(s) of the complex.

In a particular embodiment of the above method, the individual members of the protein complex are distinguishably tagged and step b) comprises the steps of:

a) Incubating a mixture of distinguishably tagged individual members of a protein complex with the population of cells under suitable conditions to allow binding to the cells;

b) Using cell sorting to select, from the population of cells, cells displaying binding agents that:
   i. specifically bind to a protein complex conformation and not to the individual members of the complex; and/or
   ii. specifically bind to one of the individual members of a protein complex and not to the protein complex conformation nor to the other individual member(s) of the complex; and/or
   iii. specifically bind to one of the individual members of a protein complex and to a protein complex conformation and not to the other individual member(s) of the complex.

In a preferred embodiment of the above method, at least one of the individual members of the protein complex is labeled with a fluorescent label. More preferably, the individual members of the protein complex are each labeled with a distinguishable fluorescent label.

According to a specific embodiment of the above method, the cell sorting in step b) is done using FACS.

Preferably, the protein complex in any of the above methods is a protein-protein complex that is constituted of at least two interacting monomeric proteins. Alternatively, the protein complex is a protein-nucleic acid complex that is constituted of at least one monomeric protein interacting with at least one nucleic molecule.

The method may further comprise the step of isolating the binding agent from the cell sorted in step b). The method may also comprise the step of measuring the binding specificity and/or affinity of the binding agent for the protein complex conformation as compared to the individual members of the protein complex by any suitable technique, such as biophysical method or FACS.

In a preferred embodiment of any of the above methods, the plurality of binding agents is a library of antibodies or antibody fragments. More preferably, the antibody fragments are immunoglobulin single-domain antibodies, in particular, NANOBODIES®. The antibodies or antibody fragments are preferably obtained from an animal that has been immunized with the protein complex in a cross-linked form.

In one specific embodiment, the population of cells as used in any of the above methods is a population of yeast cells.

According to another aspect, the disclosure also encompasses a composition comprising a binding agent obtained by any of the above methods.

In still another aspect, the disclosure relates to a composition comprising a protein complex and a binding agent obtained by any of the above methods, whereby the protein complex is stabilized by the binding agent.

Further embodiments will be found in the detailed description.

BRIEF DESCRIPTION OF THE DRAWINGS

FIG. 3. SDS-PAGE of the cross-linked RIC8A•Gαi1 transient complex. Lane 1 is a molecular weight marker (Bio-Rad). Lanes 2 and 3 are duplicates of samples cross-linked for 5 minutes with K100 (Covalx) and BS3 (Thermo Scientific). Lanes 4 and 5 are duplicates of samples cross-linked for 30 minutes, respectively.

FIG. 4. Stepwise co-selection by FACS of NANOBODIES® that bind to RIC8A•Gαi but not to RIC8A alone or Gαi alone. RIC8A was separately labeled with the fluorescent dye DYLIGHT®-405 (Life Technologies). Gαi1 was separately labeled with the fluorescent dye DYLIGHT®-488 (Life Technologies). For each round of selection, a three-color FACS sort was performed on R-Phycoerythrin fluorescence (confirming the expression of the displayed Nb, not shown), DYLIGHT®-405 fluorescence (measuring the binding of RIC8A to the yeast cells), and DYLIGHT®-488 (measuring the binding of Gαi1 to the yeast cells).

FIG. 5. AA sequence alignment (CLC viewer) of NANOBODIES® resulting from the selection for binders to the RIC8A•Gαi complex (SEQ ID NOS:51-65).

FIG. 6. Stepwise co-selection by FACS of NANOBODIES® that bind to RIC8A alone but not the RIC8A•Gαi complex or Gαi alone. For each round of selection, a three-color FACS sort was performed on R-Phycoerythrin fluorescence (not shown), DYLIGHT®-405 fluorescence (measuring the binding of RIC8A to the yeast cells), and DYLIGHT®-488 (measuring the binding of Gαi1 to the yeast cells).

FIGS. 8A-8E. Summary of the different interaction profiles of NANOBODIES® in a FACS screening experiment. Target molecules for NANOBODY® binding: RIC8A-DYLIGHT®-405, Gαi1-DYLIGHT®-488, RIC8A-DYLIGHT®-405/Gαi1-DYLIGHT®-488 complex. Results are shown as dot blots or histograms where the signal of a specific NANOBODY® (black) is compared to the FACS signal of an irrelevant NANOBODY® (gray). For each clone, a three-color FACS analysis was performed on R-Phycoerythrin fluorescence (not shown), DYLIGHT®-405 fluorescence (measuring the binding of RIC8A to the yeast cells), and DYLIGHT®-488 (measuring the binding of Gail to the yeast cells). The following representative clones were chosen to illustrate the binding profiles: FIG. 8A and FIG. 8B upper panel: clone CA8316 (type 1), FIG. 8B lower panel and FIG. 8C: clone CA8322 (type 2), and FIG. 8D and FIG. 8E: clone CA8417 (type 3).

FIGS. 11A and 11B. Stepwise selection by FACS of NANOBODIES® that bind to DNAgyraseCFX but not to gyrase alone. DNA was separately labeled with the fluorescent dye ALEXA FLUOR®-488 (Life Technologies). Gyrase was unlabeled, since this interferes with complex formation. For each round of selection, a two-color FACS sort was performed on R-Phycoerythrin fluorescence (confirming the expression of the displayed Nb) and ALEXA FLUOR®-488 (measuring the binding of DNA, or more generally, DNA•gyrase•CFX, to the yeast cells). There is a distinction made in FACS sort Rounds 3 and 4 between condition DNA•gyrase•CFX (plots Round 1-4 in FIG. 11A) and condition b) DNA•gyrase (plots Round 3b and 4b in FIG. 11B).

FIG. 12. AA sequence alignment (CLC viewer) of NANOBODIES® resulting from the selection for DNA•gyrase•CFX and DNA•gyrase binders (SEQ ID NOS: 70-75).

FIG. 13. Stepwise selection by FACS of NANOBODIES® that bind to gyrase alone. Gyrase was labeled with DYLIGHT®-405. For each round of selection, a two-color FACS sort was performed on R-Phycoerythrin fluorescence (confirming the expression of the displayed Nb) and DYLIGHT®-405 (measuring the binding of gyrase to the yeast cells).

FIG. 14. AA sequence alignment (CLC viewer) of NANOBODIES® resulting from the selection for gyrase binders (SEQ ID NOS:70, 71, 76, 77, 72, 73, 78, 75, respectively).

FIG. 15A: DNA ALEXA FLUOR®-647•gyrase•CFX; FIG. 15B: DNA-ALEXA FLUOR®-647•gyrase; and FIG. 15C: gyrase-DYLIGHT®-405. Results are shown as dot blots or histograms where the signal of a specific NANOBODY® (black) is compared to the FACS signal of an irrelevant NANOBODY® (gray). For each clone, a two-color FACS analysis was performed on R-Phycoerythrin fluorescence (not shown), ALEXA FLUOR®-647 fluorescence (measuring the binding of DNA or to the yeast cells) or DYLIGHT®-405 (measuring the binding of gyrase to the yeast cells). The following representative clones were chosen to illustrate the binding profiles: CA9302 (type 1) and CA9306 (type 2).

DETAILED DESCRIPTION

Definitions

Figure 1:
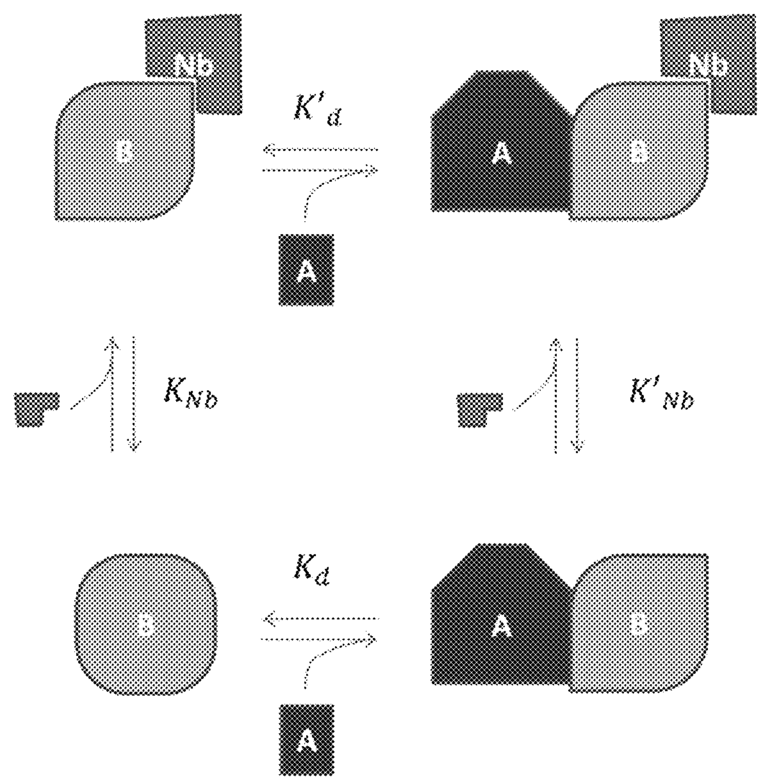
FIG. 1. Allosteric ternary binding model to analyze the effect of conformational NANOBODIES® on the oligomeric state of a transient PPI. Equivalent cycles can be drawn for Nbs that bind changing conformational epitopes on A or for antibodies that bind changing conformational epitopes consisting of elements of A and B.

This disclosure will be described with respect to particular embodiments and with reference to certain drawings but the disclosure is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun, e.g., "a," "an," or "the," this includes a plural of that noun unless something else is specifically stated. Furthermore, the terms "first," "second," "third," and the like, in the description and in the claims, are used for distinguishing between similar elements and not necessarily for describing a sequential or chronological order. It is to be understood that the terms so used are interchangeable under appropriate circumstances and that the embodiments of the disclosure described herein are capable of operation in other sequences than described or illustrated herein.

Unless otherwise defined herein, scientific and technical terms and phrases used in connection with this disclosure shall have the meanings that are commonly understood by those of ordinary skill in the art. Generally, nomenclatures used in connection with, and techniques of molecular and cellular biology, structural biology, biophysics, pharmacology, genetics and protein and nucleic acid chemistry described herein are those well known and commonly used in the art. The methods and techniques of this disclosure are generally performed according to conventional methods well known in the art and as described in various general and more specific references that are cited and discussed throughout the present specification unless otherwise indicated. See, for example, Sambrook et al., *Molecular Cloning: A Laboratory Manual,* 3$^{rd}$ ed., Cold Spring Harbor Laboratory Press, Cold Spring Harbor, N.Y. (2001); Ausubel et al., *Current Protocols in Molecular Biology*, Greene Publishing Associates (1992, and Supplements to 2002); Rupp, *Biomolecular Crystallography: Principles, Practice and Applications to Structural Biology,* 1$^{st}$ edition, Garland Science, Taylor & Francis Group, LLC, an informa Business, N.Y. (2009); Limbird, *Cell Surface Receptors,* 3d ed., Springer (2004); *Flow Cytometry Protocols,* 2$^{nd}$ ed. Humana Press (2004); *Antibody Engineering,* 2$^{nd}$ ed. Springer (2010).

As used herein, the terms "polypeptide," "protein," and "peptide" are used interchangeably herein, and refer to a polymeric form of amino acids of any length, which can include coded and non-coded amino acids, chemically or biochemically modified or derivatized amino acids, and polypeptides having modified peptide backbones. Throughout the application, the standard one letter notation of amino acids will be used. Typically, the term "amino acid" will refer to "proteinogenic amino acid," i.e., those amino acids that are naturally present in proteins. Most particularly, the amino acids are in the L isomeric form, but D amino acids are also envisaged.

As used herein, the terms "nucleic acid molecule," "polynucleotide," "polynucleic acid," and "nucleic acid" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

The term "binding agent," as used herein, means the whole or part of a proteinaceous (protein, protein-like or protein containing) molecule that is capable of binding using specific intermolecular interactions to a target protein. In particular, the term "binding agent" is not meant to include a naturally occurring binding partner of the protein. More specifically, the term "binding agent" refers to a polypeptide, more particularly, a protein domain. A suitable protein domain is an element of overall protein structure that is self-stabilizing and that fold independently of the rest of the protein chain and is often referred to as "binding domain." Such binding agents vary in length from between about 25 amino acids up to 500 amino acids and more. Many binding domains can be classified into folds and are recognizable, identifiable, 3-D structures. Some folds are so common in many different proteins that they are given special names. Non-limiting examples are binding agents selected from a 3- or 4-helix bundle, an armadillo repeat domain, a leucine-rich repeat domain, a PDZ domain, a SUMO or SUMO-like domain, a cadherin domain, an immunoglobulin-like domain, a phosphotyrosine-binding domain, a pleckstrin homology domain, an src homology 2 domain, amongst others. A binding agent can, thus, be derived from a naturally occurring molecule, e.g., from components of the innate or adaptive immune system, or it can be entirely artificially designed. A binding agent can, thus, be immunoglobulin-based or it can be based on domains present in proteins including, but not limited to, microbial proteins, protease inhibitors, toxins, fibronectin, lipocalins, single-chain antiparallel coiled coil proteins or repeat motif proteins. Particular examples of binding agents that are known in the art include, but are not limited to: antibodies, heavy chain antibodies (hcAb), single domain antibodies (sdAb), minibodies, the variable domain derived from camelid heavy chain antibodies (VHH or NANOBODIES®), the variable domain of the new antigen receptors derived from shark antibodies (VNAR), alphabodies, protein A, protein G, designed ankyrin-repeat domains (DARPins), fibronectin type III repeats, anticalins, knottins, engineered CH2 domains (nanoantibodies), engineered SH3 domains, affibodies, peptides and proteins, lipopeptides (e.g., pepducins) (see, e.g., Gebauer & Skerra, (2009) *Current Opinion in Chemical Biology* 13:245-255; Skerra, *J. Molecular Recognition* 13:167-187 (2000); Starovasnik et al., *Proc. Natl. Acad. Sci. USA* 94:10080-10085 (1997); Binz et al., *Nature Biotech.* 22:575-582 (2004); Koide et al., *J. Mol. Biol.* 284:1141-1151 (1998); Dimitrov, *MAbs.* 2009 January-February; 1(1):26-8; P.-A. Nygren (2008), *FEBS J.* 275:2668-2676; and WO2010066740). Frequently, when generating a particular type of binding agent using selection methods, combinatorial libraries comprising a consensus or framework sequence containing randomized potential interaction residues are used to screen for binding to a molecule of interest, such as a protein.

As used herein, the term "protein complex" refers to a group of two or more associated macromolecules, whereby at least one of the macromolecules is a protein. A "protein complex," as used herein, typically refers to associations of macromolecules that can be formed under physiological conditions. Individual members of a protein complex are linked by non-covalent interactions. Within the scope of the disclosure, a protein complex can be a non-covalent interaction of only proteins, and is then referred to as a protein-protein complex (as defined hereafter); for instance, a non-covalent interaction of two proteins, of three proteins, of four proteins, etc. As used herein, a protein complex can also be a non-covalent interaction of at least one protein and at least another macromolecule, such as a nucleic acid, and is then referred to as a protein-nucleic acid complex (as defined hereafter); for instance, a non-covalent interaction of one protein and one nucleic acid, two proteins and one nucleic acid, two proteins and two nucleic acids, etc. It will be understood that a protein complex can be multimeric. Each interacting macromolecule of a protein complex is herein referred to as an "individual member" or "member" of the protein complex. Accordingly, an individual member of a protein complex can be a monomeric protein, a nucleic acid, or another macromolecule. Protein complex assembly can result in the formation of homo-multimeric or hetero-multimeric complexes. Moreover, interactions can be stable or transient. More details are provided further in the Description.

In general, the term "naturally occurring" in reference to a member protein of a protein complex means a protein that is naturally produced (e.g., by a wild-type mammal such as a human). Such proteins are found in nature. The term "non-naturally occurring" means a protein that is not naturally occurring. Naturally occurring proteins that have been mutated by an amino acid substitution, deletion, and/or insertion, and variants of naturally occurring proteins, e.g., epitope-tagged proteins or proteins lacking their native N and/or C-terminus, are examples of non-naturally occurring proteins. Non-limiting examples of either naturally occurring or non-naturally occurring proteins within the context of this disclosure are provided further herein.

An "epitope," as used herein, refers to an antigenic determinant of a polypeptide. An epitope could comprise three amino acids in a spatial conformation, which is unique to the epitope. Generally, an epitope consists of at least 4, 5, 6, or 7 such amino acids, and more usually, consists of at least 8, 9, or 10 such amino acids. Methods of determining the spatial conformation of amino acids are known in the art, and include, for example, x-ray crystallography and multi-dimensional nuclear magnetic resonance.

A "conformational epitope," as used herein, refers to an epitope comprising amino acids in a spatial conformation that is unique to a folded three-dimensional conformation of a polypeptide. Generally, a conformational epitope consists of amino acids that are discontinuous in the linear sequence but that come together in the folded structure of the protein. However, a conformational epitope may also consist of a linear sequence of amino acids that adopts a conformation that is unique to a folded three-dimensional conformation of the polypeptide (and not present in a denatured state). In protein complexes, conformational epitopes consist of amino acids that are discontinuous in the linear sequences of one or more polypeptides that come together upon folding of the different folded polypeptides and their association in a unique quaternary structure. Similarly, conformational epitopes may here also consist of a linear sequence of amino acids of one or more polypeptides that come together and adopt a conformation that is unique to the quaternary structure.

The term "conformation" or "conformational state" of a protein refers generally to the range of structures that a protein may adopt at any time. One of skill in the art will recognize that determinants of conformation or conformational state include a protein's primary structure as reflected in a protein's amino acid sequence (including modified amino acids) and the environment surrounding the protein. The conformation or conformational state of a protein also relates to structural features such as protein secondary structures (e.g., α-helix, β-sheet, among others), tertiary structure (e.g., the three-dimensional folding of a polypeptide chain), and quaternary structure (e.g., interactions of a polypeptide chain with other protein subunits). Post-translational and other modifications to a polypeptide chain such as ligand binding, phosphorylation, sulfation, glycosylation, or attachments of hydrophobic groups, among others, can influence the conformation of a protein. Furthermore, environmental factors, such as pH, salt concentration, ionic strength, and osmolality of the surrounding solution, and interaction with other proteins and co-factors, among others, can affect protein conformation. The conformational state of a protein may be determined by either functional assay for activity or binding to another molecule or by means of physical methods such as X-ray crystallography, NMR, or spin labeling, among other methods. For a general discussion of protein conformation and conformational states, one is referred to Cantor and Schimmel, *Biophysical Chemistry, Part I: The Conformation of Biological Macromolecules*, W.H. Freeman and Company, 1980, and Creighton, *Proteins: Structures and Molecular Properties*, W.H. Freeman and Company, 1993.

The term "stabilizing" or "stabilized," as used herein, refers to the capability of a binding agent to selectively bind a specific conformation of a protein complex and to maintain the protein complex in this specific conformation. Within this context, a binding agent that selectively binds to a specific conformation of a protein complex refers to a binding agent that binds with a higher affinity to the protein complex than to the individual interacting members. One of skill in the art will recognize that binding agents that specifically or selectively bind to a specific conformation of a protein complex will stabilize this specific conformation.

The term "affinity," as used herein, refers to the degree to which a ligand binds to an antigen on a target protein so as to shift the equilibrium of protein and ligand toward the presence of a complex formed by their binding. Thus, for example, where an antigenic target and antibody (fragment) are combined in relatively equal concentration, an antibody (fragment) of high affinity will bind to the available antigen so as to shift the equilibrium toward high concentration of the resulting complex. The dissociation constant is commonly used to describe the affinity between the ligand and the antigenic target. Considering a simple bi-molecular association (L+A⇆LA, L: ligand, A: protein A), the equilibrium dissociation constant (Kd in M) is defined as the product of the concentration of the unbound species A and L divided by the concentration of the complex AL:

$$K_d = \frac{[A][L]}{[AL]}.$$

In a similar way, the equilibrium dissociation constant can also be defined for ternary complexes. For example, $$K_d = \frac{[A][B][L]}{[ABL]}$$

(L forms a ternary complex with proteins A and B), which would have units in $M^2$. To calculate how tightly the Ligand (L) binds to the existing complex AB, a Kd for that reaction can easily be defined as follows:

$$K_d = \frac{[AB][L]}{[ABL]}.$$

This is effectively a bimolecular reaction in which the complex AB is treated as if it were a single molecule. However, it should be noticed that the concentration of the binary complex AB is itself a function of [A] and [B]. Typically, the dissociation constant is lower than $10^{-5}$ M. Preferably, the dissociation constant is lower than $10^{-6}$ M, more preferably, lower than $10^{-7}$ M. Most preferably, the dissociation constant is lower than $10^{-8}$ M. Other ways of describing the affinity between a ligand and its target protein are the association constant (Ka), the inhibition constant (Ki), or indirectly by evaluating the potency of ligands by measuring the half maximal inhibitory concentration (IC50) or half maximal effective concentration (EC50). For example, within the scope of the disclosure, the ligand may be a binding agent, preferably an immunoglobulin, such as an antibody, or an immunoglobulin fragment, such as a VHH or NANOBODY®, that binds a conformational epitope on a protein complex, that is not represented on the individual members of the complex. Alternatively, the ligand may be a binding agent, preferably an immunoglobulin, such as an antibody, or an immunoglobulin fragment, such as a VHH or NANOBODY®, that binds a conformational epitope on one of the individual members of a protein complex, that is not represented on the protein complex.

The term "specificity," as used herein, refers to the ability of a binding agent, in particular, an immunoglobulin or an immunoglobulin fragment, such as a VHH or NANOBODY®, to bind preferentially to one antigen, versus a different antigen, and does not necessarily imply high affinity.

The terms "specifically bind" and "specific binding," as used herein, generally refers to the ability of a binding agent, in particular, an immunoglobulin, such as an antibody, or an immunoglobulin fragment, such as a VHH or NANOBODY®, to preferentially bind to a particular antigen that is present in a homogeneous mixture of different antigens. In certain embodiments, a specific binding interaction will discriminate between desirable and undesirable antigens in a sample, in some embodiments more than about 10- to 100-fold or more (e.g., more than about 1000- or 10,000-fold). Within the context of the disclosure, the terms particularly refer to the ability of a binding agent to preferentially recognize and/or bind to a protein complex and not to the individual interacting members.

As used herein, the term "conformation-selective binding agent" refers to a binding agent that binds to a target protein in a conformation-selective manner. A binding agent that selectively binds to a particular conformation of a protein refers to a binding agent that binds with a higher affinity to a protein in a subset of conformations than to other conformations that the protein may assume. One of skill in the art will recognize that binding agents that selectively bind to a specific conformation will stabilize or retain the protein in this particular conformation. For example, a conformation-selective binding agent for a protein complex will preferentially bind to the protein complex and will not, or to a lesser degree, bind to any of the individual members of the complex, and will thus have a higher affinity for the protein complex conformation, or vice versa. The terms "specifically bind," "selectively bind," "preferentially bind," and grammatical equivalents thereof, are used interchangeably herein. The terms "conformational specific" or "conformational selective" are also used interchangeably herein.

As used herein, the term "ligand" means a molecule that specifically binds to a protein or a protein complex. A ligand may be, without the purpose of being limitative, a polypeptide, a lipid, a small molecule, an antibody, an antibody fragment, a nucleic acid, or a carbohydrate. A ligand may be synthetic or naturally occurring. A ligand also includes a "native ligand," which is a ligand that is an endogenous, natural ligand for a native protein complex. A ligand may be an agonist, a partial agonist, an inverse agonist, an antagonist, an allosteric modulator, and may bind at either the orthosteric site or at an allosteric site. In particular embodiments, a ligand may be a "conformation-selective ligand" or "conformation-specific ligand," meaning that such a ligand binds the protein complex in a conformation-selective manner. A conformation-selective ligand binds with a higher affinity to a particular conformation of the protein complex than to the individual members of the complex.

The term "antibody" is intended to mean an immunoglobulin or any fragment thereof that is capable of antigen binding. The term "antibody" also refers to single chain antibodies and antibodies with only one binding domain.

As used herein, the terms "complementarity-determining region" or "CDR" within the context of antibodies refer to variable regions of either H (heavy) or L (light) chains (also abbreviated as VH and VL, respectively) and contains the amino acid sequences capable of specifically binding to antigenic targets. These CDR regions account for the basic specificity of the antibody for a particular antigenic determinant structure. Such regions are also referred to as "hypervariable regions." The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all canonical antibodies each have three CDR regions, each non-contiguous with the others (termed L1, L2, L3, H1, H2, and H3) for the respective light (L) and heavy (H) chains. Immunoglobulin single-variable domains, in particular, NANOBODIES®, generally comprise a single amino acid chain that can be considered to comprise four "framework sequences or regions" or FRs and three "complementarity-determining regions" or CDRs. The NANOBODIES® have three CDR regions, each non-contiguous with the others (termed CDR1, CDR2, and CDR3). The delineation of the FR and CDR sequences can, for example, be based on the IMGT unique numbering system for V-domains and V-like domains (Lefranc et al. 2003, *Developmental and Comparative Immunology* 27:55).

As used herein, the terms "determining," "measuring," "assessing," "monitoring," and "assaying" are used interchangeably and include both quantitative and qualitative determinations.

As used herein, the term "cell sorting" refers to a technique by which individual cells of a sample are separated according to their properties, including intracellular or extracellular properties. Currently, there are several methods for cell sorting. The three major types of cell sorting are fluorescent-activated cell sorting (FACS), magnetic cell selection, including magnetic-activated cell sorting (MACS), and single cell sorting.

Other definitions may be found in the following description.

Description

In various embodiments, the disclosure provides a method to select conformation-selective binding agents that are specific for a protein complex. These binding agents specifically bind conformational epitopes that are prevalent in a protein complex structure and not represented on the individual members of the complex. These binding agents have lower affinity for the structures of the individual members of the complex. These binding agents can be used to stabilize a protein complex in a conformation that is otherwise only transiently formed, whereby the stabilization occurs via a monovalent interaction with the complex of interest (or in other words, a multispecific or multivalent type of interaction is not required for such stabilization of a protein complex of interest). For instance, and without the purpose of being limitative, a conformation-selective binding agent can be used to stabilize and purify large quantities of transient protein complexes in a particular conformational state for research purposes, including studies such as X-crystallography. In particular, the conformation-selective binding agent identified by the method of the disclosure can be used to isolate active or inactive conformations of transient protein complexes, thus eliminating the need for ligands, co-factors, or other molecules. In addition, the conformation-selective binding agents can also be used to isolate active or inactive conformations of one of the constituting members in its complex selective conformation, in absence of its interacting partner(s).

In general terms, the method to select conformation-selective binding agents of a protein complex involves displaying a collection of binding agents at the extracellular surface of a population of cells and using cell sorting to select, from the population of cells, cells displaying binding agents that specifically bind to a protein complex and not to the individual members of the complex.

The herein-described selection method may be performed on any type of macromolecular complex, including protein complexes (as defined herein), such as a protein-protein complex or a protein-nucleic acid complex. For example, a protein complex may be an interaction of one or more membrane receptors with one or more intracellular proteins (e.g., a GPCR with a G protein and/or β-arrestin[10]), an interaction of two or more membrane receptors (e.g., a dimeric/multimeric complex of receptor tyrosine kinases[11]), an interaction of two or more intracellular proteins, an interaction of a DNA binding protein and a DNA molecule, etc.

In a preferred embodiment, the selection method is performed on a protein-protein complex that is constituted of at least two interacting monomeric proteins. The terms "protein-protein complex" and "protein-protein interaction" (PPI), which are used interchangeably herein, refer to a non-covalent interaction that can be formed between two or more monomeric proteins under physiological conditions. Herein, the two or more monomeric proteins are also referred to as the "individual members" or "members" of the protein-protein interaction. It should be clear that multimeric protein-protein complexes are also envisaged here, comprising more than two interacting monomeric proteins. For the sake of clarity, a protein-protein interaction can be an interaction between identical or non-identical member proteins (homo-multimeric vs. hetero-multimeric protein-protein complex, respectively).

Even more preferably, the disclosure envisages a method to select for conformation-selective binding agents that specifically bind to a transient protein-protein complex. The term "transient protein-protein interaction" or "transient protein-protein complex," as used herein, refers to a protein-protein interaction that, under physiological conditions, can either associate into a complex, hereby adopting a particular conformation, or dissociate into a free form of two or more individual members that can stably exist on their own. Thus, in a transient interaction, a protein may interact briefly and in a reversible manner with other proteins in certain cellular contexts—cell type, cell cycle stage, external factors, presence of other binding proteins, etc.—as it happens with most of the proteins involved in biochemical cascades. For example, G protein-coupled receptors only transiently bind to G proteins when they are activated by extracellular ligands. Transient protein-protein interactions can be either weak or strong, depending on subcellular localization, physiological conditions, environment, etc. Typically, weak transient protein-protein interactions refer to transient complexes that, under physiological conditions, show a dynamic mixture of different oligomeric states. Strong transient protein-protein interactions refer to transient complexes that change their quaternary structure only when triggered, for example, by ligand binding. For the sake of clarity, a transient protein-protein interaction is different from a "permanent protein-protein interaction," which is a protein-protein interaction that only exists in its complex form. Permanent or stable interactions involve proteins that interact for a long time, taking part of permanent complexes as subunits, in order to carry out structural or functional roles. These are usually the case of homo-oligomers (e.g., cytochrome c), and some hetero-oligomeric proteins, as the subunits of ATPase.

A member protein forming part of a (transient) protein-protein interaction that can be used in the herein-described selection method, can be an intracellular protein, such as a small GTPase, a kinase, a phosphatase, etc., or a (trans) membrane protein, such as a receptor protein, e.g., a GPCR, an ion channel, transport proteins, etc., or a secreted protein such as a hormone, etc. The nature of the member protein that forms part of a (transient) protein-protein interaction is not critical to the disclosure and can be from any organism including a fungus (including yeast), nematode, virus, insect, plant, bird (e.g., chicken, turkey), reptile or mammal (e.g., a mouse, rat, rabbit, hamster, gerbil, dog, cat, goat, pig, cow, horse, whale, monkey, camelid, or human). Preferably, the member protein is of mammalian origin, even more preferably, of human origin. Also, a member protein forming part of a (transient) protein-protein interaction may be naturally occurring or non-naturally occurring (i.e., altered or designed by man), as long as protein complex formation can still occur. Mutants or variants of naturally occurring proteins are examples of non-naturally occurring proteins. Non-naturally occurring proteins may have an amino acid sequence that is at least 70% identical to, at least 80% identical to, at least 90% identical to, at least 95% identical to or at least 99% identical to, a naturally occurring protein. In one specific embodiment, a member protein may have a deletion (e.g., N- and/or C-terminal deletion, loop deletion, etc.), or a substitution, or an insertion or addition in relation to its amino acid or nucleotide sequence, or any combination thereof. In addition, the term "non-naturally occurring" is intended to encompass wild-type polymorphic variants, interspecies homologues, and alleles of member proteins forming part of a (transient) protein-protein interaction according to the disclosure.

The current method can be applied on any protein complex that is described in the art.[5] Molecular interactions can occur between molecules belonging to different biochemical families (proteins, nucleic acids, lipids, carbohydrates, etc.) and also within a given family. Whenever such molecules are connected by physical interactions, they form molecular interaction networks that are generally classified by the nature of the compounds involved. In general, "interactome" refers to an interaction network, such as "protein—protein interaction networks" (for example, the human interactome[12]) or subsets thereof. Another extensively studied type of interactome is the protein—DNA interactome, also called a "gene-regulatory network," a network formed by transcription factors, chromatin regulatory proteins, and their target genes. Notably, there are a multitude of methods to detect currently unknown interactions. For example, methods to detect protein-protein interactions, which are known by the person skilled in the art and reviewed in, e.g., V. Srinivasa Rao et al. (2014), "Protein-Protein Interaction Detection: Methods and Analysis," *Int. J. Proteomics* 2014: 147648, and incorporated herein by reference. Protein-protein interaction detection methods are categorically classified into three types, namely, in vitro, in vivo, and in silico methods. In in vitro techniques, a given procedure is performed in a controlled environment outside a living organism. The in vitro methods in PPI detection are tandem affinity purification, affinity chromatography, coimmunoprecipitation, protein arrays, protein fragment complementation, phage display, X-ray crystallography, NMR spectroscopy, and proximity-based methods like Fluorescence Resonance Energy Transfer (FRET), Bioluminescence Resonance Energy Transfer (BRET), and Amplified Luminescent Proximity Homogeneous Assay Screen (ALPHA Screen). In in vivo techniques, a given procedure is performed on the whole living organism itself. The in vivo methods in PPI detection are yeast two-hybrid (Y2H, Y3H) and synthetic lethality. In silico techniques are performed on a computer or via computer simulation. The in silico methods in PPI detection are sequence-based approaches, structure-based approaches, chromosome proximity, gene fusion, in silico 2 hybrid, mirror tree, phylogenetic tree, and gene expression-based approaches. The most conventional and widely used high-throughput methods are yeast two-hybrid screening and affinity purification coupled to mass spectrometry. It will be understood that the herein-described method also encompasses the use of such novel identified protein complex targets.

Alternatively, the method may also be performed on a protein-nucleic acid complex, more specifically a protein-DNA complex or a protein-RNA complex. The term "protein-nucleic acid complex" refers to a non-covalent interaction that can be formed between at least one monomeric protein and at least one nucleic acid, such as a DNA or an RNA molecule, under physiological conditions. Herein, at least one monomeric protein and at least one nucleic acid are also referred to as the "individual members" or "members" of the protein-nucleic acid interaction. It should be clear that multimeric protein-nucleic acid complexes are also envisaged here.

Although in principle, any collection or library of binding agents may contain conformation-selective binding agents against protein complexes, a preferred method is to generate an immune library of binding agents, in particular, an immune library of antibodies or antibody fragments, by immunizing an animal with an (optionally cross-linked) protein complex to expose the immune system of the animal with the conformational epitopes that are unique to the complex. In a preferred embodiment of the method, an immune library of immunoglobulin single-variable domains (as defined hereafter) is generated.

In principle, animals could be immunized with mixtures of the interacting members of a protein complex. However, considering the short half-life of many protein complexes, which is particularly the case for transient PPIs (0.1 to 1 second) it is preferred to stabilize transient complexes by chemical cross-linking of the individual interacting members of the complex. In this way, animals can be immunized with antigens that are in a covalent association that is very similar to the transient complex to trigger and mature immunoglobulins that bind conformational epitopes of this transient complex. Methods for cross-linking members of protein-protein complexes or protein-nucleic acid complexes may be performed in accordance with any of the techniques known to those skilled in the art. Obviously, regardless of the reagent used, it is required that the reaction proceeds under conditions that preserve the native state of the protein complex. Reagents and protocols are reviewed in, e.g., A. Leitner et al., "Probing Native Protein Structures by Chemical Cross-linking, Mass Spectrometry, and Bioinformatics," *Molecular & Cellular Proteomics* 9:1634-1649 (2010); C. Bich et al., "Reactivity and applications of new amine reactive cross-linkers for mass spectrometric detection of protein-protein complexes," *Anal. Chem.* 82:172-9 (2010), all of which are incorporated herein by reference.

Chemical cross-linking reagents known in the art may be classified in several categories according to their reactivity (e.g., amine- or thiol-reactive and homo- and heterobifunctional) or the incorporation of additional functional groups (e.g., cleavable sites and affinity tags). Conventional chemical cross-linking reagents consists of two reactive sites connected through a spacer or linker region, typically an alkyl chain. Most commonly, the reactive groups of cross-linkers target the primary amino group of lysine (and the protein N termini). For this purpose, N-hydroxysuccinimidyl or sulfosuccinimidyl esters are almost exclusively used. Common succinimide-type linkers are disuccinimidyl suberate (DSS; six-carbon linker) and disuccinimidyl glutarate (DSG; three-carbon linker) as well as their sulfo analogs bis(sulfosuccinimidyl) suberate ($BS^3$) and bis(sulfosuccinimidyl) glutarate. Lysine cross-linking has several advantages, including the high prevalence of Lys residues (about 6%) and relatively high-reaction specificity. Similar specific cross-linking reactions can be carried out when targeting cysteine residues, e.g., by maleimides, but the low abundance of Cys (<2%) makes this less attractive. Other cross-linking chemistries include arginine-specific cross-linking or acidic cross-linking (Zhang et al. 2008, "Nested Arg-specific bifunctional cross-linkers for MS-based structural analysis of proteins and protein assemblies," *Anal. Chim. Acta* 627:117-128; P. Novak and G. H. Kruppa, 2008, "Intra-molecular cross-linking of acidic residues for protein structure studies," *Eur. J. Mass. Spectrom.* 14:355-365). Glutaraldehyde is also frequently used in biochemistry applications as an amine-reactive homobifunctional cross-linker. In addition to homobifunctional cross-linkers, several heterobifunctional linkers have been described. These may incorporate two different reactive groups, e.g., Lys- and Cys-reactive, or may combine different cross-linking concepts, e.g., chemical and photo-induced cross-linking. Also encompassed as a suitable cross-linking reagent is formaldehyde, which only contains a single aldehyde group but is able to connect two amino acid side chains via a two-step reaction. Formaldehyde is a less specific reagent, although lysine and tryptophan residues are primarily targeted (B. W. Sutherland et al., 2008, "Utility of formaldehyde cross-linking and mass spectrometry in the study of protein-protein interactions," *J. Mass. Spectrom.* 43:699-715; J. Toews et al., 2008, "Mass spectrometric identification of formaldehyde-induced peptide modifications under in vivo protein cross-linking conditions," *Anal. Chim. Acta* 618: 168-183).

Functionalized cross-linking reagents include linkers carrying stable isotope labels, affinity tags, or moieties that give characteristic fragmentation patterns in tandem mass spectrometry experiments. For example, different stable isotope-labeled cross-linking reagents such as DSS or $BS^3$ are commercially available from suppliers such as Creative Molecules and the Pierce Division of Thermo Scientific, and more complex reagents have also been prepared in labeled form. Amongst the affinity-tagged cross-linking reagents, biotin is most frequently used as the affinity group, allowing the isolation of modified peptides by avidin affinity chromatography (Trester-Zedlitz et al. (2003), "A Modular Cross-Linking Approach for Exploring Protein Interactions," *J. Am. Chem. Soc.* 125:2416-2425; Kang et al. 2009, "Synthesis of biotin-tagged chemical cross-linkers and their applications for mass spectrometry," *Rapid Commun. Mass Spectrom.* 23:1719-1726). Other examples include an azide-containing cross-linking reagent (M. A. Nessen et al. 2009, "Selective enrichment of azide-containing peptides from complex mixtures," *J. Proteome Res.* 8:3702-3711). Another variety of functionalized reagents uses linkers with specially designed fragmentation properties. Most frequently, these linkers contain labile bonds that are easily cleaved during collision-induced dissociation (X. Tang et al. 2005, "Mass spectrometry identifiable cross-linking strategy for studying protein-protein interactions," *Anal. Chem.* 77:311-318; Chowdhury et al. 2009, "Identification of cross-linked peptides after click-based enrichment using sequential collision-induced dissociation and electron transfer dissociation tandem mass spectrometry," *Anal. Chem.* 81:5524-5532; H. Zhang et al. 2009, "Identification of protein-protein interactions and topologies in living cells with chemical cross-linking and mass spectrometry," *Mol. Cell. Proteomics* 8:409-420).

Methods of immunization are well-known in the art. For the immunization of an animal with a (cross-linked) protein complex, the complex may be produced and purified using conventional methods that may employ expressing a recombinant form of the protein complex in a host cell, and purifying the protein complex using affinity chromatography and/or antibody-based methods. In particular embodiments, the baculovirus/Sf-9 system may be employed for expression, although other expression systems (e.g., bacterial, yeast or mammalian cell systems) may also be used. Methods for purifying protein complexes comprising membrane proteins are described in, for example, B. K. Kobilka, *Anal. Biochem.* 231:269-271 (1995); Eroglu et al., *EMBO* 2002 3:491-96; Chelikani et al., *Protein Sci.* 2006 15:1433-40; and the book *Identification and Expression of G Protein-Coupled Receptors* (Kevin R. Lynch (Ed.), 1998), among many others. Such membrane protein complexes may be reconstituted in phospholipid vesicles. Likewise, methods for reconstituting membrane proteins in phospholipid vesicles are known, and are described in: Luca et al., *Proc. Natl. Acad. Sci.* 2003 100:10706-11; Mansoor et al., *Proc. Natl. Acad. Sci.* 2006 103:3060-3065; Niu et al., *Biophys. J.* 2005 89:1833-1840; Shimada et al., *J. Biol. Chem.* 2002 277:31774-80; and Eroglu et al., *Proc. Natl. Acad. Sci.* 2003 100:10219-10224, among others. Methods for recombinant expression[13] and purifying protein complexes[14] of soluble proteins are well-known in the art. Other immunization methods include, without limitation, the use of complete cells expressing a protein complex or fractions thereof, immunization with viruses or virus-like particles expressing a protein complex of interest, amongst others (e.g., as described in WO 2010/070145, WO 2011/083141). Any suitable animal, in particular, a mammal such as a rabbit, mouse, rat, camel, sheep, cow, shark, pig, amongst others, or a bird, such as a chicken or turkey, may be immunized using any of the techniques well known in the art suitable for generating an immune response.

In one embodiment, the method as described herein involves displaying a collection of binding agents, preferably an immune library, at the extracellular surface of a population of cells. Surface display methods are reviewed in H. R. Hoogenboom[15] and include bacterial display, yeast display, and mammalian display.

Preferably, the population of cells are yeast cells. Any means to display a protein on the surface of yeast is encompassed by the present disclosure. The different yeast surface display methods all provide a means of tightly linking each binding agent encoded by the library to the extracellular surface of the yeast cell, which carries the plasmid encoding that protein. Most yeast display methods described to date use the yeast *Saccharomyces cerevisiae*, but other yeast species, for example, *Pichia pastoris*, could also be used. More specifically, in some embodiments, the yeast strain is from a genus selected from the group consisting of *Saccharomyces, Pichia, Hansenula, Schizosaccharomyces, Kluyveromyces, Yarrowia*, and *Candida*. In some embodiments, the yeast species is selected from the group consisting of *S. cerevisiae, P. pastoris, H. polymorpha, S. pombe, K lactis, Y. lipolytica*, and *C. albicans*.

Most yeast expression fusion proteins are based on GPI (Glycosyl-Phosphatidyl-Inositol) anchor proteins, which play important roles in the surface expression of cell-surface proteins and are essential for the viability of the yeast. One such protein, alpha-agglutinin consists of a core subunit encoded by AGA1 and is linked through disulfide bridges to a small binding subunit encoded by AGA2. Proteins encoded by the nucleic acid library can be introduced on the N-terminal region of AGA1 or on the C-terminal or N-terminal region of AGA2. Both fusion patterns will result in the display of the polypeptide on the yeast cell surface.

In some embodiments, fusion proteins for yeast display include an engineered protein fused to the N-terminal or C-terminal part of a protein capable of anchoring in a eukaryotic cell wall (e.g., α-agglutinin, AGA1, Flo1 or major cell wall protein of lower eukaryotes, see U.S. Pat. Nos. 6,027,910 and 6,114,147, which are hereby incorporated by reference), for example, proteins fused with the GPI fragment of Flo1 or to the Flo1 functional domain (Kondo et al., *Appl. MicroBiol. Biotechn.,* 2004, 64:28-40).

In certain embodiments, a method that relies on in vivo biotinylation of the protein to be displayed, followed by its capture on the yeast cell surface is used. For example, the protein to be displayed is genetically fused to a yeast secretory protein of choice and to a biotin-acceptor peptide (BAP). An epitope tag, such as HA or FLAG®, is also engineered immediately downstream from the sequence encoding the protein variant. Common secretory proteins include yeast alpha mating factor prepro 1 (WTαMFpp), the invertase leader, synthetic leaders (Clements et al., *Gene,* 106:267-271 (1991)), and the engineered alpha mating factor prepro αMFpp8 (Rakestraw et al., *Biotechnol. Bioeng.,* 103:1192-1201 (2009)). The gene encoding the fusion may be controlled by an inducible promoter, such as, for example, the galactose-inducible promoter, GAL1-10. Before inducing expression of the protein to be displayed, the outside surface of the yeast cell is chemically conjugated to avidin. Upon induction, the biotin-acceptor peptide in the fusion protein is biotinylated inside the cell by a co-expressed biotin ligase. The biotinylated fusion protein is then secreted from the cell and captured on the cell-surface avidin due to the extremely high-affinity interaction between avidin and biotin.

In certain embodiments, the protein variants to be displayed are genetically fused to a GPI (Glycosyl-Phosphatidyl-Inositol) anchor protein, such as the mating type protein agglutinin-a-1 (Aga1), flocculin proteins (e.g., Flo1), as well as Sed1, Cwp1, Cwp2, Tip1 and Tir1/Srp1. In certain embodiments, the anchor protein is selected from the group consisting of a GP1 anchor, a modified GP1 anchor, a major cell wall protein, CCW14, CIS3, CWP1, PIR1, and PIR3.

It is also contemplated that the methods disclosed herein are carried out using mammalian host cells. Examples of useful mammalian host cell lines are Chinese hamster ovary cells, including CHOK1 cells (ATCC CCL61), DXB-11, DG-44, Chinese hamster ovary cells/−DHFR (CHO, Urlaub et al., *Proc. Natl. Acad. Sci. USA* 77:4216 (1980)), and CHO cells engineered to produce controlled fucosylation (MAbs. 1(3):230-36 (2009)); monkey kidney CV1 line transformed by SV40 (COS-7, ATCC CRL 1651); human embryonic kidney line (293 or 293 cells subcloned for growth in suspension culture (Graham et al., *J. Gen. Virol.* 36:59, 1977); baby hamster kidney cells (BHK, ATCC CCL 10); mouse sertoli cells (TM4, Mather, *Biol. Reprod.* 23:243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2).

When the host cell is a mammalian cell, examples of portions of cell surface proteins that retain the ability to display proteins on the cell surface include suitable transmembrane domain of any known cell membrane proteins, or a polypeptide with a GPI anchor sequence, or a non-cleavable type II signal anchor sequence. Examples of membrane anchor sequences used for cell display in mammalian cells include PDGFR transmembrane domain (Chesnut et al., *J. Immunol. Methods* 193(1):17-27 (1996); Ho et al., *Proc. Natl. Acad. Sci. USA* 103(25):9637-42 (2006); incorporated by reference in their entirety), GPI anchor from human decay-accelerating factor (Akamatsu et al., *J. Immunol. Methods* 327(1-2):40-52 (2007); incorporated by reference in its entirety) and T-cell receptor (TCR) chain (Alonso-Camino et al., *PLoS One* 4(9):e7174 (2009); incorporated by reference in its entirety). Another example is the use of type II signal anchor sequences (U.S. Pat. No. 7,125,973; incorporated by reference in its entirety). Alternatively, a capture molecule such as an antibody or protein can be fused to a membrane anchor sequence, and displayed on the cell surface in order to capture the protein of interest (U.S. Pat. No. 6,919,183; incorporated by reference in its entirety). In certain embodiments, an artificial cell surface anchor sequence is assembled into, or attached to, the cell membrane of mammalian cells.

The methods disclosed herein may also be carried out using prokaryotic host cells. Thus, in some or any embodiments, the host cell is a prokaryotic cell. Suitable prokaryotes for this purpose include eubacteria, such as Gram-negative or Gram-positive organisms, for example, Enterobacteriaceae such as *Escherichia*, e.g., *E. coli, Enterobacter, Envinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa* and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

When the host cell is a prokaryotic cell, examples of suitable cell surface proteins include suitable bacterial outer membrane proteins. Such outer membrane proteins include pili and flagella, lipoproteins, ice nucleation proteins, and autotransporters. Exemplary bacterial proteins used for heterologous protein display include LamB (Charbit et al., *EMBO J.* 5(11):3029-37 (1986); incorporated by reference in its entirety), OmpA (Freudl, *Gene* 82(2):229-36 (1989); incorporated by reference in its entirety) and intimin (Wentzel et al., *J. Biol. Chem.* 274(30):21037-43 (1999); incorporated by reference in its entirety). Additional exemplary outer membrane proteins include, but are not limited to, FliC, pullulunase, OprF, OprI, PhoE, MisL, and cytolysin. An extensive list of bacterial membrane proteins that have been used for surface display and are contemplated for use in the present disclosure are detailed in Lee et al., *Trends Biotechnol.* 21(1):45-52 (2003); Jose, *Appl. Microbiol. Biotechnol.* 69(6):607-14 (2006); and Daugherty, *Curr. Opin. Struct. Biol.* 17(4):474-80 (2007), all incorporated by reference in their entirety. In certain embodiments, the anchor protein is an artificial sequence that is assembled into, or attaches to, the outer surface of the bacterial cell.

In a preferred embodiment of the herein-described selection method, at least one of the individual members of the protein complex is distinguishably labeled, allowing detection and separation via cell sorting of cells displaying binding agents that:

i. specifically bind to a protein complex and not to the individual members of the complex, and/or
ii. specifically bind to one of the individual members of a protein complex and not to the protein complex nor to the other individual member(s) of the complex, and/or iii. specifically bind to one of the individual members of a protein complex and to a protein complex and not to the other individual member(s) of the complex.

Libraries of cells displaying binding agents on the surface are screened for antigen binding using cell sorting, e.g., by either magnetic-activated cell sorting (MACS) or fluorescent-activated cell sorting (FACS). The current method thus involves a step of incubating a mixture of distinguishably tagged individual members of a protein complex with the population of cells under suitable conditions to allow binding to the cells.

In a preferred embodiment, cell sorting will be performed by FACS. In this scenario, it is preferred that at least one of the individual members of the protein complex is labeled with a fluorophore that can be detected in FACS with any technique known to the person skilled in the art. For example, this can be achieved by recombinant expression of a member protein with a fluorescent tag (GFP, YFP, etc.). Proteins can also be indirectly labeled by incubating with a fluorescent Ab conjugate/cascade directed against a tag (e.g., FLAG, polyhistidine, etc.) or the protein itself. In a preferred embodiment, the individual member is directly labeled via random covalent coupling of fluorescent dyes (e.g., ALEXA FLUOR®, DYLIGHT®) to amine or cysteine reactive groups of the protein. In an alternative embodiment, the cell sorting is performed with MACS. In such a scenario, it is preferred that at least one of the individual members of the protein complex is labeled with a magnetic label, for example, via streptavidin or Ab-conjugated magnetic beads.

Figure 2:
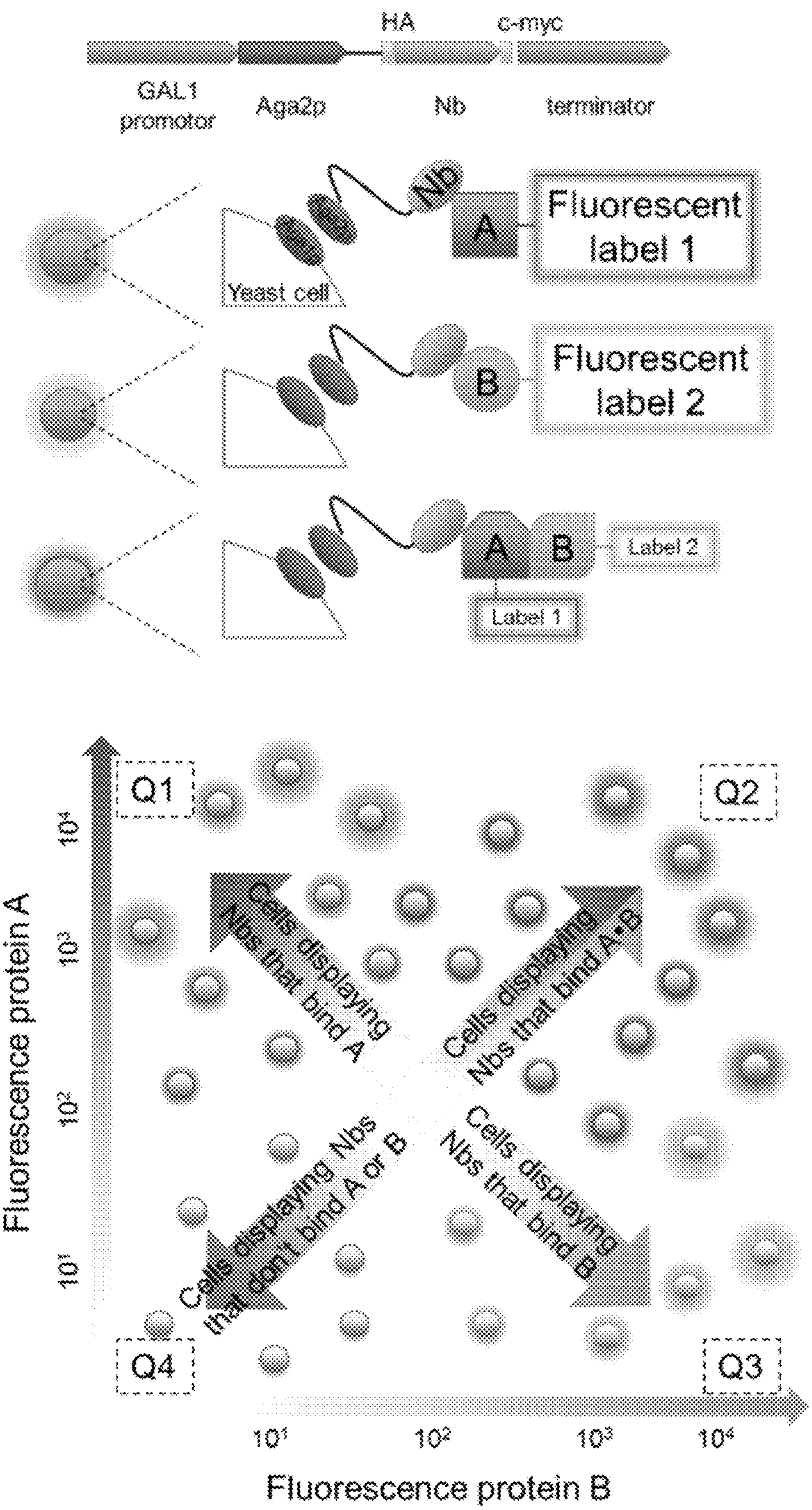
FIG. 2. FACS analysis of a library of yeast cells displaying NANOBODIES® that recognize different conformational features of a transient complex composed of proteins A and B. A and B are separately labeled with different fluorescent dyes.

FACS or MACS can be used simultaneously (1) to analyze the properties of each binding agent that is displayed multivalently on an individual cell and (2) to selectively recover cells displaying binding agents with a particular property (see, e.g., FIG. 2). Cells displaying binding agents that selectively bind a first member (A in FIG. 2) but not a second member (e.g., B in FIG. 2) or the protein complex (AB in FIG. 2) can be enriched if cells of the top-left quadrant are recovered by FACS. Cells displaying binding agents that selectively bind the second member (B in FIG. 2) but not the first member (e.g., A in FIG. 2) or the protein complex (AB in FIG. 2) can be enriched if cells of the bottom-right quadrant are recovered by FACS. Cells displaying binding agents that selectively bind the protein complex (AB in FIG. 2) but not to the first (A in FIG. 2) alone or the second member (B in FIG. 2) alone can be enriched if cells of the top-right quadrant are recovered by FACS. These processes can be repeated in several rounds to enrich for cells displaying binding agents with the desired characteristics. The selection of appropriate conditions for cell sorting by FACS or MACS is well within the skill in the art and illustrated, in a non-limiting way, in the Example section.

In additional embodiments, the current selection method may involve additional steps to further characterize the binding properties of the binding agent, for example, and without limitation, a step of affinity maturation, a step of expressing the desired amino acid sequence, a step of screening for binding and/or for activity against the desired antigen (in this case, the protein complex and/or the individual members of the complex), a step of determining the desired amino acid sequence or nucleotide sequence, a step of introducing one or more humanizing substitutions, a step of formatting in a suitable multivalent and/or multispecific format, a step of screening for the desired biological and/or physiological properties (i.e., using a suitable assay known in the art), and/or any combination of one or more of such steps, in any suitable order.

Various methods may be used to determine specific binding (as defined hereinbefore) between the binding agent and a target protein complex, including for example, enzyme linked immunosorbent assays (ELISA), flow cytometry, radioligand binding assays, surface plasmon resonance assays, phage display, and the like, which are common practice in the art, for example, as discussed in Sambrook et al. (2001), *Molecular Cloning, A Laboratory Manual,* 3rd ed., Cold Spring Harbor Laboratory Press, Cold Spring Harbor, N.Y., and are further illustrated in the Example section. It will be appreciated that for this purpose, a unique label or tag will often be used, such as a peptide label, a nucleic acid label, a chemical label, a fluorescent label, or a radio frequency tag, as described hereafter.

The conformation-selective binding agents in the above-described method may also be modified and/or may comprise (or can be fused to) other moieties. Examples of modifications, as well as examples of amino acid residues within the binding agent of the disclosure that can be modified (i.e., either on the protein backbone but preferably on a side chain), methods and techniques that can be used to introduce such modifications and the potential uses and advantages of such modifications will be clear to the skilled person. For example, such a modification may involve the introduction (e.g., by covalent linking or in another suitable manner) of one or more functional groups, residues or moieties into or onto the binding agent. Examples of such functional groups and of techniques for introducing them will be clear to the skilled person, and can generally comprise all functional groups and techniques mentioned in the art as well as the functional groups and techniques known per se for the modification of pharmaceutical proteins and, in particular, for the modification of antibodies or antibody fragments (including ScFvs and single domain antibodies), for which reference is made, for example, to *Remington's Pharmaceutical Sciences,* 16th ed., Mack Publishing Co., Easton, Pa. (1980). Such functional groups may, for example, be linked directly (e.g., covalently) to the binding agent, or optionally via a suitable linker or spacer, as will again be clear to the skilled person.

In the case a binding agent is of potential therapeutic value, one of the most widely used techniques for increasing the half-life and/or reducing immunogenicity of pharmaceutical proteins comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibodies and antibody fragments (including, but not limited to, (single) domain antibodies and ScFvs); reference is made to, for example, Chapman, *Nat. Biotechnol.* 54:531-545 (2002); by Veronese and Harris, *Adv. Drug Deliv. Rev.* 54:453-456 (2003), by Harris and Chess, *Nat. Rev. Drug. Discov.* 2 (2003), and in WO 04060965. Various reagents for pegylation of proteins are also commercially available, for example, from Nektar Therapeutics, USA. Preferably, site-directed pegylation is used, in particular, via a cysteine-residue (see, for example, Yang et al., *Protein Engineering* 16, 10:761-770 (2003). For example, for this purpose, PEG may be attached to a cysteine residue that naturally occurs in a binding agent, or the binding agent may be modified so as to suitably introduce one or more cysteine residues for attachment of PEG, or an amino acid sequence comprising one or more cysteine residues for attachment of PEG may be fused to the N- and/or C-terminus of a binding agent, all using techniques of protein engineering known per se to the skilled person. Preferably, for the binding agents of the disclosure, a PEG is used with a molecular weight of more than 5000, such as more than 10,000 and less than 200,000, such as less than 100,000; for example, in the range of 20,000-80,000. Another, usually less-preferred modification comprises N-linked or O-linked glycosylation, usually as part of co-translational and/or post-translational modification, depending on the host cell used for expressing the immunoglobulin single-variable domain or polypeptide of the disclosure. Another technique for increasing the half-life of a binding agent may comprise the engineering into bifunctional constructs (for example, one NANOBODY® against the target opioid receptor and one against a serum protein such as albumin) or into fusions of binding agents with peptides (for example, a peptide against a serum protein such as albumin).

A usually less-preferred modification comprises N-linked or O-linked glycosylation, usually as part of co-translational and/or post-translational modification, depending on the host cell used for expressing the selected binding agents.

Yet another modification may comprise the introduction of one or more detectable labels or other signal-generating groups or moieties, depending on the intended use of the labeled binding agent. Suitable labels and techniques for attaching, using and detecting them will be clear to the skilled person and, for example, include, but are not limited to, fluorescent labels, (such as IRDye800, VivoTag800, fluorescein, isothiocyanate, rhodamine, phycoerythrin, phycocyanin, allophycocyanin, o-phthaldehyde, and fluorescamine and fluorescent metals such as Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes, metals, metals chelates or metallic cations or other metals or metallic cations that are particularly suited for use in in vivo, in vitro or in situ diagnosis and imaging, as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase). Other suitable labels will be clear to the skilled person and, for example, include moieties that can be detected using NMR or ESR spectroscopy. Such labeled binding agents of the disclosure may, for example, be used for in vitro, in vivo or in situ assays (including immunoassays known per se such as ELISA, RIA, EIA and other "sandwich assays," etc.) as well as in vivo diagnostic and imaging purposes, depending on the choice of the specific label. As will be clear to the skilled person, another modification may involve the introduction of a chelating group, for example, to chelate one of the metals or metallic cations referred to above. Suitable chelating groups, for example, include, without limitation, 2,2',2"-(10-(2-((2,5-dioxopyrrolidin-1-yl)oxy)-2-oxoethyl)-1,4,7,10-tetraazacyclododecane-1,4,7-triyl)triacetic acid (DOTA), 2,2'-(7-(2-((2,5-dioxopyrrolidin-1-yl)oxy)-2-oxoethyl)-1,4,7-triazonane-1,4-diyl)diacetic acid (NOTA), diethyl-enetriaminepentaacetic acid (DTPA) or ethylenediaminetetraacetic acid (EDTA). Yet another modification may comprise the introduction of a functional group that is one part of a specific binding pair, such as the biotin-(strept) avidin binding pair. Such a functional group may be used to link the binding agent to another protein, polypeptide or chemical compound that is bound to the other half of the binding pair, i.e., through formation of the binding pair. For example, a binding agent of the disclosure may be conjugated to biotin, and linked to another protein, polypeptide, compound or carrier conjugated to avidin or streptavidin. For example, such a conjugated binding agent may be used as a reporter, for example, in a diagnostic system where a detectable signal-producing agent is conjugated to avidin or streptavidin. Such binding pairs may, for example, also be used to bind the binding agent of the disclosure to a carrier, including carriers suitable for pharmaceutical purposes. One non-limiting example is the liposomal formulations described by Cao and Suresh, *Journal of Drug Targeting* 8, 4:257 (2000). Such binding pairs may also be used to link a therapeutically active agent to the binding agent of the disclosure.

In the case where binding agents are modified by linking particular functional groups, residues or moieties (as described hereinabove) to the binding agent, then linker molecules will often be used. Preferred "linker molecules" or "linkers" are peptides of 1 to 200 amino acids length, and are typically, but not necessarily, chosen or designed to be unstructured and flexible. For instance, one can choose amino acids that form no particular secondary structure. Or, amino acids can be chosen so that they do not form a stable tertiary structure. Or, the amino acid linkers may form a random coil. Such linkers include, but are not limited to, synthetic peptides rich in Gly, Ser, Thr, Gln, Glu or further amino acids that are frequently associated with unstructured regions in natural proteins (Z. Dosztányi, V. Csizmok, P. Tompa, and I. Simon (2005), "IUPred: web server for the prediction of intrinsically unstructured regions of proteins based on estimated energy content," *Bioinformatics* (Oxford, England), 21(16):3433-34). Non-limiting examples of suitable linker sequences include (GS)5 (GSGSGSGSGS; SEQ ID NO:1), (GS)10 (GSGSGSGSGSGSGSGSGSGS; SEQ ID NO:2), (G4S)3 (GGGGSGGGGSGGGGS; SEQ ID NO:3), llama IgG2 hinge (AHHSEDPSSKAPKAPMA; SEQ ID NO:4) or human IgA hinge (SPSTPPTPSPSTPPAS; SEQ ID NO:5) linkers. For certain applications, it may be advantageous that the linker molecule comprises or consists of one or more particular sequence motifs. For example, a proteolytic cleavage site can be introduced into the linker molecule such that detectable label or moiety can be released. Useful cleavage sites are known in the art, and include a protease cleavage site such as Factor Xa cleavage site having the sequence IEGR (SEQ ID NO:6), the thrombin cleavage site having the sequence LVPR (SEQ ID NO:7), the enterokinase cleaving site having the sequence DDDDK (SEQ ID NO:8), or the PreScission or 3C cleavage site LEVLFQGP (SEQ ID NO:9).

Alternatively, in the case where the binding agent is linked to a detectable label or moiety using chemoenzymatic methods for protein modification, the linker moiety may exist of different chemical entities, depending on the enzymes or the synthetic chemistry that is used to produce the covalently coupled molecule in vivo or in vitro (reviewed in: Rabuka 2010*, Curr. Opin. Chem. Biol.* 14:790-796).

According to a preferred embodiment, it is particularly envisaged that the binding agents in the above method are derived from an innate or adaptive immune system. Preferably, the binding agent is derived from an immunoglobulin. Preferably, the binding agent according to the disclosure is derived from an antibody or an antibody fragment. The term "antibody" (Ab) refers generally to a polypeptide encoded by an immunoglobulin gene, or a functional fragment thereof, that specifically binds and recognizes an antigen, and is known to the person skilled in the art. An antibody is meant to include a conventional four-chain immunoglobulin, comprising two identical pairs of polypeptide chains, each pair having one "light" (about 25 kDa) and one "heavy" chain (about 50 kDa). Typically, in conventional immunoglobulins, a heavy chain variable domain (VH) and a light chain variable domain (VL) interact to form an antigen binding site. The term "antibody" is meant to include whole antibodies, including single-chain whole antibodies, and antigen-binding fragments. In some embodiments, antigen-binding fragments may be antigen-binding antibody fragments that include, but are not limited to, Fab, Fab' and F(ab')2, Fd, single-chain Fvs (scFv), single-chain antibodies, disulfide-linked Fvs (dsFv) and fragments comprising or consisting of either a VL or VH domain, and any combination of those or any other functional portion of an immunoglobulin peptide capable of binding to the target antigen. The term "antibodies" is also meant to include heavy chain antibodies, or fragments thereof, including immunoglobulin single-variable domains, as defined further herein.

The term "immunoglobulin single-variable domain" defines molecules wherein the antigen binding site is present on, and formed by, a single immunoglobulin domain (which is different from conventional immunoglobulins or their fragments, wherein typically two immunoglobulin variable domains interact to form an antigen binding site). It should, however, be clear that the term "immunoglobulin single-variable domain" does comprise fragments of conventional immunoglobulins wherein the antigen binding site is formed by a single-variable domain. Preferably, the binding agent is an immunoglobulin single-variable domain.

Generally, an immunoglobulin single-variable domain will be an amino acid sequence comprising four framework regions (FR1 to FR4) and three complementarity-determining regions (CDR1 to CDR3), preferably according to the following formula (1):

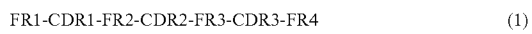
FR1-CDR1-FR2-CDR2-FR3-CDR3-FR4 (1)

or any suitable fragment thereof (which will then usually contain at least some of the amino acid residues that form at least one of the complementarity-determining regions). Immunoglobulin single-variable domains comprising four FRs and three CDRs are known to the person skilled in the art and have been described, as a non-limiting example, in Wesolowski, et al. (2009), *Med. Microbiol. Immunol.* 198: 157-174. Typical, but non-limiting, examples of immunoglobulin single-variable domains include light chain variable domain sequences (e.g., a VL domain sequence) or a suitable fragment thereof, or heavy chain variable domain sequences (e.g., a VH domain sequence or VHH domain sequence) or a suitable fragment thereof, as long as it is capable of forming a single antigen binding unit. Thus, according to a preferred embodiment, the binding agent is an immunoglobulin single-variable domain that is a light chain variable domain sequence (e.g., a VL domain sequence) or a heavy chain variable domain sequence (e.g., a VH domain sequence); more specifically, the immunoglobulin single-variable domain is a heavy chain variable domain sequence that is derived from a conventional four-chain antibody or a heavy chain variable domain sequence that is derived from a heavy chain antibody.

The immunoglobulin single-variable domain may be a domain antibody, or a single domain antibody, or a "dAB" or "dAb," or a NANOBODY® (as defined herein), or another immunoglobulin single-variable domain, or any suitable fragment of any one thereof. For a general description of single domain antibodies, reference is made to the following book: "Single domain antibodies," *Methods in Molecular Biology*, Eds. Saerens and Muyldermans, 2012, Vol 911. The immunoglobulin single-variable domains generally comprise a single amino acid chain that can be considered to comprise four "framework sequences" or "FRs" and three "complementarity-determining regions" or "CDRs" (as defined hereinbefore). It should be clear that framework regions of immunoglobulin single-variable domains may also contribute to the binding of their antigens (Desmyter et al., *J. Biol. Chem.* 2002 Jun. 28; 277(26): 23645-50; Korotkov et al., *Structure* 2009 Feb. 13; 17(2): 255-65). The delineation of the CDR sequences (and, thus, also the FR sequences) can be based on the IMGT unique numbering system for V-domains and V-like domains (Lefranc et al. 2003, *Developmental and Comparative Immunology* 27:55). Alternatively, the delineation of the FR and CDR sequences can be done by using the Kabat numbering system as applied to VHH domains from Camelids in the article of Riechmann and Muyldermans (*J. Immunol. Methods* 2000, 240:185-195).

It should be noted that the immunoglobulin single-variable domains as binding agent in their broadest sense are not limited to a specific biological source or to a specific method of preparation. The term "immunoglobulin single-variable domain" encompasses variable domains of different origin, comprising mouse, rat, rabbit, donkey, human, shark, and camelid variable domains. According to specific embodiments, the immunoglobulin single-variable domains are derived from shark antibodies (the so-called immunoglobulin new antigen receptors or IgNARs), more specifically from naturally occurring heavy chain shark antibodies, devoid of light chains, and are known as VNAR domain sequences. Preferably, the immunoglobulin single-variable domains are derived from camelid antibodies. More preferably, the immunoglobulin single-variable domains are derived from naturally occurring heavy chain camelid antibodies, devoid of light chains, and are known as VHH domain sequences or NANOBODIES®.

According to a particularly preferred embodiment, the binding agent in the above method is an immunoglobulin single-variable domain that is a NANOBODY® (as defined further herein, and including but not limited to a VHH). The term "NANOBODY®" (Nb), as used herein, is a single-domain antigen binding fragment. It particularly refers to a single-variable domain derived from naturally occurring heavy chain antibodies and is known to the person skilled in the art. NANOBODIES® are usually derived from heavy chain only antibodies (devoid of light chains) seen in camelids (Hamers-Casterman et al., *Nature* 363:446-448 (1993); Desmyter et al., *Nat. Struct. Biol.* 1996 September; 3 (9):803-11) and consequently are often referred to as VHH antibody or VHH sequence. Camelids comprise old world camelids (*Camelus bactrianus* and *Camelus dromedarius*) and new world camelids (for example, *Lama paccos, Lama glama, Lama guanicoe* and *Lama vicugna*). NANOBODY® and NANOBODIES® are registered trademarks of Ablynx NV (Belgium). For a further description of VHHs or NANOBODIES®, reference is made to the book "Single domain antibodies," *Methods in Molecular Biology*, Eds. Saerens and Muyldermans, 2012, Vol. 911, in particular, to the Chapter by Vincke and Muyldermans (2012), as well as to a non-limiting list of patent applications, which are mentioned as general background art, and include: WO 94/04678, WO 95/04079, WO 96/34103 of the Vrije Universiteit Brussel; WO 94/25591, WO 99/37681, WO 00/40968, WO 00/43507, WO 00/65057, WO 01/40310, WO 01/44301, EP 1 134 231 and WO 02/48193 of Unilever;

WO 97/49805, WO 01/21817, WO 03/035694, WO 03/054016 and WO 03/055527 of the Vlaams Instituut voor Biotechnologie (VIB); WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V., and the further published patent applications by Ablynx N.V.

As will be known by the person skilled in the art, the NANOBODIES® are particularly characterized by the presence of one or more Camelidae "hallmark residues" in one or more of the framework sequences (according to Kabat numbering), as described, for example, in WO 08/020079, on page 75, Table A-3, incorporated herein by reference). It should be noted that the NANOBODIES® of the disclosure, in their broadest sense, are not limited to a specific biological source or to a specific method of preparation. For example, NANOBODIES® can generally be obtained: (1) by isolating the VHH domain of a naturally occurring heavy chain antibody; (2) by expression of a nucleotide sequence encoding a naturally occurring VHH domain; (3) by "humanization" of a naturally occurring VHH domain or by expression of a nucleic acid encoding such a humanized VHH domain; (4) by "camelization" of a naturally occurring VH domain from any animal species and, in particular, from a mammalian species, such as from a human being, or by expression of a nucleic acid encoding such a camelized VH domain; (5) by "camelization" of a "domain antibody" or "Dab" as described in the art, or by expression of a nucleic acid encoding such a camelized VH domain; (6) by using synthetic or semi-synthetic techniques for preparing proteins, polypeptides or other amino acid sequences known per se; (7) by preparing a nucleic acid encoding a NANOBODY® using techniques for nucleic acid synthesis known per se, followed by expression of the nucleic acid thus obtained; and/or (8) by any combination of one or more of the foregoing. A further description of NANOBODIES®, including humanization and/or camelization of NANOBODIES®, can be found, e.g., in WO 08/101985 and WO 08/142164, as well as further herein.

The term "immunoglobulin single-variable domain" also encompasses variable domains that are "humanized" or camelized," in particular, NANOBODIES® that are "humanized" or "camelized." For example both "humanization" and "camelization" can be performed by providing a nucleotide sequence that encodes a naturally occurring VHH domain or VH domain, respectively, and then changing, in a manner known per se, one or more codons in the nucleotide sequence in such a way that the new nucleotide sequence encodes a "humanized" or "camelized" immunoglobulin single-variable domain of the disclosure, respectively. This nucleic acid can then be expressed in a manner known per se, so as to provide the desired immunoglobulin single-variable domains of the disclosure. Alternatively, based on the amino acid sequence of a naturally occurring VHH domain or VH domain, respectively, the amino acid sequence of the desired humanized or camelized immunoglobulin single-variable domains of the disclosure, respectively, can be designed and then synthesized de novo using techniques for peptide synthesis known per se. Also, based on the amino acid sequence or nucleotide sequence of a naturally occurring VHH domain or VH domain, respectively, a nucleotide sequence encoding the desired humanized or camelized immunoglobulin single-variable domains of the disclosure, respectively, can be designed and then synthesized de novo using techniques for nucleic acid synthesis known per se, after which the nucleic acid thus obtained can be expressed in a manner known per se, so as to provide the desired immunoglobulin single-variable domains of the disclosure. Other suitable methods and techniques for obtaining the immunoglobulin single-variable domains of the disclosure and/or nucleic acids encoding the same, starting from naturally occurring VH sequences or preferably VHH sequences, will be clear from the skilled person, and may, for example, comprise combining one or more parts of one or more naturally occurring VH sequences (such as one or more FR sequences and/or CDR sequences), one or more parts of one or more naturally occurring VHH sequences (such as one or more FR sequences or CDR sequences), and/or one or more synthetic or semi-synthetic sequences, in a suitable manner, so as to provide a NANOBODY® of the disclosure or a nucleotide sequence or nucleic acid encoding the same.

In a preferred embodiment, the binding agent as selected in the above method stabilizes a specific conformational state of a protein complex upon binding. The term "stabilizes" or "stabilizing," as used herein, is to be understood within the context of thermodynamic reaction equilibria and implies a higher binding affinity (or a preferred binding) of the binding agent for the protein complex versus a lower binding affinity (or less-preferred binding, including no binding) for its individual members. In particular, the binding agent may specifically bind to a newly formed conformational epitope that is induced or becomes more accessible upon association of the protein complex, and that is not formed by or less accessible in each of the individual members alone of the protein complex. Consequently, the binding agent will also increase the binding affinity between the individual members of the protein complex upon binding. It should be clear that the conformational epitopes selectively recognized by the binding agent as described herein can be either member protein-specific epitopes, which, for example, become more accessible upon interaction with the one or more other member proteins, or otherwise protein complex-specific epitopes, which are only formed by combining amino acid residues of the two or more constituting member proteins.

In another embodiment, the binding agent selected in the above method is further characterized in that it also stabilizes upon binding the protein complex-selective conformation of one of the constituting members in the absence of the other interacting member(s).

In specific embodiments, the selective conformation of a protein complex as described herein may be either an inactive conformation or an active conformation (or any other thermodynamically intermediary state) and depends on the type of proteins/nucleic acids involved in the interaction. For example, the conformation of a PPI is "active" when the conformation increases, opens, activates, facilitates, enhances activation, enhances binding, or upregulates a PPI's activity by at least 10% over another conformation of the PPI or over a conformation of each of the individual members of the PPI. The conformation of a PPI is "inactive" when the conformation decreases, closes, deactivates, hinders, diminishes activation, or diminishes binding, or downregulates the PPI's activity by at least 10% over another conformation of the PPI or over a conformation of each of the individual members of the PPI.

One aspect of the disclosure also relates to a composition comprising a binding agent obtained by the current method. In one embodiment, the disclosure encompasses a composition comprising a protein complex (as defined hereinbefore) and a binding agent (as described above) obtained by the current method, whereby the protein complex is stabilized in a complex conformation by the binding agent.

The binding agents identified by the methods described above have a number of applications.

For example, the binding agents identified by the methods described above may be used to purify a protein complex of interest. Suitable purification methods include, without limitation, affinity-based methods such as affinity chromatography, affinity purification, immunoprecipitation, protein detection, immunochemistry, surface-display, size exclusion chromatography, ion exchange chromatography, amongst others, and are all well known in the art.

Also, binding agents that are specific for a protein complex conformation can be used as co-crystallization aid, or in other words, can be used to facilitate crystallogenesis of a transient protein complex, using any of a variety of crystallization methods. For example, in case a membrane protein forms part of a protein complex, crystallization methods as reviewed in Caffrey (2003), *J. Struct. Biol.* 142:108-32 and Caffrey et al., *Nat. Protoc.* 4:706-731, (2009) may be preferred. In general terms, the methods are lipid-based methods that include adding lipid to the complex prior to crystallization. Many of these methods, including the lipidic cubic phase crystallization method and the bicelle crystallization method, exploit the spontaneous self-assembling properties of lipids and detergent as vesicles (vesicle-fusion method), discoidal micelles (bicelle method), and liquid crystals or mesophases (in meso or cubic-phase method). Lipidic cubic phases crystallization methods are described in, for example: Landau et al., *Proc. Natl. Acad. Sci.* 1996 93:14532-5; Gouaux, *Structure* 1998, 6:5-10; Rummel et al., *J. Struct. Biol.* 1998, 121:82-91; Nollert et al., *Methods* 2004 34:348-53; Rasmussen et al. (2011) *Nature* 469:175-180, which publications are incorporated by reference for disclosure of those methods. Bicelle crystallization methods are described in, for example: Faham et al., *Protein Sci.* 2005 14:836-40; Faham et al., *J. Mol. Biol.* 2002 Feb. 8, 316(1):1-6, which publications are incorporated by reference for disclosure of those methods. Crystallization methods for soluble proteins are known in the art, and are described, for example, by E. F. Garman.[17]

Further, the binding agents identified by the methods described above may also be used in compound screening methods, for example, to identify compounds that specifically bind a protein complex in a particular conformation and/or that induce or enhance the association of a protein complex in a particular conformation upon binding, or alternatively, to identify compounds that disrupt a protein complex in a conformation-selective manner. Such compounds can have a therapeutic benefit, for instance, if the compound is able to activate or increase protein complex-mediated signaling or prolong the duration of the protein complex-mediated signaling or alternatively decrease or inhibit protein complex-mediated signaling, depending on the disease indication.

Further, the binding agents identified by the methods described above may also be used as a diagnostic tool to detect and/or capture a protein complex that is characteristic of a given disease in a patient sample.

Further, the binding agents identified by the methods described above may also be used as a research tool, for example, to detect or visualize a protein complex in a sample. In particular, it will be appreciated that the binding agents may be particularly useful tools for the development or improvement of cell-based assays. Cell-based assays are critical for assessing the mechanism of action of new biological targets and biological activity of chemical compounds, for example, cell-based assays for measurement of protein complex pathway (in)activation; measurement of protein trafficking by tagging one or more member(s) of a protein complex with a fluorescent protein; direct measures of interactions between proteins using Fluorescence resonance energy transfer (FRET), bioluminescence resonance energy transfer (BRET) or yeast two-hybrid approaches. Also relevant to the disclosure, binding agents may be key building blocks of (intracellular) conformational biosensors for proteins or protein complexes inside a cell.[18]

The following examples are intended to promote a further understanding of the disclosure. While the disclosure is described herein with reference to illustrated embodiments, it should be understood that the disclosure is not limited hereto. Those having ordinary skill in the art and access to the teachings herein will recognize additional modifications and embodiments within the scope thereof. Therefore, the disclosure is limited only by the claims contained herein.

EXAMPLES

Part 1. Binding Agents for the Stabilization of Transient Protein-Protein Interactions General Description of the Method It was shown that cross-linking a transient protein complex, followed by immunization of llama's with this complex, followed by display of the in vivo-matured antibody repertoire, and followed by co-selection, delivers NANOBODIES® with the unique property to bind conformational epitopes on transient protein complexes that are not represented on the constituting monomers.

Step 1: Cross-Link Association Proteins and Immunize Llamas for the Generation of Nbs that Bind Conformational Features of the Complex a) Chemical Cross-Linking of the Interacting Monomers.

In principle, animals could be immunized with mixtures of the interacting monomers. However, considering the short half-life of transient PPIs (0.1 to 1 second), stabilizing these transient complexes by chemical cross-linking is envisaged. In this way, animals can be immunized with antigens that are in a covalent association that is very similar to the native transient complex to trigger and mature immunoglobulins that bind allosteric conformational epitopes of the transient complex.

Method:

Over the last decades, various cross-linking strategies have been used to preserve labile protein-protein interactions in stable macromolecular assemblies.[10] As an example, a cocktail of highly efficient bifunctional reagents[11] containing diverse reactive groups that can react with amines or carboxylic acids are used (World Wide Web at covalx.com). These reagents were found to be effective in cross-linking a wide range of interacting proteins in native-like covalent complexes under physiological conditions.

b) Generation of In Vivo Matured Conformational NANOBODIES® by Immunization.

Although naive or synthetic libraries of antibodies may contain conformational binders against protein-protein complexes, a preferred method is to immunize llamas with the (optionally cross-linked) protein-protein complex to expose their immune system with the conformational epitopes that are unique to the (transient) complex. The NANOBODY® platform has the competitive advantage over other recombinant scaffold libraries in that large numbers ($10^9$) of fragments harboring the full antigen-binding capacity of genuine in vivo-matured antibodies can be screened for high-affinity binders in a couple of days, allowing one to fully exploit the humoral response of large mammals against native antigens.[12, 13]

Method:

A llama is immunized with a cross-linked complex of interacting proteins, prepared as described above (of note, free partners can also be present in the sample). The antigen is diluted in an antigen-compatible buffer (ag-buffer) and equal volumes of the cross-linked antigen and Gerbu adjuvant are mixed via up-and-down pipetting. Once a stable emulsion is obtained, this preparation can be injected into llamas following a standard immunization scheme as described in Table 1.[14]

TABLE 1

| Immunization scheme with cross-linked antigens | | |
|---|---|---|
| Day | Llama injection | Tissue collection |
| Day 0 | 200 μg antigen + 0 μl Ag buffer + 600 μl Gerbu | 10 ml pre-immune blood |
| Day 14 | 100 μg antigen + 100 μl Ag buffer + 400 μl Gerbu | |
| Day 21 | 100 μg antigen + 100 μl Ag buffer + 400 μl Gerbu | |
| Day 28 | 100 μg antigen + 100 μl Ag buffer + 400 μl Gerbu | 10 ml immune blood |
| Day 35 | 100 μg antigen + 100 μl Ag buffer + 400 μl Gerbu | |
| Day 42 | 100 μg antigen + 100 μl Ag buffer + 400 μl Gerbu | |
| Day 45 | | 100 ml immune blood |

Blood is collected from the immunized animal at days 28 and 42 and the humoral immune response is evaluated by ELISA.[14] 100 μg of a 1-μg/ml solution of the cross-linked complex was coated on a Maxisorp plate. Serial dilutions of the pre-immune (day 0) and immune (day 28) sera are added to the coated wells. Bound llama immunoglobulins are detected using anti-llama IgG antibody-conjugated horse radish peroxidase conjugate (Imtec) using a colorimetric assay based on the ABTS substrate (Sigma).

Step 2: Display and Co-Selection Method for Nbs that Selectively Bind the Transient Complexes or Nbs that Selectively Bind the Separate Interacting Monomers Immunizations of llamas with cross-linked complexes (step 1) inevitably generate different classes of NANOBODIES®: Nbs that bind to protomers only, binders that recognize a protomer and the complex with similar affinity, and antibodies that selectively bind to the complex. The second technological challenge is to combine this first step with highly efficient selection methods that can discriminate Nbs that exclusively bind the transient (non-cross-linked) complex from Nbs that bind to the dissociated monomers.

a) Display Immune Library on Yeast Cells.

As an example, the multivalent display of NANOBODIES® on yeast cells in combination with the resolving power of fluorescent-activated cell sorting (FACS) was exploited. In yeast display, each Nb is displayed as a fusion to the Aga2p protein at about 50,000 copies on the surface of an individual yeast cell.[15] For co-selection by FACS, the protomers that associate in a transient PPI separately with different fluorescent dyes were labeled. Next, the Nb-displaying yeast library can be stained with a mixture of these fluorescent protomers. FACS can then be used to analyze the properties of each Nb that is displayed on a particular yeast cell and to recover particular populations as illustrated in FIG. 2. When two proteins A and B are separately fluorescently labeled with a different dye, a two-color FACS analysis will discriminate populations of (1) yeast cells displaying aspecific binders, (2) yeast cells displaying Nbs that only bind A, (3) yeast cells displaying Nbs that only bind B, and (4) yeast cells displaying Nbs that specifically bind the complex AB (FIG. 2).

Method:

A blood sample of 100 ml of an immunized llama contains sufficient expressing B-cells to clone the full diversity of the in vivo-matured NANOBODIES® with high specificity for their cognate antigen. Therefore, 100 ml of fresh anti-coagulated blood is collected from the immunized animal (day 45) and peripheral blood lymphocytes are purified as described.[14]

Total RNA is extracted from the purified peripheral blood lymphocytes following the instructions provided with the RNEASY® extraction kit (Qiagen). Next, double-stranded cDNA is synthesized by reverse transcription of 50 μg of total RNA using the SUPERSCRIPT®III First-Strand cDNA kit (Invitrogen) and random hexanucleotides.

To amplify all immunoglobulin heavy chains from the cDNA, forward primer CALL001 and reverse primer CALL002 are used in a first PCR reaction.[14] The NANOBODY® encoding DNA fragments are separated from the variable domain of the heavy chain of the conventional antibody repertoire via gel electrophoresis. The appropriate DNA-band is purified from the gel using a QIAQuicK® gel extraction kit and further amplified using a second nested PCR. This second PCR with nested primers GAPVHH5_fw and GAPVHH3_rv annealing at framework 1 and framework 4, respectively, amplifies NANOBODY®-encoding genes as Nhel-BamHI fragments. Primers GAPVHH5_fw and GAPVHH3_rv create two 30 bp overlaps with the pCTCON2 yeast display vector[15] to allow GAP repair cloning via homologues recombination in yeast.

| | |
|---|---|
| CALL001 | 5' GTC CTG GCT GCT CTT CTA CAA GG 3' (SEQ ID NO: 10) |
| CALL002 | 5' GGT ACG TGC TGT TGA ACT GTT CC 3' (SEQ ID NO: 11) |
| GAPVHH5_fw | 5' CGG TAG CGG AGG CGG AGG GTC GGC TAG CCA GGT GCA GCT GGT GGA GTC TGG GG 3' (SEQ ID NO: 12) |
| GAPVHH3_rv | 5' GGG ACC CAG GTC ACC GTC TCC AGC GGA TCC GAA CAA AAG CTT ATT TCT GAA G-3' (SEQ ID NO: 13) |

The display vector pCTCON2 allows the expression of the NANOBODY® as a fusion protein at the C-terminus of the Aga2p on the cell surface of yeast. The expression of this construct is under control of a galactose-induced promotor and results in 50,000 copies per yeast cell. For GAP repair cloning, 10 μg of the amplified NANOBODY® repertoire is mixed with 10 μg of Nhel-BamHI (Fermentas) digested pCTCON2 and co-transformed in electrocompetent EBY100 yeast cells. Homologous recombination in EBY100 yeast cells results in the insertion of the full NANOBODY® repertoire into the linearized pCTCON2 vector with a diversity of 1×E6 to 1×E7 transformants and an insert rate up to 100%. The presence of an N-terminal HA-tag and a C-terminal myc-tag on the displayed NANOBODY® allows monitoring NANOBODY® expression on each individual yeast cell in FACS by use of fluorescently labeled antibodies that bind HA or myc.

b) Fluorescent Labeling of Individual Protein Partners.

Essential to this disclosure is the distinctive labeling of at least one of the partners, for example, with specific fluorescent dyes that can be detected in FACS. This can be achieved by recombinant expression of the protein with a fluorescent tag (GFP, YFP). Proteins can also be indirectly labeled by incubating with a fluorescent Ab conjugate/cascade directed against a tag or the protein itself. The method applied in this example is random covalent coupling of fluorescent dyes (ALEXA FLUOR®, DYLIGHT®) to amine or cysteine reactive groups of the protein. If possible, the effect of any type of labeling on the protein-protein interaction should be checked in advance, since labeling could be interfering with complex formation. If this is the case, an alternative labeling method would be advisable.

c) Yeast Display and Co-Selection by FACS.

FACS can be used simultaneously (1) to analyze the properties of each NANOBODY® that is displayed multivalently on an individual yeast cell and (2) to selectively recover yeast cells displaying Nbs with a particular property (FIG. 2). Yeast cells displaying NANOBODIES® that selectively bind A but not B or AB can be enriched if cells of the top-left quadrant are recovered by FACS. Yeast cells displaying NANOBODIES® that selectively bind B but not A or AB can be enriched if cells of the bottom-right quadrant are recovered by FACS. Yeast cells displaying NANOBODIES® that selectively bind the AB complex but not to A alone or B alone can be enriched if cells of the top-right quadrant are recovered by FACS. These processes can be repeated in several rounds to enrich for yeast cells displaying NANOBODIES® with the desired characteristics.

Method:

For a first selection round by yeast display, a sufficiently large aliquot of the library is thawed (number of yeast cells >10× the library diversity) and inoculated in fresh SDCAA 1:100 pen/strep medium according to Chao et al.[15] Yeast cells are induced with galactose for Nb expression in SGCAA medium for a minimum of 16 hours and $1\times10^8$ cells are harvested by centrifugation. Induced yeast cells are washed three times by centrifugation with Ag-buffer supplemented with 2% BSA to block aspecific binding sites on the yeast surface. From this point on, samples are kept at 4° C. during further manipulations to minimize the dissociation of the detection antibodies and labeled proteins from the yeast displayed NANOBODIES®. To monitor the expression level of the displayed Nb on each cell during FACS, the yeast cells were subsequently incubated with 1 ml Ag buffer supplemented with 1:100 anti c-myc mouse monoclonal antibody (Roche) for 30 minutes, washed three times by centrifugation, and subsequently labeled with 1 ml 1:100 R-Phycoerythrin goat anti-mouse antibody (Lucron) for 30 minutes. In parallel with these labeling steps, the separately labeled proteins are mixed at such a concentration (1-100 μM) that at least a small fraction of transient complex will be formed after 1 hour of incubation. Next, the labeled yeast cells are washed and resuspended in 1 ml of this mixture of labeled proteins. During 1 hour incubation, a fraction of the displayed NANOBODIES® will specifically bind the double-labeled transient complex or the constituting single-labeled proteins. To remove excess amounts of unbound labeled proteins, yeast cells are washed three times by centrifugation with Ag-buffer supplemented with 0.2% BSA.

All selection rounds are performed using three-color Fluorescence-Activated Cell Sorting (FACS) on a FACS AriaIII (BD Biosciences). FIG. 4 provides an illustrative example of the stepwise enrichment for yeast cells that express NANOBODIES® that selectively bind to complex AB, but not to A or B separately. Typically, 0.1% to 10% of the yeast cells contained in the top-right quadrant, corresponding to yeast cells that bind significant amounts of both of the separately labeled proteins constituting the (transient) complex, are sorted and collected by FACS in 500 μl 2×SDCAA 1:100 pen/strep medium. Sorted yeast cells are plated out for single colonies on SDCAA 1:100 pen/strep agar plates and incubated for 3 days at 30° C. This sub-library is scraped, cultured in liquid SDCAA 1:100 pen/strep and induced with SGCAA 1:100 pen/strep for the next selection round.

After a few rounds of selection, single yeast colonies are picked from the enriched FACS outputs. These clones are cultured in 1 ml SDCAA 1:100 pen/strep medium and a 96-well masterplate for long-term storage is produced by adding 30% glycerol. From the same culture, VHH genes are amplified via PCR and the sequence of these fragments is determined using pCTCON_fw and pCTCON2_rv as the sequencing primers.[15]

```
pCTCON2_fw
                                  (SEQ ID NO: 14)
5' GTTCCAGACTACGCTCTGCAGG 3'

pCTCON2_rv
                                  (SEQ ID NO: 15)
5' GATTTTGTTACATCTACACTGTTG 3'
```

Step 3: Analysis of the Binding Properties of Single NANOBODIES® by FACS

Yeast cells deriving from a single colony all express the same NANOBODY® and FACS on a culture of these cells can easily be used to analyze the binding properties of the NANOBODY® that is expressed according to the same principles that are illustrated in FIG. 2.

Based on sequence analysis families of all clones contained in the master plate, NANOBODY® sequences can be grouped in sequence families of related NANOBODIES®.[14] Based on such analysis, individual clones were selected for individual analysis by FACS.

Method:

Each selected clone is grown ON at 30° C. and 200 rpm in 96 deepwell plates containing 1 ml SDCAA 1:100 pen/strep. NANOBODY® expression is induced with SGCAA 1:100 pen/strep medium for 16 hours at 30° C. and 200 rpm.

In total, $2\times10^6$ cells are harvested and washed by centrifugation with Ag buffer complemented with 2% BSA. To monitor the expression level of the displayed Nb on each cell during FACS, the yeast cells are subsequently incubated with 1 ml of Ag buffer complemented with 1:100 anti-c-myc mouse monoclonal antibody (Roche) for 30 minutes, washed three times by centrifugation, and subsequently labeled with 1 ml 1:100 R-Phycoerythrin goat anti-mouse antibody (Lucron) for 30 minutes. Yeast cells are then incubated for 1 hour with mixtures of separately labeled proteins constituting the (transient) complex. To remove excess amounts of the labeled proteins, yeast cells were washed three times with Ag buffer supplemented with 0.2% BSA. Stained cells are subsequently analyzed by FACS according to FIG. 2 to assess if the NANOBODY® under investigation is (1) aspecific for the antigen, (2) binds selectively to A but not to B or AB, (3) binds selectively to B but not to A or AB, and (4) binds selectively to AB but not to A alone or B alone. It should be noted that not all NANOBODIES® fall into these distinct types. Rather, there is a continuum between NANOBODIES® that exclusively bind to AB, to A or to B and NANOBODIES® that bind stronger to AB compared to A or B, and NANOBODIES® that bind stronger to A or B compared to AB.

Step 4: Expression of Selected NANOBODIES® in *E. coli* and Purification by IMAC For periplasmic expression in *E. coli*, individual NANOBODY® sequences were subcloned in a pMESy4 vector[14] containing a pelB signal for periplasmic expression and an ampicillin resistance gene. The C-terminal HA and N-terminal $(His)_6$EPEA tag allows efficient purification via affinity chromatography and detection in ELISA with appropriate antibodies.[24]

Method:

The yeast plasmid is recovered from an ON culture using the Zymoprep kit. NANOBODY® genes are amplified by PCR as PstI-BSTEII fragments using VHH_for and VHH_back as primers. The VHH fragments are digested with PstI and BstEII restriction enzymes (Fermentas) and ligated into the linearized pMESy4 vector with complementary ends. Ligation products are transformed in electrocompetent WK6 cells and single colonies are picked.

```
VHH_for
                                    (SEQ ID NO: 16)
5' GAT GTG CAG CTG CAG_GAG TCT GGR GGA GG 3'

VHH_back
                                    (SEQ ID NO: 17)
5' GGA CTA GTG CGG CCG CTG GAG ACG GTG ACC TGG

GT 3'
```

NANOBODIES® are purified from the periplasm of *E. coli* by IMAC according to Pardon et al.[14]

Example 1

In order to identify NANOBODIES® that stabilize and selectively bind to a transient protein complex, the RIC8A/Gαi1 complex was chosen as a model system.

Heterotrimeric G protein alpha subunits (Gα) are activated upon exchange of GDP for GTP at the nucleotide binding site of Gα, catalyzed by guanine nucleotide exchange factors (GEFs). In addition to transmembrane G protein-coupled receptors (GPCRs), which act on G protein heterotrimers, members of the family cytosolic proteins typified by mammalian RIC8A (resistance to inhibitors of cholinesterase 8A) are GEFs for Gi/q/12/13-class Gα subunits. RIC8A binds to Gα-GDP, resulting in the release of GDP. The RIC8A complex with nucleotide-free Gαi1 is stable, but dissociates upon binding of GTP to Gαi1.

As members of the Ras superfamily of regulatory GTP binding proteins, heterotrimeric G protein alpha subunits (Gα) undergo cycles of activation and deactivation driven by binding and hydrolysis of GTP.[16] Conversion to the basal, inactive state results from the intrinsic GTP hydrolyase activity of the G protein. Reactivation is achieved by replacement of GDP by GTP at the nucleotide-binding site, catalyzed by guanine nucleotide exchange factors (GEFs). Although the structural events that accompany GEF catalyzed nucleotide exchange on Ras-like G proteins are relatively well understood,[17] the mechanism of heterotrimeric G protein activation remains enigmatic. Agonist-activated, transmembrane G protein-coupled receptors (GPCRs)[18] are the best characterized heterotrimeric G protein GEFs. GPCRs act on plasma membrane-localized G protein heterotrimers that consist of GDP-bound Gα tightly associated with heterodimers of Gβ and Gγ subunits. Members of a family of predominantly cytosolic proteins, typified by mammalian RIC8A, identified as non-receptor GEFs, catalyze nucleotide exchange directly on Gα subunits of the Gi/o/q/12/13 families.[19] Across phylogeny, RIC8A paralogs act in GPCR-independent pathways to orient mitotic spindles in asymmetric cell division, as demonstrated in *C. elegans*,[20, 21] *Drosophila*,[22] and mammalian cells.[24]

a) Preparation of a Protein Complex as Immunogen for Camelid Immunization

Recombinant rat RIC8A (uniprot:Q80ZG1) and Gαi1 (uniprot:P10824) were produced and purified as described previously.[24] The (non-covalent) complex was purified by a size exclusion chromatography in an amine-free buffer (20 mM PBS buffer pH 6.8 without DTT). The chemical cross-linking reaction was performed using K100 reagent purchased from Covalx (World Wide Web at covalx.com/).[11] Ten μM of the complex in 20 mM PBS buffer pH 6.8 was incubated with 10 μl of 2 mg/ml of K100 cross-linker for 5 and 30 minutes at room temperature. Removal of the unreacted cross-linker species was done using a 1-ml HITRAP® desalting matrix (GE Healthcare). The presence of the cross-linked complex (100 kDa) was monitored by SDS/PAGE (FIG. 3). In fact, this was still a non-homogeneous mixture containing free RIC8a (50 kDa) and Gαi1 (37 kDa).

b) Induction of an Antibody-Mediated Immune Response in Llama Against the Cross-Linked RIC8A/Gαi1 Complex This preparation of the cross-linked (30 minutes) RIC8A-Gαi1 complex was diluted into 20 mM PBS pH 7.4 with 1 mM DTT and injected into a llama according to step 1 of the general method. A clear antigen-specific signal was detected, as the ELISA signals of the immune serum (day 28) were minimally two-fold higher than those obtained with the pre-immune serum.

c) Fluorescent Labeling of RIC8A and Gαi1

Purified recombinant RIC8A and Gαi1 were dialyzed extensively against 20 mM PBS pH 7.4 with 1 mM DTT prior to the separate labeling reactions. RIC8A was incubated with a five-fold excess of DYLIGHT®-405 NHS Ester (Pierce, Thermo Scientific) according to the manufacturer's instructions. Gαi1 was incubated with a five-fold excess of DYLIGHT®-488 NHS Ester (Pierce, Thermo Scientific).

The labeling reaction was performed at room temperature in the dark for 30 minutes. Unreacted dye was removed by size exclusion using a NAPS column (GE Healthcare). Labeling was checked by SDS-PAGE and visualization of the fluorescent protein was performed using a Biorad gel imager.

d) Yeast Display and Co-Selection of NANOBODIES® that Selectively Bind RIC8A•Gαi1 Complex but not to RIC8A or Gαi1 Alone Aiming at stabilizing the RIC8A•Gαi1 complex for further biophysical/biochemical investigation of this complex, NANOBODIES® were selected that selectively bind the RIC8A•Gαi1 complex but not to RIC8A or Gαi1 by FACS according to the principle that is illustrated in FIG. 2. For the first selection round, the yeast display library was diluted in 1 ml 20 mM PBS pH 7.4, 150 mM NaCl, 2 mM DTT supplemented with 10 μM of separately labeled RIC8A DYLIGHT®-405 and 10 μM of separately labeled Gαi1 DYLIGHT®-488. Before adding the yeast cells, the complex was allowed to form by mixing equimolar amounts of RIC8A DYLIGHT®-405 and Gαi1 DYLIGHT®-488 and incubating 1 hour at RT. At 10 μM, there will be a mixture of free RIC88A DYLIGHT®-405, free Gαi1 DYLIGHT®-488 and RIC8A DYLIGHT®-405/Gαi1 DYLIGHT®-488 complex, since the Kd of this PPI is around 12 μM in the presence of GDP.[24] To enrich yeast cells displaying NANOBODIES® that selectively bind the RIC8A•Gαi1 complex but not to RIC8A or Gαi1 alone, the following sorting gates were applied in a three-color FACS experiment (R-Phycoerythrin, DYLIGHT®-405 and DYLIGHT®-488). High R-Phycoerythrin fluorescence indicates that the yeast cell expresses a NANOBODY® on its surface. High DYLIGHT®-405 fluorescence indicates that the displayed NANOBODY® traps RIC8A and high DYLIGHT®-488 fluorescence indicates that the NANOBODY® traps. Yeast cells scoring on three colors express a NANOBODY® that binds the RIC8A•Gαi1 complex but not to RIC8A or Gαi1 alone. In a first round of selection (see FIG. 4), about 0.1-1% of triple-positive cells (binding RIC8A•Gαi1, Q2) were sorted and yeast clones expressing aspecific NANOBODIES® (Q4) or NANOBODIES® that bind RIC8A only (Q1) or NANOBODIES® that bind Gαi1 only (Q3) were discarded.

To obtain NANOBODIES® that bind the RIC8A•Gαi1 complex only, two more rounds of co-selection by FACS were performed to stepwise enrich the top 0.1%-0.5% fraction of yeast cells with the highest fluorescence of DYLIGHT®-405 and DYLIGHT®-488. In the second and third FACS selection, the number of stained cells to be sorted by FACS was lowered to $1\times10^7$ and $5\times10^6$ cells, respectively, and the staining volume was lowered accordingly to 500 μl and 200 μl. The concentration of separately labeled RIC8A DYLIGHT®-405 and Gαi1 DYLIGHT®-488 complex was kept constant at 10 μM. In round 2, about 0.3% of the best scoring cells were collected (P3 in FIG. 4). In the third round, the best scoring yeast cells were collected in two pools (FIG. 4). P3 contains all yeast cells with a high fluorescence in the DYLIGHT®-405 channel and the Gαi1 DYLIGHT® channel; P4 contains the 0.5 best scoring fraction of these cells.

Results

FIG. 4 illustrates that three rounds of co-selection by FACS enriches for yeast cells that display NANOBODIES® (positive signal in the R-Phycoerythrin channel) and show increasing fluorescence of DYLIGHT®-405 (coupled to RICE) and DYLIGHT®-488 (coupled to Gαi1). Remarkably, yeast cells with a high signal in the DYLIGHT®-405 channel only or the DYLIGHT®-488 channel only did not enrich after three rounds of selection indicating that co-selection by FACS is a powerful method to select NANOBODIES® that bind the RIC8A•Gαi1 complex but not to RIC8A or Gαi1 alone.

To further characterize the NANOBODIES® that were obtained by co-selection by FACS, the sequence was determined for 100 clones recovered from round 2 (P3 in FIG. 4) and 100 clones recovered from round 3 (P3 and P4).

Sequence alignment of all these clones shows that the selected NANOBODIES® belong to 21 different sequence families only (characterized by differences in CDR3 loop[14]). Representative sequences of the 15 largest sequence families are aligned in FIG. 5. The large occurrence (Table 2) of some families provides confidence that enriched binders are binding to the complex rather than just aspecific binders.

TABLE 2

| CA pCTCON2 *S. cerevisiae* | CA pMESy4 *E. coli* | Family | Occurrence | CDR3 Sequence |
|---|---|---|---|---|
| CA8312 | CA8328 | 1 | 21 | CAGDRQPYVYDLPTAQYQYDY (SEQ ID NO: 18) |
| CA8411 | CA8435 | 3 | 40 | CASSSIEFGPLEDTYDY (SEQ ID NO: 19) |
| CA8314 | CA8330 | 4 | 2 | CAAEAREFSVGSYYATEYDY (SEQ ID NO: 20) |
| CA8315 | CA8331 | 5 | 14 | CAADRKPYSYYPSDFGSW (SEQ ID NO: 21) |
| CA8316 | CA8332 | 7 | 11 | CAATPADSAFMRNLRVYDY (SEQ ID NO: 22) |
| CA8318 | CA8334 | 8 | 8 | CVARVGSPSSSDRAYQY (SEQ ID NO: 23) |
| CA8319 | CA8335 | 10 | 34 | CAATRRDFYIIRNSRPQFDY (SEQ ID NO: 24) |
| CA8322 | CA8338 | 16 | 4 | CARCPAGAACKVEYDY (SEQ ID NO: 25) |
| CA8402 | CA8431 | 19 | 6 | CAATPADLTVVAGPPRIEMWY (SEQ ID NO: 26) |
| CA8403 | CA8432 | 20 | 3 | CAATAADYVLRSRPSVYSY (SEQ ID NO: 27) |
| CA8405 | CA8433 | 21 | 3 | CAAAIRDGHNYYASDMRRYDY (SEQ ID NO: 28) |
| CA8418 | | 23 | 6 | ASDRRPYRYNIGTAEGEYNY (SEQ ID NO: 29) |
| CA8419 | | 24 | 4 | GKGWFLNRRDES (SEQ ID NO: 30) |
| CA8421 | | 26 | 2 | AADRVPYRFGVPSINEYDY (SEQ ID NO: 31) |
| CA8424 | CA8444 | 29 | 2 | NFNVRYYGEY (SEQ ID NO: 32) |

e) Yeast Display and Co-Selection of NANOBODIES® that Selectively Bind to RIC8A or Gαi1 Alone but not to the RIC8A•Gαi1 Complex So far, focus was only on binders that selectively bind to (transient) protein complexes but not to the constituting monomers because such binders will stabilize the complex. NANOBODIES® that only bind to one of the constituting monomers but not to the protein complex are equally important in other biochemical, biophysical or therapeutic applications because such NANOBODIES® will disrupt a (transient) protein-protein complex.

Selection of binders that recognize only one partner instead of the complex but do not bind the complex were selected in a similar manner as described in the previous section with the following modifications. In the first round (FIG. 6), NANOBODY®-expressing yeast cells were sorted that exclusively bind to RIC8A DYLIGHT®-405 (Q1). Cells binding the complex (Q2), the other partner Gαi1 DYLIGHT®-488 (Q3) and cells that display aspecific binders (Q4) were discharged. In the following round 2, the induced yeast sub-library was incubated with 100 μl of 1 μM free Ric-8A DYLIGHT®-405.

Results

Figure 7:
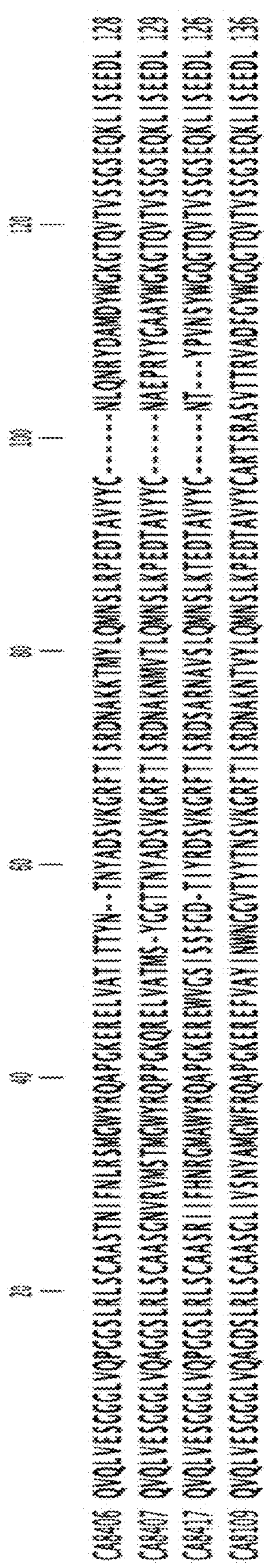
FIG. 7. AA sequence alignment (CLC viewer) of NANOBODIES® resulting from the selection for RIC8A binders (SEQ ID NOS:66-69.
Figure 8E:
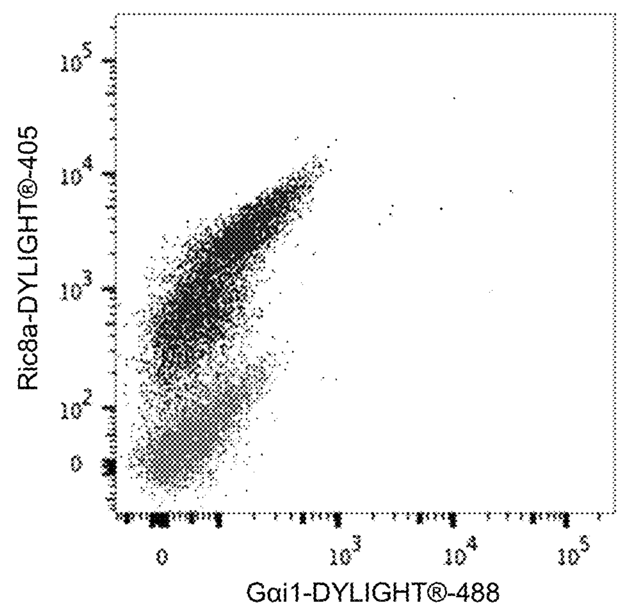

FIG. 6 nicely illustrates that two rounds of co-selection by FACS enrich for yeast cells with a high signal in the DYLIGHT®-405 channel only. From the selection output of round 3 (P3 and P4), 100 clones were sequenced and aligned (FIG. 7). All clones belong to four sequence families only, two of which with very high occurrence (Table 3). These NANOBODIES® have completely different sequences in the CDR3 loop compared to the ones found that bind the RIC8A•Gαi complex (Table 2).

TABLE 3

| CA pCTCON2 *S. cerevisiae* | CA pMESy4 *E. coli* | Family | Occurrence | CDR3 Sequence |
|---|---|---|---|---|
| CA8408 | CA8109 | 6 | 3 | ARTSRASVTTRVADFGY (SEQ ID NO: 33) |
| CA8406 | | 11 | 13 | NLQNRYDAMDY (SEQ ID NO: 34) |
| CA8417 | CA8440 | 13 | 30 | NTYPVNSY (SEQ ID NO: 35) |
| CA8407 | | 22 | 3 | NAEPRYYGAAYL (SEQ ID NO: 36) |

f) Characterization of NANOBODIES® by FACS Screening

To identify if it was indeed selected for Ric-8A•Gαi1 specific complex binders in paragraph d and for RIC8A only binders in paragraph e, a FACS screening assay was performed on single yeast clones. Screening for NANOBODY® binding was performed in 20 mM PBS pH 7.4, 150 mM NaCl, 2 mM DTT, 0.2% BSA buffer on the following target proteins: 1 μM RIC8A DYLIGHT®-405, 1 μM Gαi1 DYLIGHT®-488, and 1 μM complex RIC8A DYLIGHT®-405•Gαi1 DYLIGHT®-488.

Results

This screening method allowed characterization of the NANOBODIES® and distinguishing between three interaction profiles (FIGS. 8A-8E):

Type 1: NANOBODIES® that specifically bind the Ric-8A•Gαi1 complex and not the individual partners. At this concentration (1 μM of individual partners) the complex is not fully formed, so the fact that double-stained yeast cells could be detected indicates that these NANOBODIES® act as complex stabilizers. Also, this NANOBODY® specifically recognizes an epitope that is only present in the RIC8A•Gαi1 complex. This can be explained by the availability of new epitopes formed by the binding interface or due to conformational changes in the interaction partners upon binding.

Type 2: NANOBODIES® that interact with the complex if the sample is incubated with a RIC8A DYLIGHT®-405-Gαi1 DYLIGHT®-488 mixture. In addition this NANOBODY® binds as well with one of the free partners if incubated with a single Ag. This means that the NANOBODY® can bind an epitope that is present in the free partner and in the complex.

Type 3: NANOBODIES® that show a preferable binding to the individual partner RIC8A even if the RIC8A DYLIGHT®-405-Gαi1 DYLIGHT®-488 complex is presented. They also show a high binding toward the single partner in solution. This implies that upon NANOBODY® binding, the complex cannot be formed.

Results from this screening are summarized (Table 4) and show that clones coming from the sort for RIC8•Gαi1 complex binders result in enrichment for type 1 and type 2 binders. This is in contrast with the output clones from the RIC8A selection method where only type 3 binders were selected.

TABLE 4

| CA pCTCON2 *S. cerevisiae* | CA pMESy4 *E. coli* | Ric8A | Gαi1 | Ric8A-Gαi1 | Type |
|---|---|---|---|---|---|
| CA8312 | CA8328 | no | no | yes | 1 |
| CA8411 | CA8437 | yes | no | yes | 2 |
| CA8314 | CA8330 | no | no | yes | 1 |
| CA8315 | CA8331 | no | no | yes | 1 |
| CA8316 | CA8332 | no | no | yes | 1 |
| CA8318 | CA8334 | no | no | yes | 1 |
| CA8319 | CA8336 | no | no | yes | 1 |
| CA8322 | CA8338 | yes | no | yes | 2 |
| CA8402 | CA8431 | no | no | yes | 1 |
| CA8403 | CA8432 | no | no | yes | 1 |
| CA8405 | CA8433 | no | no | yes | 1 |
| CA8418 | | yes | no | yes | 2 |
| CA8419 | | yes | no | yes | 2 |
| CA8421 | | yes | no | yes | 2 |
| CA8424 | CA8444 | yes | no | yes | 2 |
| CA8408 | CA8109 | yes | no | free | 3 |
| CA8406 | | yes | no | free | 3 |
| CA8417 | CA8440 | yes | no | free | 3 |
| CA8407 | | yes | no | free | 3 |

g) Biophysical Characterization of NANOBODIES® that Bind to RIC8A•Gαi1 but not to RIC8A Alone or Gαi1 Alone A representative Nb that binds to RIC8A•Gαi1 complex but not to RIC8A alone or Gαi1 alone (CA8332) was further characterized by biolayer interferometry (BLI) using an Octet Red96 (ForteBio, Menlo Park, Calif., USA). Forty μg/ml of the purified NANOBODY® was immobilized through the C-terminal Histag on a NiNTA-coated biosensor (part No. 18-5102). Immobilization was performed in the binding buffer (10 mM Tris pH 8.5, 150 mM, 1 mM DTT, 0.2 mg/ml BSA) shaken for 900 seconds at 1K RPM. This step is enough to saturate the biosensor with the NANOBODY®. Then, the tips are washed for 600 seconds at 1.2K RPM in the binding buffer. Next, a baseline is measured for 600 seconds at 1K RPM in a well containing the binding buffer. The association kinetics of the different analytes with the immobilized NANOBODY® can then be measured by transferring the biosensor to a well containing RIC8A•Gαi1 complex, RIC8A alone or Gαi1 alone for 600 seconds at 1K RPM. Next, dissociation can be followed by transferring the biosensor to buffer only for 900 seconds.

Using this technique, it was first confirmed that CA8332 binds to RIC8A•Gαi1 complex but not to RIC8A alone or Gαi1 alone. For this purpose, the different analytes were dispensed in three different wells containing RIC8A (5 μM), Gαi1 (5 μM), or the RIC8A•Gαi1 complex (5 μM). The binding isotherms in FIG. 9, Panel A, illustrate that CA8332 binds to RIC8A•Gαi1 complex but not to RIC8A alone or Gαi1 alone. After 600 seconds of association, the biosensors were transferred to buffer allowing dissociation to be measured for 900 seconds at 1K RPM. These dissociation isotherms indicate that the ternary CA8332•RIC8A•Gαi1 complex is tight and that CA8332 dissociates slowly from RIC8A•Gαi1.

Figure 9:
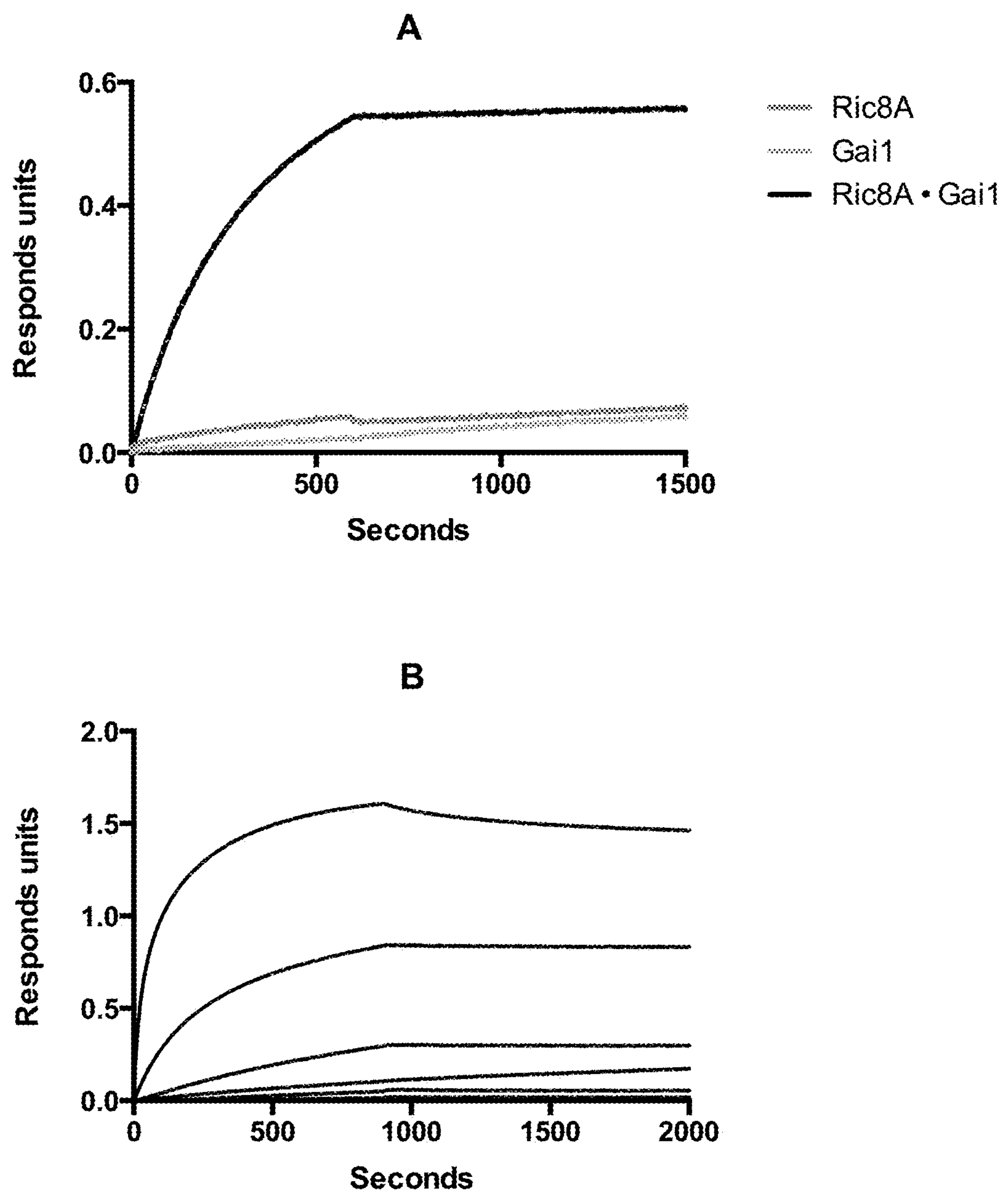
FIG. 9. Octet Red96 Sensorgram of binding of CA8332 to RIC8A, Gαi1 and RIC8A•Gαi1 complex. Panel A. Chart showing association (0-600 seconds) and dissociation (600-1500 seconds) of CA8332 to RIC8A (alone) in grey, to Gαi1 (alone) in light gray and to the RIC8A•Gαi1 complex in black. Panel B. Dose responds curves showing association (0-900 seconds) and dissociation (900-2000 seconds) using 125, 12.5, 1.25, 0.125, 0.0125, 0 μm of the purified RIC8A•Gαi1 complex.

In order to accurately measure the affinity of CA8332 for the RIC8A•Gαi1 complex, CA8332 was immobilized on the biosensor (as described previously) and measured its binding kinetics at different concentration of the purified RIC8A•Gαi1 complex (using 125, 12.5, 1.25, 0.125, 0.0125, 0 μM), the association was measured for 900 seconds and the dissociation for 1100 seconds (FIG. 9, Panel B). The raw data acquired for the interaction between the NANOBODY® (CA8332) and the RIC8A•Gαi1 complex were processed and fit to a curve in order to extract values of kon, koff and Kd. Processing began with reference correction to compensate for signal drift of the immobilized biosensor with the binding buffer. Using a reference biosensor, the signal generated by a biosensor with only the NANOBODY® that probed the binding buffer was subtracted from both the association and dissociation steps for the interaction between the NANOBODY® and the complex. The binding to the complex showed a dose-dependent signal; the curve fitting suggests that the binding occurs in a 1:1 model with an estimated Kd value of 0.2 nM.

Part 2. Binding Agents for the Stabilization of Protein-DNA Interactions

Example 1 a) Preparation of a Protein Complex as Immunogen for Camelid Immunization

In order to identify NANOBODIES® that stabilize and selectively bind to a transient protein/DNA complex, the *Escherichia coli* DNA gyrase in complex with a DNA fragment was chosen as a model.

Bacterial topoisomerases IIa (DNA gyrase and Topoisomerase IV) introduce negative DNA supercoils[35] and remove positive supercoils, functions essential for bacterial DNA transcription and replication.[36] DNA gyrase is composed of two heterodimeric subunits: GyrA comprising the DNA ligation activity, and GyrB comprising the ATPase activity. The DNA gyrase supercoiling reaction is a complex process that is incompletely understood. However, the catalytic cycle gives ample opportunity for disruption by inhibitors, which can, for example, interfere with DNA binding, DNA cleavage, DNA strand passage and ATP hydrolysis.[37] A variety of natural products (simocyclinones),[38] synthetic small molecules (quinolones),[35] and protein-based entities (CcdB),[39] have been identified as potent inhibitors. Interestingly, all these topoisomerase inhibitors block the enzyme at different stages of the catalytic cycle. Hence, the different inhibitor/protein complexes must have different conformations.

Ciprofloxacin (CFX) was used, a second-generation fluoroquinolone, which mechanism of action is to block DNA gyrase in the religation stage,[40] producing a stable covalent ternary complex DNA/Gyrase/CFX.[35] The *E. coli* DNA gyrase construct used is a fusion of GyrB (388-804) (NP 418154) and GyrA (1-525) (NP 416734) as described previously.[41, 42] A 34 bp DNA fragment containing a DNA gyrase hotspot in the center was used to prepare the complex.

```
Gyr_fw
                                        (SEQ ID NO: 79)
5'-ACCAAGGTCATGAATGACTATGCACGTAAAACAG-3'

Gyr_rv
                                        (SEQ ID NO: 80)
5'-CTGTTTTACGTGCATAGTCATTCATGACCTTGGT-3'
```

Figure 10:
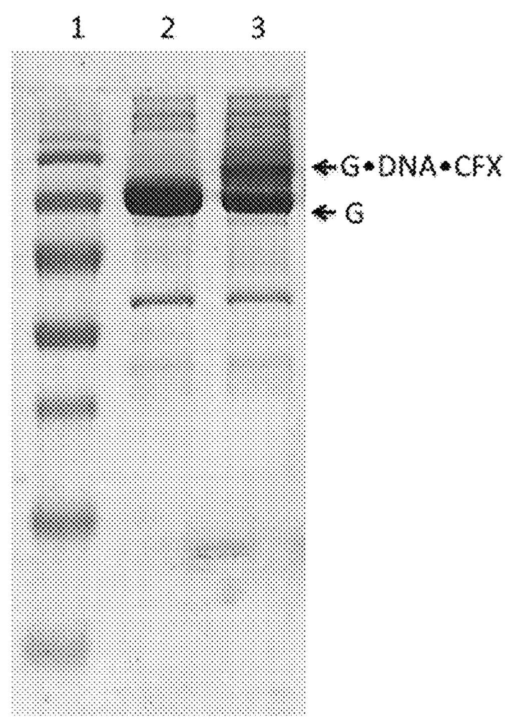
FIG. 10. SDS-PAGE of the *E. coli* DNA gyrase. Lane 1, molecular weight marker (Fermentas). Lane 2, DNA gyrase. Lane 3, ternary covalent complex (DNA gyrase•DNA•Ciprofloxacin).

Five μM of DNA gyrase was incubated with a ten-fold excess of DNA (reaction buffer: 100 mM Tris, 100 mM KCl, 12 mM MgCl2, 10 mM DTT and 20% glycerol). One mM of Cirprofloxacin (17850-25G-F, Fluka) was added to the complex and further incubated for 16 hours at 37° C. The covalent complex was detected on SDS/PAGE gel (FIG. 10).

b) Induction of an Antibody-Mediated Immune Response in Llama Against the Cross-Linked DNA•Gyrase•CFX Complex One llama was immunized with the DNA/gyrase/CFX complex as immunogen, prepared as described above (point a). The immunization scheme is identical as described in Step 1b of the General Method.

c) Cloning of the Llama NANOBODY®-Immune Repertoires in Yeast Display Vector

Identical to Step 1c of the General Method.

d) Fluorescent Labeling of DNA•Gyrase Complex

Random labeling on amines inhibits the binding of DNA gyrase to the DNA. Hence, a labeled DNA fragment was used containing an ALEXA FLUOR®-488 dye on the 5' end.

```
Gyr_fwAlexa488
                                        (SEQ ID NO: 79)
A488-5'-ACCAAGGTCATGAATGACTATGCACGTAAAACAG-3'
```

e) Selection of NANOBODIES® Binding to the DNA•Gyrase•CFX Complex.

For the first selection round, induced yeast cells were incubated with 1 ml DNA-ALEXA FLUOR®-488•gyrase•CFX complex diluted in PBS buffer. The DNA-ALEXA FLUOR®-488•gyrase•CFX complex was formed in 100 mM Tris, 100 mM KCl, 12 mM MgCl2, 10 mM DTT and 20% glycerol buffer as described in point a. To select for NANOBODIES® that specifically stabilize DNA•gyrase•CFX complex, but not gyrase alone, a different FACS sorting strategy was used as illustrated in FIG. 2. Since labeling of both partners interfered with complex formation (point d), it was irrelevant to look for such kind of double-positive events in FACS. Therefore, it was chosen to label only the DNA molecule, especially because the presence of DNA-only binding NANOBODIES® in this immune library was not expected. This means that the following sorting gates (FIGS. 11A and 11B) could be applied to select for complex binders in a two-color FACS experiment (R-Phycoerythrin, ALEXA FLUOR®-488). High R-Phycoerythrin fluorescence indicates that the yeast cell expresses a NANOBODY® on its surface. High ALEXA FLUOR®-488 fluorescence indicates that the displayed NANOBODY® binds DNA, and, thus, in this case, DNA-ALEXA FLUOR®-488•gyrase•CFX complex.

Yeast cells scoring on two colors express a NANOBODY® that binds the DNA•gyrase•CFX complex but not to unlabeled gyrase alone. In a first round of selection (see FIG. 10), about 10% of double-positive cells (binding DNA•gyrase•CFX, P3) were sorted and yeast clones expressing aspecific NANOBODIES® or NANOBODIES® that bind gyrase only were discarded.

In the subsequent FACS rounds, the amount of stained yeast was lowered to $1\times10^7$ in rounds 2 and 3 and $5\times10^6$ cells in round 4. The staining volume was lowered accordingly to 500 μl and 200 μl. Until no significant shift in ALEXA FLUOR®-488 fluorescence was seen (rounds 2 and 3), a very mild sorting strategy was used, where 10% of the total yeast cells were collected (P3 in FIGS. 11A and 11B). Also, from round 3 on, a more stringent selection was performed for complex stabilizing NANOBODIES®. Therefore, a condition was included where labeled DNA and unlabeled gyrase were mixed in the absence of the stabilizing antibiotic CFX (Rounds 3b and 4b in FIGS. 11A and 11B). To obtain NANOBODIES® that bind DNA•gyrase•CFX (condition a in FIGS. 11A and 11B) or DNA•gyrase complex (condition b in FIGS. 11A and 11B), only the top 2% of PE and ALEXA FLUOR®-488 positive cells where sorted in round 4 (P4 in FIGS. 11A and 11B).

Results

As illustrated in FIGS. 11A and 11B, an enrichment for the selected population (P4) is seen after four rounds of selection by FACS. The population of yeast cells that display NANOBODIES® (positive signal in the R-Phycoerythrin channel) showed increased binding to DNA•gyrase•CFX complex (positive signal in the ALEXA FLUOR®-488 channel). As expected, this enrichment is smaller when no CFX is present, a smaller fraction of NANOBODIES® are able to bind the DNA•gyrase in the absence of CFX.

To further characterize the NANOBODIES® that were obtained by co-selection by FACS, the sequence was determined for 100 clones recovered from round 2 (P3 in FIGS. 11A and 11B), 100 clones recovered from round 3a and round 3b (P3) and 100 clones recovered from round 4a and 4b (P4).

Sequence alignment of all of these clones shows that the selected NANOBODIES® belong to 22 different sequence families only (characterized by differences in CDR3 loop[14]). Representative sequences of the six largest sequence families are aligned in FIG. 12 and shown in Table 5.

TABLE 5

| CA pCTCON2 *S. cerevisiae* | CA pMESy4 *E. coli* | Family | Occurrence | CDR3 Sequence |
|---|---|---|---|---|
| CA9302 | CA9317 | 1 | 11 | AAALRPNSVQYKY (SEQ ID NO: 37) |
| CA9303 | CA9318 | 3 | 8 | AATPGYTSASKVPSDYAY (SEQ ID NO: 38) |
| CA9304 | CA9319 | 5 | 4 | GADSAGWFRIRQVPADYDY (SEQ ID NO: 39) |
| CA9305 | CA9320 | 7 | 3 | ARGAFSFATTVQSDYNY (SEQ ID NO: 40) |
| CA9307 | CA9322 | 10 | 2 | TADHALRLSSRLTDYDY (SEQ ID NO: 41) |
| CA9309 | CA9324 | 12 | 4 | AADPSRWYFCSSDSNPNTFDS (SEQ ID NO: 42) |

f) Selection of Gyrase Only Binding NANOBODIES®

Selection of binders that recognize only one partner instead of the complex but do not bind the complex were selected in a similar manner as described in the previous section with the following modifications. Since we were not looking for complex binding Nbs, gyrase could be fluorescently labeled as described in paragraph c of Example 1. In two selection rounds (FIG. 13), NANOBODY®-expressing yeast cells were sorted that exclusively bind to gyrase DYLIGHT®-405 (P3 and P4).

Results

Even though there was no clear enrichment seen (FIG. 13), confidence was high that enrichment for yeast cells expressing a NANOBODY® (high PE fluorescence) that binds to gyrase (high DYLIGHT®-405 fluorescence) was successful. From the selection output of round 2 (P4), 100 clones were sequenced and aligned (FIG. 14). All clones belong to nine sequence families (Table 6) and some of them were identical to the ones selected on the DNA•gyrase•CFX complex in the previous paragraph (Table 5).

TABLE 6

| CA pCTCON2 *S. cerevisiae* | CA pMESy4 *E. coli* | Family | Occurrence | CDR3 Sequence |
|---|---|---|---|---|
| CA9302 | CA9317 | 1 | 11 | AAALRPNSVQYKY (SEQ ID NO: 43) |
| CA9303 | CA9318 | 3 | 8 | AATPGYTSASKVPSDYAY (SEQ ID NO: 44) |
| CA9304 | CA9319 | 5 | 4 | GADSAGWFRIRQVPADYDY (SEQ ID NO: 45) |
| CA9305 | CA9320 | 7 | 3 | ARGAFSFATTVQSDYNY (SEQ ID NO: 46) |
| CA9306 | CA9321 | 9 | 2 | ALQYGWRWSWDDGSARDMRY (SEQ ID NO: 47) |
| CA9308 | CA9323 | 11 | 2 | ATKTRGGDWRSGKNWNY (SEQ ID NO: 48) |
| CA9309 | CA9324 | 12 | 4 | AADPSRWYFCSSDSNPNTFDS (SEQ ID NO: 49) |
| CA9310 | CA9325 | 15 | 2 | AASTGYGTNSRYDYDY (SEQ ID NO: 50) |

g) NANOBODY® Characterization by FACS Screening

In order to characterize the selected NANOBODY® families, a FACS screening was performed on single yeast cells expressing a particular NANOBODY®. Induced yeast cells were incubated with DNA-ALEXA FLUOR®-647•gyrase•CFX, DNA-ALEXA FLUOR®-647•gyrase•CFX and 1 μM gyrase-DYLIGHT®-405.

Results

Figure 15A:
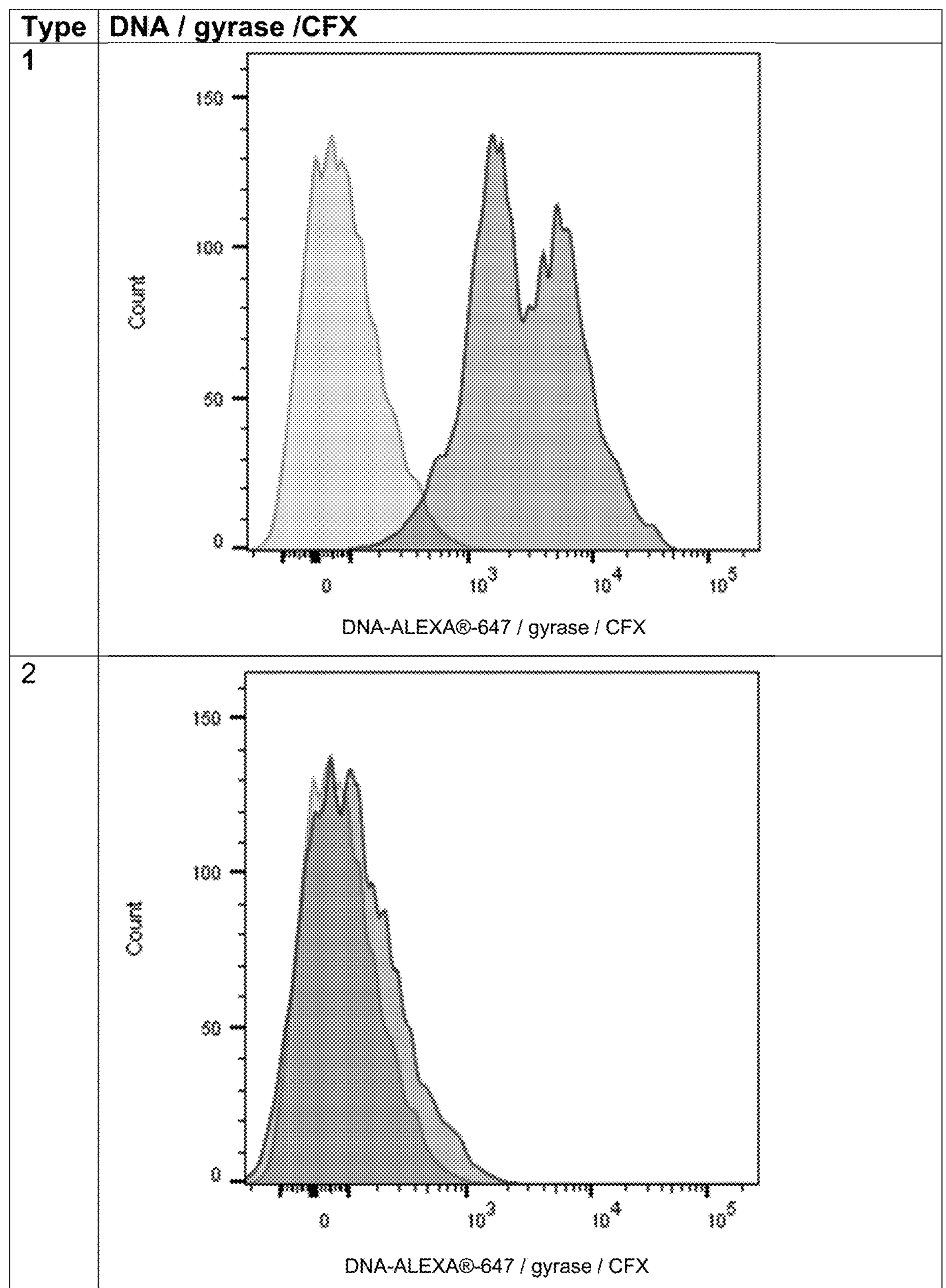
FIGS. 15A-15C. Summary of the different interaction profiles of NANOBODIES® in a FACS screening experiment. Target molecules for NANOBODY® binding.
Figure 15B:
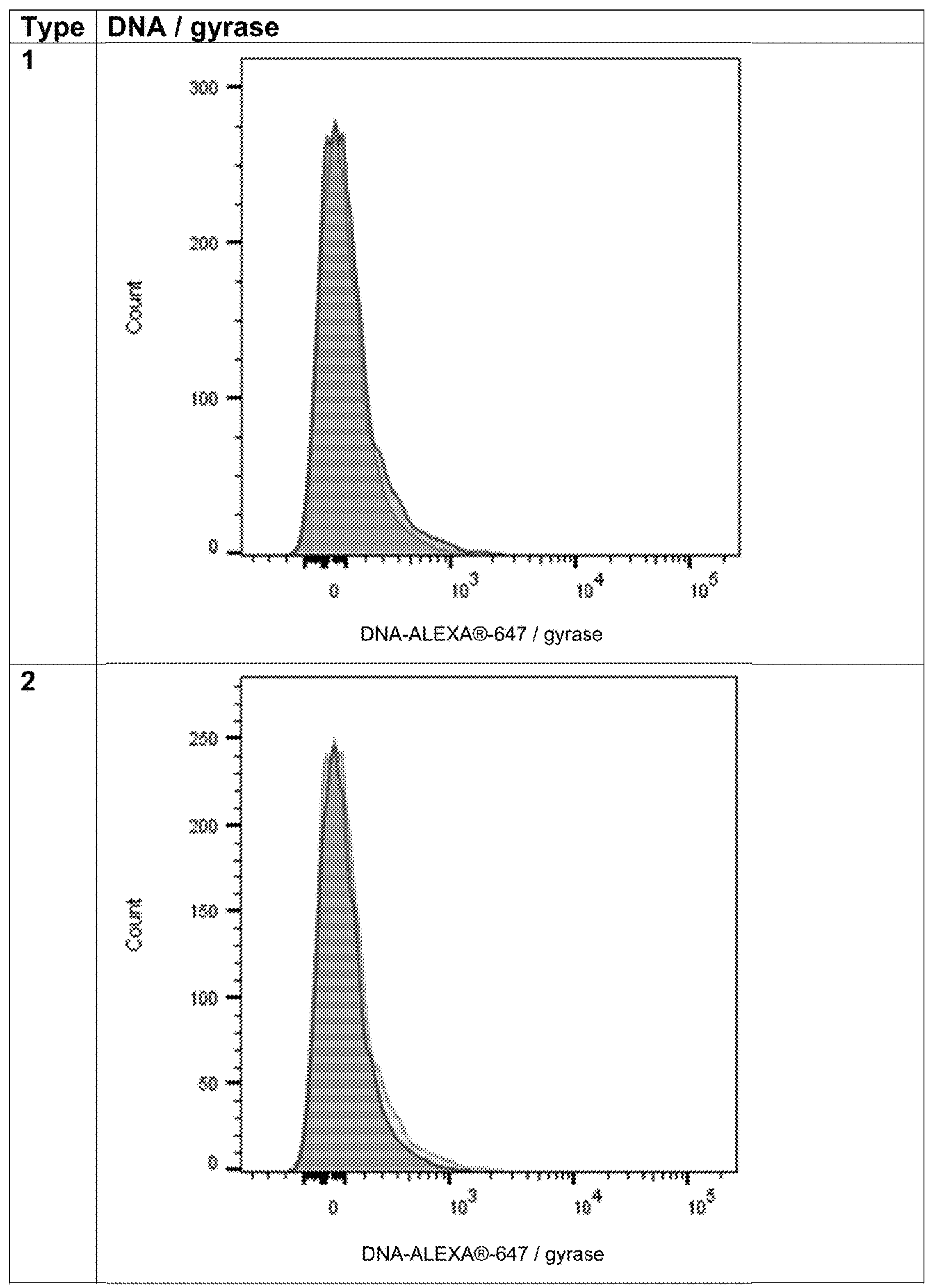
Figure 15C:
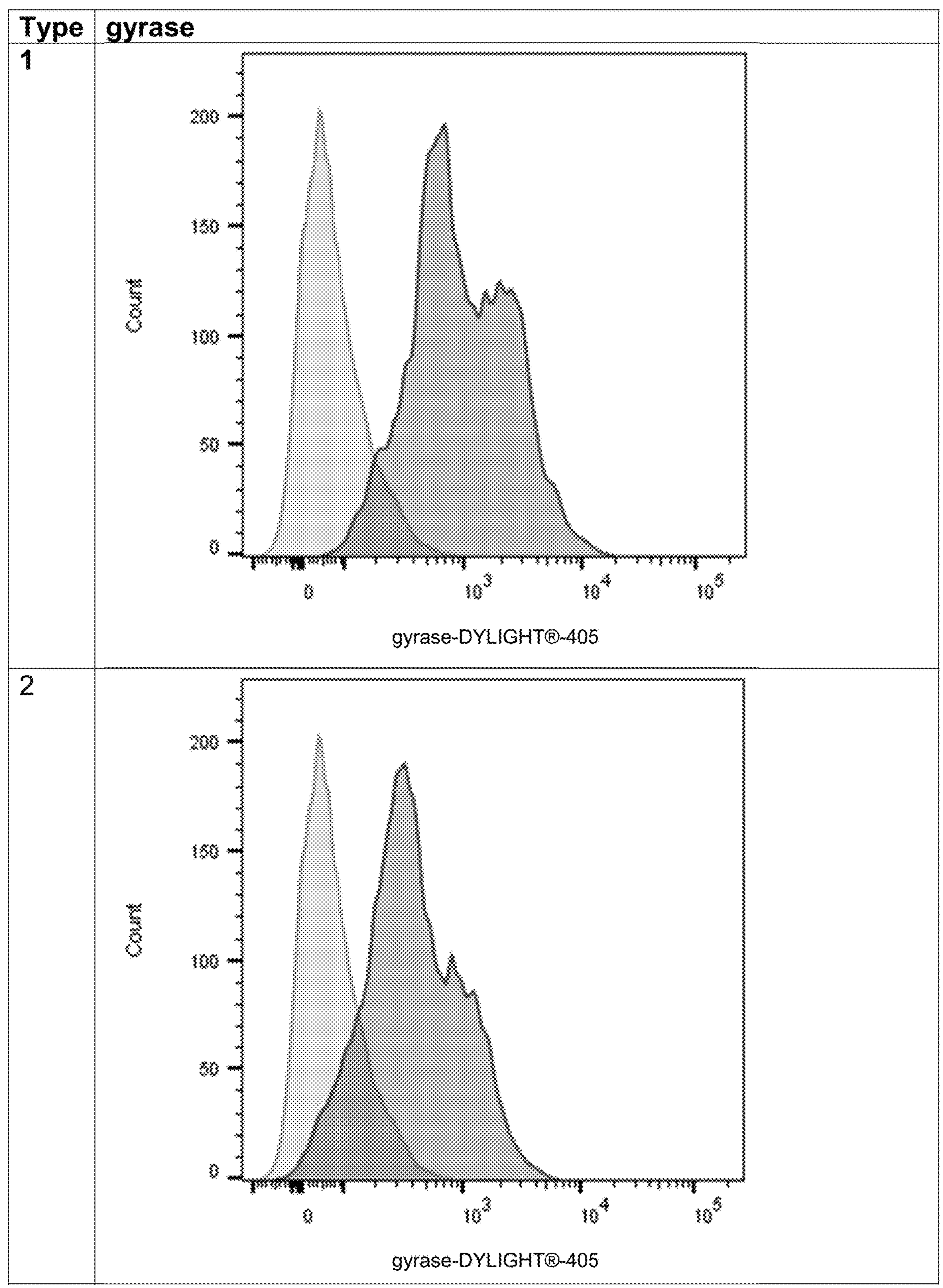

With this screening method, characterization of all NANOBODY® families was performed and classified them into two interaction profiles (FIGS. 15A-15C):

Type 1: NANOBODIES® that show binding to DNA•gyrase•CFX complex and to free gyrase. In contrast, type 1 binders do not show binding to a DNA•gyrase and thus are not able to stabilize the complex in absence of CFX. However, this does not mean that these NANOBODIES® are not binding a complex specific conformation of gyrase; they might just not be as efficient as CFX to keep DNA in complex with the gyrase.

Type 2: NANOBODIES® that only show binding for free gyrase and do not bind DNA•gyrase•CFX or DNA•gyrase complexes. They are not able to recognize the complex conformation of gyrase; hence, they inhibit DNA binding.

Results from this screening are summarized (Table 7) and show that both described selection methods (paragraphs e and f) result both in type 1 and type 2 binders.

TABLE 7

| CA pCTCON2 *S. cerevisiae* | CA pMESy4 *E. coli* | DNA-gyrase-CFX | DNA-gyrase | gyrase | Type |
|---|---|---|---|---|---|
| CA9302 | CA9317 | yes | no | yes | 1 |
| CA9303 | CA9318 | yes | no | yes | 1 |
| CA9304 | CA9319 | yes | no | yes | 1 |
| CA9305 | CA9320 | yes | no | yes | 1 |
| CA9306 | CA9321 | no | no | yes | 2 |
| CA9307 | CA9322 | no | no | yes | 2 |
| CA9308 | CA9323 | yes | no | yes | 1 |
| CA9309 | CA9324 | yes | no | yes | 1 |
| CA9310 | CA9325 | no | no | yes | 2 |

REFERENCES

1. Wells, J. A. & McClendon, C. L. Reaching for high-hanging fruit in drug discovery at protein-protein interfaces. *Nature* 450:1001-9 (2007).
2. Rudolph, J. Inhibiting transient protein-protein interactions: lessons from the Cdc25 protein tyrosine phosphatases. *Nat. Rev. Cancer* 7:202-11 (2007).
3. Fischer, P. M. & Lane, D. P. Small-molecule inhibitors of the p53 suppressor HDM2: have protein—protein interactions come of age as drug targets? *Trends in Pharmacological Sciences* 25:1-4 (2004).
4. Altieri, D. C. Survivin, cancer networks and pathway-directed drug discovery. *Nature reviews. Cancer* 8:61-70 (2008).
5. Nooren, I. M. & Thornton, J. M. Diversity of protein-protein interactions. *EMBO J.* 22:3486-92 (2003).
6. Wodak, S. J., Vlasblom, J., Turinsky, A. L. & Pu, S. Protein-protein interaction networks: the puzzling riches. *Curr. Opin. Struct. Biol.* 23:941-53 (2013).
7. Perkins, J. R., Diboun, I., Dessailly, B. H., Lees, J. G. & Orengo, C. Transient protein-protein interactions: structural, functional, and network properties. *Structure* 18:1233-43 (2010).
8. Aloy, P. & Russell, R. B. Structural systems biology: modelling protein interactions. *Nature reviews. Molecular cell biology* 7:188-97 (2006).
9. Wu, M. et al. Structures of a key interaction protein from the *Trypanosoma brucei* editosome in complex with single domain antibodies. *J. Struct. Biol.* 174:124-36 (2011).
10. Magalhaes, A. C., Dunn, H. & Ferguson, S. S. Regulation of GPCR activity, trafficking and localization by GPCR-interacting proteins. *British journal of pharmacology* 165:1717-1736 (2012).
11. Lemmon, M. A. & Schlessinger, J. Cell signaling by receptor tyrosine kinases. *Cell* 141:1117-34 (2010).
12. Vidal, M., Cusick, M. E. & Barabasi, A. L. Interactome networks and human disease. *Cell* 144:986-98 (2011).
13. Assenberg, R., Wan, P. T., Geisse, S. & Mayr, L. M. Advances in recombinant protein expression for use in pharmaceutical research. *Curr. Opin. Struct. Biol.* (2013).
14. Young, C. L., Britton, Z. T. & Robinson, A. S. Recombinant protein expression and purification: a comprehensive review of affinity tags and microbial applications. *Biotechnol. J.* 7:620-34 (2012).
15. Hoogenboom, H. R. Selecting and screening recombinant antibody libraries. Nat. *Biotechnol.* 23:1105-16 (2005).
16. Ryckaert, S., Pardon, E., Steyaert, J. & Callewaert, N. Isolation of antigen-binding camelid heavy chain antibody fragments (NANOBODIES®) from an immune library displayed on the surface of *Pichia pastoris. J. Biotechnol.* 145:93-8 (2010).
17. Garman, E. F. Developments in x-ray crystallographic structure determination of biological macromolecules. *Science* 343:1102-8 (2014).
18. Irannejad, R. et al. Conformational biosensors reveal GPCR signalling from endosomes. *Nature* 495:534-8 (2013).
19. Horovitz, A. Double-mutant cycles: a powerful tool for analyzing protein structure and function. *Folding and Design* 1:R121-R126 (1996).
20. Leitner, A. et al. Probing Native Protein Structures by Chemical Cross-linking, Mass Spectrometry, and Bioinformatics. *Molecular & Cellular Proteomics* 9:1634-1649 (2010).
21. Bich, C. et al. Reactivity and applications of new amine reactive cross-linkers for mass spectrometric detection of protein-protein complexes. *Anal. Chem.* 82:172-9 (2010).
22. Steyaert, J. & Kobilka, B. K. NANOBODY® stabilization of G protein-coupled receptor conformational states. *Curr. Opin. Struct. Biol.* 21:567-72 (2011).
24. Pardon, E. et al. A general protocol for the generation of NANOBODIES® for structural biology. *Nature Protocols* 9:674-693 (2014).
25. Chao, G. et al. Isolating and engineering human antibodies using yeast surface display. *Nat. Protoc.* 1:755-68 (2006).
26. Sprang, S. R. G protein mechanisms: insights from structural analysis. *Annu. Rev. Biochem.* 66:639-78 (1997).
27. Cherfils, J. & Chardin, P. GEFs: structural basis for their activation of small GTP-binding proteins. *Trends Biochem. Sci.* 24:306-11 (1999).
28. Pierce, K. L., Premont, R. T. & Lefkowitz, R. J. Seven-transmembrane receptors. *Nat. Rev. Mol. Cell. Biol.* 3:639-50 (2002).
29. Tall, G. G., Krumins, A. M. & Gilman, A. G. Mammalian Ric-8A (synembryn) is a heterotrimeric Galpha protein guanine nucleotide exchange factor. *J. Biol. Chem.* 278:8356-62 (2003).
30. Afshar, K. et al. RIC-8 is required for GPR-1/2-dependent Galpha function during asymmetric division of *C. elegans* embryos. *Cell* 119:219-30 (2004).
31. Miller, K. G., Emerson, M. D., McManus, J. R. & Rand, J. B. RIC-8 (Synembryn): a novel conserved protein that is required for G(q)alpha signaling in the *C. elegans* nervous system. *Neuron* 27:289-99 (2000).
32. David, N. B. et al. *Drosophila* Ric-8 regulates Galphai cortical localization to promote Galphai-dependent planar orientation of the mitotic spindle during asymmetric cell division. *Nat. Cell. Biol.* 7:1083-90 (2005).
33. Woodard, G. E. et al. Ric-8A and Gi alpha recruit LGN, NuMA, and dynein to the cell cortex to help orient the mitotic spindle. *Mol. Cell. Biol.* 30:3519-30 (2010).
34. Thomas, C. J. et al. The nucleotide exchange factor Ric-8A is a chaperone for the conformationally dynamic nucleotide-free state of Galphai1. *PLoS One* 6:e23197 (2011).
35. Wohlkonig, A. et al. Structural basis of quinolone inhibition of type IIA topoisomerases and target-mediated resistance. *Nat. Struct. Mol. Biol.* 17:1152-1153 (2010).
36. Dong, K. C. & Berger, J. M. Structural basis for gate-DNA recognition and bending by type IIA topoisomerases. *Nature* 450:1201-5 (2007).

37. Collin, F., Karkare, S. & Maxwell, A. Exploiting bacterial DNA gyrase as a drug target: current state and perspectives. *Appl. Microbiol. Biotechnol.* 92:479-97 (2011).
38. Edwards, M. J. et al. A crystal structure of the bifunctional antibiotic simocyclinone D8, bound to DNA gyrase. *Science* 326:1415-8 (2009).
39. Smith, A. B. & Maxwell, A. A strand-passage conformation of DNA gyrase is required to allow the bacterial toxin, CcdB, to access its binding site. *Nucleic Acids Res.* 34:4667-76 (2006).
40. Aldred, K. J., Kerns, R. J. & Osheroff, N. Mechanism of quinolone action and resistance. *Biochemistry* 53:1565-74 (2014).
41. Schoeffler, A. J., May, A. P. & Berger, J. M. A domain insertion in *Escherichia coli* GyrB adopts a novel fold that plays a critical role in gyrase function. *Nucleic Acids Res.* 38:7830-44 (2010).
42. Rasmussen S. G., Choi H. J., Fung J. J., Pardon E., Casarosa P., Chae P. S., Devree B. T., Rosenbaum D. M., Thian F. S., Kobilka T. S., Schnapp A., Konetzki I., Sunahara R. K., Gellman S. H., Pautsch A., Steyaert J., Weis W. I., Kobilka B. K. Structure of a NANOBODY®-stabilized active state of the β(2) adrenoceptor. *Nature* 2011 Jan. 13; 469(7329): 175-80.
43. Kruse A. C., Ring A. M., Manglik A., Hu J., Hu K., Eitel K., Hubner H., Pardon E., Valant C., Sexton P. M., Christopoulos A., Felder C. C., Gmeiner P., Steyaert J., Weis W. I., Garcia K. C., Wess J., Kobilka B. K. Activation and allosteric modulation of a muscarinic acetylcholine receptor. *Nature* 2013 Dec. 5; 504(7478):101-6.

The invention claimed is:

1. A method for selecting a conformation-selective binding agent of a transient protein complex comprising a conformational epitope, the method comprising the steps of:

a) displaying a collection of binding agents at the extracellular surfaces of a population of cells; and b) utilizing cell sorting to separate and select, from the population of cells, cells displaying binding agents that i. specifically bind to a conformational epitope of the transient protein complex and not to the individual members of the transient protein complex, and/or ii. specifically bind to a conformational epitope of one of the individual members of the transient protein complex and not to a conformational epitope of the transient protein complex nor to the other individual member(s) of the transient protein complex, and/or iii. specifically bind to a conformational epitope of one of the individual members of the transient protein complex and to a conformational epitope of the transient protein complex and not to the other individual member(s) of the transient protein complex;

wherein the transient protein complex comprises at least two interacting individual members; and wherein the individual members of the transient protein complex are distinguishably tagged.

2. The method of claim 1, wherein step b) comprises the steps of:

a) incubating a mixture of distinguishably tagged individual members of the transient protein complex with the population of cells displaying the binding agents under suitable conditions to allow binding to the binding agents displayed at the extracellular surface of the cells; and b) separating and selecting conformation-selective binding agents by utilizing cell sorting to select, from said population of cells, cells displaying binding agents that:

i. specifically bind to a conformational epitope of the transient protein complex and not to a conformational epitope of the individual members of the transient protein complex, and/or ii. specifically bind to a conformational epitope of one of the individual members of the transient protein complex and not to a conformational epitope of the transient protein complex nor to the other individual member(s) of the transient protein complex, and/or iii. specifically bind to a conformational epitope of one of the individual members of the transient protein complex and to a conformational epitope of the transient protein complex and not to the other individual member(s) of the transient protein complex.

3. The method of claim 1, wherein at least one of the individual members of the transient protein complex is labeled with a fluorescent label.

4. The method of claim 3, wherein the individual members of the transient protein complex are each labeled with a distinguishable fluorescent label.

5. The method of claim 1, wherein the cell sorting in step b) is done utilizing fluorescence-activated cell sorting ("FACS").

6. The method of claim 1, wherein the transient protein complex is a protein-protein complex comprising at least two interacting monomeric proteins.

7. The method of claim 1, wherein the transient protein complex is a protein-nucleic acid complex comprising at least one monomeric protein interacting with at least one nucleic acid molecule.

8. The method of claim 1, wherein the method further comprises isolating the binding agent from the cell sorted in step b).

9. The method of claim 8, further comprising:

measuring the binding specificity and/or affinity of the binding agent for the conformational epitope of the transient protein complex as compared to the individual members of the protein complex by any suitable technique.

10. The method according to claim 9, wherein the suitable technique is a biophysical method.

11. The method according to claim 9, wherein the suitable technique is fluorescence-activated cell sorting ("FACS").

12. The method of claim 1, wherein the collection of binding agents is a library of antibodies or antibody fragments.

13. The method of claim 12, wherein the antibody fragments are immunoglobulin single-domain antibodies.

14. The method according to claim 13, wherein the immunoglobulin single-domain antibodies are VHH.

15. The method of claim 12, wherein said antibodies or antibody fragments are obtained from an animal that has been immunized with the protein complex in a cross-linked form.

16. The method of claim 15, wherein said animal is a camelid.

17. The method of claim 1, wherein said population of cells is a population of yeast cells.

18. A method for selecting a conformation-selective binding agent of a conformational epitope of a transient protein complex, the method comprising:

a) displaying a collection of binding agents at the extracellular surfaces of a population of cells; and b) utilizing cell sorting to separate and select, from the population of cells, cells displaying binding agents that i. specifically bind to the conformational epitope of the transient protein complex and not to the individual members of the transient protein complex, and/or ii. specifically bind to one of the individual members of the transient protein complex and to the conformational epitope of the transient protein complex and not to the other individual member(s) of the transient protein complex;

wherein the transient protein complex comprises at least two interacting individual members; and wherein the individual members of the transient protein complex are distinguishably tagged.

* * * * *

SEQUENCE LISTING

```
<160> NUMBER OF SEQ ID NOS: 81

<210> SEQ ID NO 1
<211> LENGTH: 10
<212> TYPE: PRT
<213> ORGANISM: Artificial Sequence
<220> FEATURE:
<223> OTHER INFORMATION: Linker

<400> SEQUENCE: 1

Gly Ser Gly Ser Gly Ser Gly Ser Gly Ser
1               5                   10


<210> SEQ ID NO 2
<211> LENGTH: 20
<212> TYPE: PRT
<213> ORGANISM: Artificial Sequence
<220> FEATURE:
<223> OTHER INFORMATION: Linker

<400> SEQUENCE: 2

Gly Ser Gly Ser Gly Ser Gly Ser Gly Ser Gly Ser Gly Ser Gly Ser
1               5                   10                  15

Gly Ser Gly Ser
            20


<210> SEQ ID NO 3
<211> LENGTH: 15
<212> TYPE: PRT
<213> ORGANISM: Artificial Sequence
<220> FEATURE:
<223> OTHER INFORMATION: Linker

<400> SEQUENCE: 3

Gly Gly Gly Gly Ser Gly Gly Gly Gly Ser Gly Gly Gly Gly Ser
1               5                   10                  15


<210> SEQ ID NO 4
<211> LENGTH: 17
<212> TYPE: PRT
<213> ORGANISM: Artificial Sequence
<220> FEATURE:
<223> OTHER INFORMATION: Linker

<400> SEQUENCE: 4

Ala His His Ser Glu Asp Pro Ser Ser Lys Ala Pro Lys Ala Pro Met
1               5                   10                  15
```

Ala

<210> SEQ ID NO 5
<211> LENGTH: 16
<212> TYPE: PRT
<213> ORGANISM: Artificial Sequence
<220> FEATURE:
<223> OTHER INFORMATION: Linker

<400> SEQUENCE: 5

Ser Pro Ser Thr Pro Pro Thr Pro Ser Pro Ser Thr Pro Pro Ala Ser
1 5 10 15

<210> SEQ ID NO 6
<211> LENGTH: 4
<212> TYPE: PRT
<213> ORGANISM: Artificial Sequence
<220> FEATURE:
<223> OTHER INFORMATION: Factor Xa cleavage site

<400> SEQUENCE: 6

Ile Glu Gly Arg
1

<210> SEQ ID NO 7
<211> LENGTH: 4
<212> TYPE: PRT
<213> ORGANISM: Artificial Sequence
<220> FEATURE:
<223> OTHER INFORMATION: thrombin cleavage site

<400> SEQUENCE: 7

Leu Val Pro Arg
1

<210> SEQ ID NO 8
<211> LENGTH: 5
<212> TYPE: PRT
<213> ORGANISM: Artificial Sequence
<220> FEATURE:
<223> OTHER INFORMATION: enterokinase cleaving site

<400> SEQUENCE: 8

Asp Asp Asp Asp Lys
1 5

<210> SEQ ID NO 9
<211> LENGTH: 8
<212> TYPE: PRT
<213> ORGANISM: Artificial Sequence
<220> FEATURE:
<223> OTHER INFORMATION: PreScission -or 3C- cleavage site

<400> SEQUENCE: 9

Leu Glu Val Leu Phe Gln Gly Pro
1 5

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
gtcctggctg ctcttctaca agg 23

<210> SEQ ID NO 11
<211> LENGTH: 23
<212> TYPE: DNA
<213> ORGANISM: Artificial Sequence
<220> FEATURE:
<223> OTHER INFORMATION: Primer

<400> SEQUENCE: 11
ggtacgtgct gttgaactgt tcc 23

<210> SEQ ID NO 12
<211> LENGTH: 53
<212> TYPE: DNA
<213> ORGANISM: Artificial Sequence
<220> FEATURE:
<223> OTHER INFORMATION: Primer

<400> SEQUENCE: 12
cggtagcgga ggcggagggt cggctagcca ggtgcagctg gtggagtctg ggg 53

<210> SEQ ID NO 13
<211> LENGTH: 52
<212> TYPE: DNA
<213> ORGANISM: Artificial Sequence
<220> FEATURE:
<223> OTHER INFORMATION: Primer

<400> SEQUENCE: 13
gggacccagg tcaccgtctc cagcggatcc gaacaaaagc ttatttctga ag 52

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
gttccagact acgctctgca gg 22

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
gattttgtta catctacact gttg 24

<210> SEQ ID NO 16
<211> LENGTH: 29
<212> TYPE: DNA
<213> ORGANISM: Artificial Sequence
<220> FEATURE:
<223> OTHER INFORMATION: Primer

<400> SEQUENCE: 16
gatgtgcagc tgcaggagtc tggrggagg 29

<210> SEQ ID NO 17
<211> LENGTH: 35
<212> TYPE: DNA
<213> ORGANISM: Artificial Sequence
<220> FEATURE:

<223> OTHER INFORMATION: Primer

<400> SEQUENCE: 17
ggactagtgc ggccgctgga gacggtgacc tgggt 35

<210> SEQ ID NO 18
<211> LENGTH: 21
<212> TYPE: PRT
<213> ORGANISM: Lama glama

<400> SEQUENCE: 18

Cys Ala Gly Asp Arg Gln Pro Tyr Val Tyr Asp Leu Pro Thr Ala Gln
1 5 10 15

Tyr Gln Tyr Asp Tyr
20

<210> SEQ ID NO 19
<211> LENGTH: 17
<212> TYPE: PRT
<213> ORGANISM: Lama glama

<400> SEQUENCE: 19

Cys Ala Ser Ser Ser Ile Glu Phe Gly Pro Leu Glu Asp Thr Tyr Asp
1 5 10 15

Tyr

<210> SEQ ID NO 20
<211> LENGTH: 20
<212> TYPE: PRT
<213> ORGANISM: Lama glama

<400> SEQUENCE: 20

Cys Ala Ala Glu Ala Arg Glu Phe Ser Val Gly Ser Tyr Tyr Ala Thr
1 5 10 15

Glu Tyr Asp Tyr
20

<210> SEQ ID NO 21
<211> LENGTH: 18
<212> TYPE: PRT
<213> ORGANISM: Lama glama

<400> SEQUENCE: 21

Cys Ala Ala Asp Arg Lys Pro Tyr Ser Tyr Tyr Pro Ser Asp Phe Gly
1 5 10 15

Ser Trp

<210> SEQ ID NO 22
<211> LENGTH: 19
<212> TYPE: PRT
<213> ORGANISM: Lama glama

<400> SEQUENCE: 22

Cys Ala Ala Thr Pro Ala Asp Ser Ala Phe Met Arg Asn Leu Arg Val
1 5 10 15

Tyr Asp Tyr

<210> SEQ ID NO 23
<211> LENGTH: 17
<212> TYPE: PRT
<213> ORGANISM: Lama glama

<400> SEQUENCE: 23

Cys Val Ala Arg Val Gly Ser Pro Ser Ser Ser Asp Arg Ala Tyr Gln
1 5 10 15

Tyr

<210> SEQ ID NO 24
<211> LENGTH: 20
<212> TYPE: PRT
<213> ORGANISM: Lama glama

<400> SEQUENCE: 24

Cys Ala Ala Thr Arg Arg Asp Phe Tyr Ile Ile Arg Asn Ser Arg Pro
1 5 10 15

Gln Phe Asp Tyr
20

<210> SEQ ID NO 25
<211> LENGTH: 16
<212> TYPE: PRT
<213> ORGANISM: Lama glama

<400> SEQUENCE: 25

Cys Ala Arg Cys Pro Ala Gly Ala Ala Cys Lys Val Glu Tyr Asp Tyr
1 5 10 15

<210> SEQ ID NO 26
<211> LENGTH: 21
<212> TYPE: PRT
<213> ORGANISM: Lama glama

<400> SEQUENCE: 26

Cys Ala Ala Thr Pro Ala Asp Leu Thr Val Val Ala Gly Pro Pro Arg
1 5 10 15

Ile Glu Met Trp Tyr
20

<210> SEQ ID NO 27
<211> LENGTH: 19
<212> TYPE: PRT
<213> ORGANISM: Lama glama

<400> SEQUENCE: 27

Cys Ala Ala Thr Ala Ala Asp Tyr Val Leu Arg Ser Arg Pro Ser Val
1 5 10 15

Tyr Ser Tyr

<210> SEQ ID NO 28
<211> LENGTH: 21
<212> TYPE: PRT
<213> ORGANISM: Lama glama

<400> SEQUENCE: 28

Cys Ala Ala Ala Ile Arg Asp Gly His Asn Tyr Tyr Ala Ser Asp Met
1 5 10 15

Arg Arg Tyr Asp Tyr
20

<210> SEQ ID NO 29
<211> LENGTH: 20
<212> TYPE: PRT
<213> ORGANISM: Lama glama

<400> SEQUENCE: 29

Ala Ser Asp Arg Arg Pro Tyr Arg Tyr Asn Ile Gly Thr Ala Glu Gly
1 5 10 15

Glu Tyr Asn Tyr
20

<210> SEQ ID NO 30
<211> LENGTH: 12
<212> TYPE: PRT
<213> ORGANISM: Lama glama

<400> SEQUENCE: 30

Gly Lys Gly Trp Phe Leu Asn Arg Arg Asp Glu Ser
1 5 10

<210> SEQ ID NO 31
<211> LENGTH: 19
<212> TYPE: PRT
<213> ORGANISM: Lama glama

<400> SEQUENCE: 31

Ala Ala Asp Arg Val Pro Tyr Arg Phe Gly Val Pro Ser Ile Asn Glu
1 5 10 15

Tyr Asp Tyr

<210> SEQ ID NO 32
<211> LENGTH: 10
<212> TYPE: PRT
<213> ORGANISM: Lama glama

<400> SEQUENCE: 32

Asn Phe Asn Val Arg Tyr Tyr Gly Glu Tyr
1 5 10

<210> SEQ ID NO 33
<211> LENGTH: 17
<212> TYPE: PRT
<213> ORGANISM: Lama glama

<400> SEQUENCE: 33

Ala Arg Thr Ser Arg Ala Ser Val Thr Thr Arg Val Ala Asp Phe Gly
1 5 10 15

Tyr

<210> SEQ ID NO 34
<211> LENGTH: 11
<212> TYPE: PRT
<213> ORGANISM: Lama glama

<400> SEQUENCE: 34

Asn Leu Gln Asn Arg Tyr Asp Ala Met Asp Tyr
1 5 10

<210> SEQ ID NO 35
<211> LENGTH: 8
<212> TYPE: PRT
<213> ORGANISM: Lama glama

<400> SEQUENCE: 35

Asn Thr Tyr Pro Val Asn Ser Tyr
1 5

<210> SEQ ID NO 36
<211> LENGTH: 12
<212> TYPE: PRT
<213> ORGANISM: Lama glama

<400> SEQUENCE: 36

Asn Ala Glu Pro Arg Tyr Tyr Gly Ala Ala Tyr Leu
1 5 10

<210> SEQ ID NO 37
<211> LENGTH: 13
<212> TYPE: PRT
<213> ORGANISM: Lama glama

<400> SEQUENCE: 37

Ala Ala Ala Leu Arg Pro Asn Ser Val Gln Tyr Lys Tyr
1 5 10

<210> SEQ ID NO 38
<211> LENGTH: 18
<212> TYPE: PRT
<213> ORGANISM: Lama glama

<400> SEQUENCE: 38

Ala Ala Thr Pro Gly Tyr Thr Ser Ala Ser Lys Val Pro Ser Asp Tyr
1 5 10 15

Ala Tyr

<210> SEQ ID NO 39
<211> LENGTH: 19
<212> TYPE: PRT
<213> ORGANISM: Lama glama

<400> SEQUENCE: 39

Gly Ala Asp Ser Ala Gly Trp Phe Arg Ile Arg Gln Val Pro Ala Asp
1 5 10 15

Tyr Asp Tyr

<210> SEQ ID NO 40
<211> LENGTH: 17
<212> TYPE: PRT
<213> ORGANISM: Lama glama

<400> SEQUENCE: 40

Ala Arg Gly Ala Phe Ser Phe Ala Thr Thr Val Gln Ser Asp Tyr Asn
1 5 10 15

Tyr

<210> SEQ ID NO 41
<211> LENGTH: 17
<212> TYPE: PRT
<213> ORGANISM: Lama glama

<400> SEQUENCE: 41

Thr Ala Asp His Ala Leu Arg Leu Ser Ser Arg Leu Thr Asp Tyr Asp
1 5 10 15

Tyr

<210> SEQ ID NO 42
<211> LENGTH: 21
<212> TYPE: PRT
<213> ORGANISM: Lama glama

<400> SEQUENCE: 42

Ala Ala Asp Pro Ser Arg Trp Tyr Phe Cys Ser Ser Asp Ser Asn Pro
1 5 10 15

Asn Thr Phe Asp Ser
20

<210> SEQ ID NO 43
<211> LENGTH: 13
<212> TYPE: PRT
<213> ORGANISM: Lama glama

<400> SEQUENCE: 43

Ala Ala Ala Leu Arg Pro Asn Ser Val Gln Tyr Lys Tyr
1 5 10

<210> SEQ ID NO 44
<211> LENGTH: 18
<212> TYPE: PRT
<213> ORGANISM: Lama glama

<400> SEQUENCE: 44

Ala Ala Thr Pro Gly Tyr Thr Ser Ala Ser Lys Val Pro Ser Asp Tyr
1 5 10 15

Ala Tyr

<210> SEQ ID NO 45
<211> LENGTH: 19
<212> TYPE: PRT
<213> ORGANISM: Lama glama

<400> SEQUENCE: 45

Gly Ala Asp Ser Ala Gly Trp Phe Arg Ile Arg Gln Val Pro Ala Asp
1 5 10 15

Tyr Asp Tyr

<210> SEQ ID NO 46
<211> LENGTH: 17
<212> TYPE: PRT
<213> ORGANISM: Lama glama

<400> SEQUENCE: 46

Ala Arg Gly Ala Phe Ser Phe Ala Thr Thr Val Gln Ser Asp Tyr Asn
1 5 10 15

Tyr

<210> SEQ ID NO 47
<211> LENGTH: 20
<212> TYPE: PRT
<213> ORGANISM: Lama glama

<400> SEQUENCE: 47

Ala Leu Gln Tyr Gly Trp Arg Trp Ser Trp Asp Asp Gly Ser Ala Arg
1 5 10 15

Asp Met Arg Tyr
20

<210> SEQ ID NO 48
<211> LENGTH: 17
<212> TYPE: PRT
<213> ORGANISM: Lama glama

<400> SEQUENCE: 48

```
Ala Thr Lys Thr Arg Gly Gly Asp Trp Arg Ser Gly Lys Asn Trp Asn
1               5                   10                  15

Tyr


<210> SEQ ID NO 49
<211> LENGTH: 21
<212> TYPE: PRT
<213> ORGANISM: Lama glama

<400> SEQUENCE: 49

Ala Ala Asp Pro Ser Arg Trp Tyr Phe Cys Ser Ser Asp Ser Asn Pro
1               5                   10                  15

Asn Thr Phe Asp Ser
            20


<210> SEQ ID NO 50
<211> LENGTH: 16
<212> TYPE: PRT
<213> ORGANISM: Lama glama

<400> SEQUENCE: 50

Ala Ala Ser Thr Gly Tyr Gly Thr Asn Ser Arg Tyr Asp Tyr Asp Tyr
1               5                   10                  15


<210> SEQ ID NO 51
<211> LENGTH: 139
<212> TYPE: PRT
<213> ORGANISM: Lama glama

<400> SEQUENCE: 51

Gln Val Gln Leu Val Glu Ser Gly Gly Gly Leu Val Gln Ala Gly Gly
1               5                   10                  15

Ser Lys Arg Leu Ser Cys Ala Ala Ser Gly Arg Pro Phe Ser Asn Ser
            20                  25                  30

Ala Met Gly Trp Phe Arg Gln Ala Pro Gly Lys Glu Arg Glu Phe Val
        35                  40                  45

Ala Ala Ile Ser Trp Ser Gly Gly Asn Thr Tyr Tyr Ala Asp Ser Val
    50                  55                  60

Lys Gly Arg Phe Thr Ile Ser Arg Asp Asn Ala Lys Asn Ala Val Tyr
65                  70                  75                  80

Leu Arg Met Asn Ser Leu Glu Pro Glu Asp Thr Ala Val Tyr Tyr Cys
                85                  90                  95

Ala Gly Asp Arg Gln Pro Tyr Val Tyr Asp Leu Pro Thr Ala Gln Tyr
            100                 105                 110

Gln Tyr Asp Tyr Trp Gly Gln Gly Thr Gln Val Thr Val Ser Ser Gly
        115                 120                 125

Ser Glu Gln Lys Leu Ile Ser Glu Glu Asp Leu
    130                 135


<210> SEQ ID NO 52
<211> LENGTH: 139
<212> TYPE: PRT
<213> ORGANISM: Lama glama

<400> SEQUENCE: 52

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
            20                  25                  30
```

```
Ala Met Gly Trp Phe Arg Gln Ala Pro Gly Lys Glu Arg Glu Phe Val
        35                  40                  45

Ala Ala Ile Ser Trp Ser Gly Gly Lys Thr Leu Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Thr Pro Ala Asp Leu Thr Val Val Ala Gly Pro Pro Arg Ile
            100                 105                 110

Glu Met Trp Tyr Trp Gly Gln Gly Thr Gln Val Thr Val Ser Ser Gly
        115                 120                 125

Ser Glu Gln Lys Leu Ile Ser Glu Glu Asp Leu
    130                 135
```

<210> SEQ ID NO 53
<211> LENGTH: 139
<212> TYPE: PRT
<213> ORGANISM: Lama glama

<400> SEQUENCE: 53

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
            20                  25                  30

Ala Met Gly Trp Phe Arg Gln Ala Pro Gly Lys Glu Arg Glu Phe Val
        35                  40                  45

Ala Ala Leu Thr Trp Ser Gly Gly Asn Thr Val Tyr Arg Asp Ser Val
    50                  55                  60

Lys Gly Arg Phe Ile Ile Thr Arg Asp Asn Ala Lys Asn Ala Val Tyr
65                  70                  75                  80

Leu Gln Met Asn Ser Leu Lys Pro Glu Asp Thr Ala Val Tyr Tyr Cys
                85                  90                  95

Ala Ser Asp Arg Arg Pro Tyr Arg Tyr Asn Ile Gly Thr Ala Glu Gly
            100                 105                 110

Glu Tyr Asn Tyr Trp Gly Gln Gly Thr Gln Val Thr Val Ser Ser Gly
        115                 120                 125

Ser Glu Gln Lys Leu Ile Ser Glu Glu Asp Leu
    130                 135
```

<210> SEQ ID NO 54
<211> LENGTH: 135
<212> TYPE: PRT
<213> ORGANISM: Lama glama

<400> SEQUENCE: 54

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
            20                  25                  30

Ala Met Gly Trp Phe Arg Gln Thr Pro Gly Lys Glu Arg Glu Phe Val
        35                  40                  45

Ala Ala Ile Thr Trp Ser Gly Gly Ala Thr Tyr Tyr Ala Asp Ser Val
    50                  55                  60

Lys Gly Arg Phe Ile Ile Ser Arg Asp Asn Thr Lys Asn Thr Val Tyr
65                  70                  75                  80
```

```
Leu Gln Met Asn Ser Leu Lys Pro Glu Asp Thr Ala Val Tyr Tyr Cys
                85                  90                  95

Ala Ala Asp Arg Lys Pro Tyr Ser Tyr Tyr Pro Ser Asp Phe Gly Ser
            100                 105                 110

Trp Gly Gln Gly Thr Gln Val Thr Val Ser Ser Gly Ser Glu Gln Lys
        115                 120                 125

Leu Ile Ser Glu Glu Asp Leu
    130                 135


<210> SEQ ID NO 55
<211> LENGTH: 138
<212> TYPE: PRT
<213> ORGANISM: Lama glama

<400> SEQUENCE: 55

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
            20                  25                  30

Ala Met Gly Trp Phe Arg Gln Ala Pro Gly Lys Glu Arg Glu Phe Val
        35                  40                  45

Ala His Ile Thr Trp Thr Gly Gly Ile Thr Tyr Tyr Ser Asp Ser Val
    50                  55                  60

Lys Gly Arg Phe Ile Ile Ser Arg Asp Asn Ala Lys Asn Thr Val Asn
65                  70                  75                  80

Leu Gln Met Asn Ser Leu Lys Ala Glu Asp Thr Ala Val Tyr Tyr Cys
                85                  90                  95

Ala Ala Asp Arg Val Pro Tyr Arg Phe Gly Val Pro Ser Ile Asn Glu
            100                 105                 110

Tyr Asp Tyr Trp Gly Gln Gly Thr Gln Val Thr Val Ser Ser Gly Ser
        115                 120                 125

Glu Gln Lys Leu Ile Ser Glu Glu Asp Leu
    130                 135


<210> SEQ ID NO 56
<211> LENGTH: 137
<212> TYPE: PRT
<213> ORGANISM: Lama glama

<400> SEQUENCE: 56

Gln Val Gln Leu Val Glu Ser Gly Gly Gly Leu Val Gln Ala Gly Gly
1               5                   10                  15

Ser Leu Arg Leu Ser Cys Ala Ala Ser Thr Arg Thr Phe Ser Asn Tyr
            20                  25                  30

Val Met Gly Trp Phe Arg Gln Ala Pro Gly Lys Glu Arg Glu Phe Val
        35                  40                  45

Ser Ala Ile Thr Ser Ser Gly Arg Gly Thr Ser Tyr Ala Asp Ser Val
    50                  55                  60

Lys Gly Arg Phe Thr Ile Ser Arg Asp Asn Ala Lys Asn Thr Val Phe
65                  70                  75                  80

Leu Gln Met Asn Ser Leu Lys Pro Glu Asp Thr Ala Val Tyr Tyr Cys
                85                  90                  95

Ala Ala Thr Ala Ala Asp Tyr Val Leu Arg Ser Arg Pro Ser Val Tyr
            100                 105                 110

Ser Tyr Trp Gly Gln Gly Thr Gln Val Thr Val Ser Ser Gly Ser Glu
        115                 120                 125
```

```
Gln Lys Leu Ile Ser Glu Glu Asp Leu
    130                 135


<210> SEQ ID NO 57
<211> LENGTH: 135
<212> TYPE: PRT
<213> ORGANISM: Lama glama

<400> SEQUENCE: 57

Gln Val Gln Leu Val Glu Ser Gly Gly Gly Leu Val Gln Ala Gly Gly
1               5                   10                  15

Ser Leu Arg Leu Ser Cys Ala Ala Ser Ala Arg Thr Phe Ser Arg Tyr
            20                  25                  30

Gly Ala Gly Trp Phe Arg Gln Ala Pro Gly Lys Glu Arg Glu Phe Val
        35                  40                  45

Gly Ala Ile Thr Trp Gly Gly Gly Arg Thr Lys Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Lys Ser Glu Asp Thr Ala Val Tyr Tyr Cys
                85                  90                  95

Ala Ser Ser Ser Ile Glu Phe Gly Pro Leu Glu Asp Thr Tyr Asp Tyr
            100                 105                 110

Trp Gly Gln Gly Thr Gln Val Thr Val Ser Ser Gly Ser Glu Gln Lys
        115                 120                 125

Leu Ile Ser Glu Glu Asp Leu
    130                 135


<210> SEQ ID NO 58
<211> LENGTH: 138
<212> TYPE: PRT
<213> ORGANISM: Lama glama

<400> SEQUENCE: 58

Gln Val Gln Leu Val Glu Ser Gly Gly Gly Leu Val Gln Ala Gly Asp
1               5                   10                  15

Ser Leu Arg Leu Ser Cys Thr Ala Ser Glu Arg Ala Phe Ser Arg Tyr
            20                  25                  30

Ala Met Gly Trp Phe Arg Gln Ala Pro Gly Lys Glu Arg Glu Leu Val
        35                  40                  45

Ala Ala Val Ser Trp Ala Gly Gly Thr Thr Tyr Tyr Gly Asp Ser Val
    50                  55                  60

Lys Gly Arg Phe Thr Ile Ser Arg Asp Asn Ala Lys Ile Thr Val Tyr
65                  70                  75                  80

Leu Gln Met Asn Ser Leu Lys Pro Glu Asp Thr Ala Val Tyr Tyr Cys
                85                  90                  95

Ala Ala Glu Ala Arg Glu Phe Ser Val Gly Ser Tyr Tyr Ala Thr Glu
            100                 105                 110

Tyr Asp Tyr Trp Gly Gln Gly Thr Gln Val Thr Val Ser Ser Gly Ser
        115                 120                 125

Glu Gln Lys Leu Ile Ser Glu Glu Asp Leu
    130                 135


<210> SEQ ID NO 59
<211> LENGTH: 135
<212> TYPE: PRT
<213> ORGANISM: Lama glama
```

<400> SEQUENCE: 59

```
Gln Val Gln Leu Val Glu Ser Gly Gly Gly Arg Val Gln Ala Gly Asp
1               5                   10                  15

Ser Leu Arg Leu Ser Cys Ala Ala Ser Gly Arg Thr Phe Ser Pro Tyr
            20                  25                  30

Ala Met Gly Trp Phe Arg Gln Ala Pro Gly Lys Glu Arg Glu Phe Val
        35                  40                  45

Ala Thr Ile Asn Trp Ser Gly Asp Tyr Thr Tyr Tyr Thr Asp Ser Val
    50                  55                  60

Lys Gly Arg Phe Thr Thr Ser Arg Asp Asn Ala Lys Asn Thr Leu Tyr
65                  70                  75                  80

Leu Glu Met Asn Ser Leu Asn Ala Glu Asp Thr Ala Val Tyr Tyr Cys
                85                  90                  95

Val Ala Arg Val Gly Ser Pro Ser Ser Ser Asp Arg Ala Tyr Gln Tyr
            100                 105                 110

Trp Gly Gln Gly Thr Gln Val Thr Val Ser Ser Gly Ser Glu Gln Lys
        115                 120                 125

Leu Ile Ser Glu Glu Asp Leu
    130                 135
```

<210> SEQ ID NO 60
<211> LENGTH: 138
<212> TYPE: PRT
<213> ORGANISM: Lama glama

<400> SEQUENCE: 60

```
Gln Val Gln Leu Val Glu Ser Gly Gly Gly Leu Val Gln Asp Gly Gly
1               5                   10                  15

Ser Leu Arg Leu Ser Cys Thr Ala Ser Gly Arg Thr Phe Ser Asn Asn
            20                  25                  30

Ala Met Gly Trp Phe Arg Gln Glu Pro Gly Arg Glu Arg Glu Phe Val
        35                  40                  45

Ala Ala Ile Arg Trp Asn Gly Ile Ala Asn Tyr Ala Asp Ser Val Lys
    50                  55                  60

Gly Arg Phe Thr Ile Ser Gly Asp Asn Ala Lys Asn Thr Val Tyr Leu
65                  70                  75                  80

Gln Met Asn Ser Leu Lys Pro Asp Asp Thr Ala Val Tyr Tyr Cys Ala
                85                  90                  95

Ala Ala Ile Arg Asp Gly His Asn Tyr Tyr Ala Ser Asp Met Arg Arg
            100                 105                 110

Tyr Asp Tyr Trp Gly Gln Gly Thr Gln Val Thr Val Ser Ser Gly Ser
        115                 120                 125

Glu Gln Lys Leu Ile Ser Glu Glu Asp Leu
    130                 135
```

<210> SEQ ID NO 61
<211> LENGTH: 137
<212> TYPE: PRT
<213> ORGANISM: Lama glama

<400> SEQUENCE: 61

```
Gln Leu Gln Leu Val Glu Ser Gly Gly Gly Leu Val Gln Ala Gly Gly
1               5                   10                  15

Ser Leu Arg Leu Ser Cys Ala Ala Ser Gly Asp Thr Phe Ser Arg Tyr
            20                  25                  30
```

```
Val Met Gly Trp Phe Arg Gln Ala Pro Gly Lys Glu Arg Thr Phe Val
        35                  40                  45

Val Gly Ile Ser Gly Gly Gly Gly Ile Thr Arg Tyr Ala Asp Ser Val
    50                  55                  60

Lys Gly Arg Phe Thr Ile Ser Arg Asp Asn Ala Glu Asn Thr Leu Tyr
65                  70                  75                  80

Leu Glu Met Asn Thr Leu Asn Pro Glu Asp Thr Ala Val Tyr Tyr Cys
            85                  90                  95

Ala Ala Thr Pro Ala Asp Ser Ala Phe Met Arg Asn Leu Arg Val Tyr
            100                 105                 110

Asp Tyr Trp Gly Gln Gly Thr Gln Val Thr Val Ser Ser Gly Ser Glu
        115                 120                 125

Gln Lys Leu Ile Ser Glu Glu Asp Leu
    130                 135


<210> SEQ ID NO 62
<211> LENGTH: 138
<212> TYPE: PRT
<213> ORGANISM: Lama glama

<400> SEQUENCE: 62

Gln Val Gln Leu Val Glu Ser Gly Gly Gly Leu Val Gln Ala Gly Gly
1               5                   10                  15

Ser Leu Arg Leu Ser Cys Glu Ala Ser Gly Arg Thr Ser Ser Ser Tyr
            20                  25                  30

Val Met Gly Trp Phe Arg Arg Val Ser Gly Lys Glu Arg Glu Phe Val
        35                  40                  45

Ala Ala Ile Asn Pro Thr Gly Ser Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Val Gln Met Asn Gly Leu Lys Pro Glu Asp Thr Ala Val Tyr Tyr Cys
            85                  90                  95

Ala Ala Thr Arg Arg Asp Phe Tyr Ile Ile Arg Asn Ser Arg Pro Gln
            100                 105                 110

Phe Asp Tyr Trp Gly Gln Gly Thr Gln Val Thr Val Ser Ser Gly Ser
        115                 120                 125

Glu Gln Lys Leu Ile Ser Glu Glu Asp Leu
    130                 135


<210> SEQ ID NO 63
<211> LENGTH: 133
<212> TYPE: PRT
<213> ORGANISM: Lama glama

<400> SEQUENCE: 63

Gln Val Gln Leu Val Glu Ser Glu Gly Gly Leu Val Gln Pro Gly Gly
1               5                   10                  15

Ser Leu Arg Leu Ser Cys Ala Ala Ser Gly Phe Thr Phe Lys Tyr Tyr
            20                  25                  30

Tyr Met Asn Trp Val Arg Gln Ala Pro Gly Lys Gly Leu Glu Trp Val
        35                  40                  45

Ser Arg Ile Asn Gln Leu Gly Gly Thr Ser Tyr Gly Asp Ser Val Lys
    50                  55                  60

Gly Arg Phe Thr Ile Ser Arg Asp Asn Ala Lys Asn Thr Leu Tyr Leu
65                  70                  75                  80
```

```
Gln Met Asn Ser Leu Val Pro Glu Asp Thr Ala Val Tyr Tyr Cys Ala
                85                  90                  95

Arg Cys Pro Ala Gly Ala Ala Cys Lys Val Glu Tyr Asp Tyr Arg Gly
            100                 105                 110

Gln Gly Thr Gln Val Thr Val Ser Ser Gly Ser Glu Gln Lys Leu Ile
        115                 120                 125

Ser Glu Glu Asp Leu
    130


<210> SEQ ID NO 64
<211> LENGTH: 131
<212> TYPE: PRT
<213> ORGANISM: Lama glama

<400> SEQUENCE: 64

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Phe
            20                  25                  30

Val Met Asn Trp Ala Arg Gln Ala Pro Gly Lys Gly Leu Glu Trp Val
        35                  40                  45

Ser Thr Ile Asn Ser Asp Gly Asp Val Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Gly Lys Gly Trp Phe Leu Asn Arg Arg Asp Glu Ser Arg Gly Gln Gly
            100                 105                 110

Thr Gln Val Thr Val Ser Ser Gly Ser Glu Gln Lys Leu Ile Ser Glu
        115                 120                 125

Glu Asp Leu
    130


<210> SEQ ID NO 65
<211> LENGTH: 128
<212> TYPE: PRT
<213> ORGANISM: Lama glama

<400> SEQUENCE: 65

Gln Val Gln Leu Val Glu Ser Gly Gly Asp Leu Val Gln Ala Gly Gly
1               5                   10                  15

Ser Leu Arg Leu Ser Cys Ala Ala Ser Gly Gly Ile Phe Ile Ile Asn
            20                  25                  30

Asn Met Gly Trp Tyr Arg Gln Thr Pro Gly Asn Gln Arg Glu Leu Val
        35                  40                  45

Ala Glu Ile Thr Arg Ala Gly Asn Ser Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Arg Leu Lys Pro Glu Asp Thr Ala Val Tyr Tyr Cys Asn
                85                  90                  95

Phe Asn Val Arg Tyr Tyr Gly Glu Tyr Trp Gly Gln Gly Thr Gln Val
            100                 105                 110

Thr Val Ser Ser Gly Ser Glu Gln Lys Leu Ile Ser Glu Glu Asp Leu
        115                 120                 125
```

<210> SEQ ID NO 66
<211> LENGTH: 128
<212> TYPE: PRT
<213> ORGANISM: Lama glama

<400> SEQUENCE: 66

```
Gln Val Gln Leu Val Glu Ser Gly Gly Gly Leu Val Gln Pro Gly Gly
1               5                   10                  15

Ser Leu Arg Leu Ser Cys Ala Ala Ser Thr Asn Ile Phe Asn Leu Arg
            20                  25                  30

Ser Met Gly Trp Tyr Arg Gln Ala Pro Gly Lys Glu Arg Glu Leu Val
        35                  40                  45

Ala Thr Ile Thr Thr Tyr Asn Thr Asn Tyr Ala Asp Ser Val Lys Gly
    50                  55                  60

Arg Phe Thr Ile Ser Arg Asp Asn Ala Lys Lys Thr Met Tyr Leu Gln
65                  70                  75                  80

Met Asn Ser Leu Arg Pro Glu Asp Thr Ala Val Tyr Tyr Cys Asn Leu
                85                  90                  95

Gln Asn Arg Tyr Asp Ala Met Asp Tyr Trp Gly Lys Gly Thr Gln Val
            100                 105                 110

Thr Val Ser Ser Gly Ser Glu Gln Lys Leu Ile Ser Glu Glu Asp Leu
        115                 120                 125
```

<210> SEQ ID NO 67
<211> LENGTH: 129
<212> TYPE: PRT
<213> ORGANISM: Lama glama

<400> SEQUENCE: 67

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Asn Ala Arg Val Met Ser
            20                  25                  30

Thr Met Gly Trp Tyr Arg Gln Pro Pro Gly Lys Gln Arg Glu Leu Val
        35                  40                  45

Ala Thr Met Ser Tyr Gly Gly Thr Thr Asn Tyr Ala Asp Ser Val Lys
    50                  55                  60

Gly Arg Phe Thr Ile Ser Arg Asp Asn Ala Lys Asn Ile Val Thr Leu
65                  70                  75                  80

Gln Met Asn Ser Leu Lys Pro Glu Asp Thr Ala Val Tyr Tyr Cys Asn
                85                  90                  95

Ala Glu Pro Arg Tyr Tyr Gly Ala Ala Tyr Trp Gly Lys Gly Thr Gln
            100                 105                 110

Val Thr Val Ser Ser Gly Ser Glu Gln Lys Leu Ile Ser Glu Glu Asp
        115                 120                 125

Leu
```

<210> SEQ ID NO 68
<211> LENGTH: 126
<212> TYPE: PRT
<213> ORGANISM: Lama glama

<400> SEQUENCE: 68

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Ile Ile Phe Arg Ser Asn
            20                  25                  30
```

```
Gly Met Ala Trp Tyr Arg Gln Ala Pro Gly Lys Glu Arg Glu Trp Val
        35                  40                  45

Gly Ser Ile Thr Ser Phe Gly Asp Thr Ile Tyr Arg Asp Ser Val Lys
    50                  55                  60

Gly Arg Phe Thr Ile Ser Arg Asp Asn Ala Arg Asn Ala Val Ser Leu
65                  70                  75                  80

Gln Met Asn Ser Leu Lys Thr Glu Asp Thr Ala Val Tyr Tyr Cys Asn
                85                  90                  95

Thr Tyr Pro Val Asn Ser Tyr Trp Gly Gln Gly Thr Gln Val Thr Val
            100                 105                 110

Ser Ser Gly Ser Glu Gln Lys Leu Ile Ser Glu Glu Asp Leu
        115                 120                 125


<210> SEQ ID NO 69
<211> LENGTH: 136
<212> TYPE: PRT
<213> ORGANISM: Lama glama

<400> SEQUENCE: 69

Gln Val Gln Leu Val Glu Ser Gly Gly Gly Leu Val Gln Ala Gly Asp
1               5                   10                  15

Ser Leu Arg Leu Ser Cys Ala Ala Ser Gly Leu Ile Val Ser Asn Tyr
            20                  25                  30

Ala Met Gly Trp Phe Arg Gln Ala Pro Gly Lys Glu Arg Glu Phe Val
        35                  40                  45

Ala Tyr Ile Asn Trp Asn Gly Gly Val Thr Tyr Tyr Thr Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Arg Thr Ser Arg Ala Ser Val Thr Thr Arg Val Ala Asp Phe Gly
            100                 105                 110

Tyr Trp Gly Gln Gly Thr Gln Val Thr Val Ser Ser Gly Ser Glu Gln
        115                 120                 125

Lys Leu Ile Ser Glu Glu Asp Leu
    130                 135


<210> SEQ ID NO 70
<211> LENGTH: 138
<212> TYPE: PRT
<213> ORGANISM: Lama glama

<400> SEQUENCE: 70

Gln Val Gln Leu Val Glu Ser Gly Gly Gly Leu Val Gln Ala Gly Gly
1               5                   10                  15

Ser Leu Arg Leu Ser Cys Val Ala Ser Gly Leu Thr Leu Thr Asn Tyr
            20                  25                  30

Val Met Gly Trp Phe Arg Gln Ala Pro Gly Lys Glu Arg Glu Phe Val
        35                  40                  45

Ala Ala Ile Ser Arg Ser Gly Ser Gly Thr Asp Tyr Val Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95
```

```
Gly Ala Asp Ser Ala Gly Trp Phe Arg Ile Arg Gln Val Pro Ala Asp
            100                 105                 110

Tyr Asp Tyr Trp Gly Gln Gly Thr Gln Val Thr Val Ser Ser Gly Ser
        115                 120                 125

Glu Gln Lys Leu Ile Ser Glu Glu Asp Leu
    130                 135
```

<210> SEQ ID NO 71
<211> LENGTH: 136
<212> TYPE: PRT
<213> ORGANISM: Lama glama

<400> SEQUENCE: 71

```
Gln Val Gln Leu Val Glu Ser Gly Gly Gly Leu Val Gln Ala Gly Gly
1               5                   10                  15

Ser Leu Arg Leu Ser Val Ala Ala Ser Gly Arg Ser Phe Asp Ile His
            20                  25                  30

Ala Met Gly Trp Phe Arg Gln Ala Pro Gly Lys Glu Arg Glu Phe Val
        35                  40                  45

Ala Ala Ile Ser Trp Asn Ser Gly Asn Thr Glu Tyr Ala Asp Val Val
    50                  55                  60

Lys Gly Arg Phe Thr Ile Ser Arg Asp Asn Ala Lys Asp Thr Val Tyr
65                  70                  75                  80

Leu Gln Met Asn Gly Leu Lys Pro Glu Asp Thr Ala Val Tyr Tyr Cys
                85                  90                  95

Ala Arg Gly Ala Phe Ser Phe Ala Thr Thr Val Gln Ser Asp Tyr Asn
            100                 105                 110

Tyr Trp Gly Gln Gly Thr Gln Val Thr Val Ser Ser Gly Ser Glu Gln
        115                 120                 125

Lys Leu Ile Ser Glu Glu Asp Leu
    130                 135
```

<210> SEQ ID NO 72
<211> LENGTH: 132
<212> TYPE: PRT
<213> ORGANISM: Lama glama

<400> SEQUENCE: 72

```
Gln Val Gln Leu Val Glu Ser Gly Gly Gly Leu Val Gln Pro Gly Gly
1               5                   10                  15

Ser Leu Arg Leu Ser Cys Thr Ala Ser Glu Gly Thr Phe Ser Val Tyr
            20                  25                  30

Asn Leu Ala Trp Phe Arg Gln Ala Pro Gly Lys Glu Arg Glu Leu Val
        35                  40                  45

Ala Ser Ile Asn Trp Ser Gly Ser Val Thr Tyr Tyr Thr Asp Ser Val
    50                  55                  60

Lys Gly Arg Phe Thr Val Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ala Leu Arg Pro Asn Ser Val Gln Tyr Lys Tyr Trp Gly Gln
            100                 105                 110

Gly Thr Gln Val Thr Val Ser Ser Gly Ser Glu Gln Lys Leu Ile Ser
        115                 120                 125

Glu Glu Asp Leu
    130
```

<210> SEQ ID NO 73
<211> LENGTH: 137
<212> TYPE: PRT
<213> ORGANISM: Lama glama

<400> SEQUENCE: 73

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
            20                  25                  30

Arg Met Gly Trp Phe Arg Gln Pro Pro Gly Lys Glu Arg Glu Phe Val
        35                  40                  45

Ala Arg Ile Ser Pro Asn Gly Gly Ser Thr Tyr Tyr Thr Asp Ser Met
    50                  55                  60

Arg Gly Arg Phe Ile Ile Ser Arg Asp Asn Val Lys Asn Thr Val Tyr
65                  70                  75                  80

Leu Gln Met Asn Ser Leu Lys His Glu Asp Thr Ala Val Tyr Tyr Cys
                85                  90                  95

Ala Ala Thr Pro Gly Tyr Thr Ser Ala Ser Lys Val Pro Ser Asp Tyr
            100                 105                 110

Ala Tyr Trp Gly Gln Gly Thr Gln Val Thr Val Ser Ser Gly Ser Glu
        115                 120                 125

Gln Lys Leu Ile Ser Glu Glu Asp Leu
    130                 135
```

<210> SEQ ID NO 74
<211> LENGTH: 136
<212> TYPE: PRT
<213> ORGANISM: Lama glama

<400> SEQUENCE: 74

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Asp
            20                  25                  30

Tyr Met Ala Trp Ile Arg Gln Pro Pro Gly Lys Glu Ser Glu Phe Val
        35                  40                  45

Ala Val Ile Ala Arg Ser Asn Ala Gly Thr Phe Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Asn Arg Glu Asp Thr Ala Val Tyr Tyr Cys
                85                  90                  95

Thr Ala Asp His Ala Leu Arg Leu Ser Ser Arg Leu Thr Asp Tyr Asp
            100                 105                 110

Tyr Trp Gly Gln Gly Thr Gln Val Thr Val Ser Ser Gly Ser Glu Gln
        115                 120                 125

Lys Leu Ile Ser Glu Glu Asp Leu
    130                 135
```

<210> SEQ ID NO 75
<211> LENGTH: 140
<212> TYPE: PRT
<213> ORGANISM: Lama glama

<400> SEQUENCE: 75

```
Gln Val Gln Leu Val Glu Ser Gly Gly Gly Val Val Gln Ala Gly Gly
1               5                   10                  15

Ser Leu Arg Leu Ser Cys Ala Ala Ser Gly Arg Thr Leu Gly Ser Tyr
            20                  25                  30

Asp Val Gly Trp Phe Arg Gln Ala Pro Gly Lys Glu Arg Glu Phe Leu
        35                  40                  45

Ser Ile Ser Arg Gln Ser Gly Ala Ser Ile Tyr Cys Ala Asp Ser Val
    50                  55                  60

Lys Gly Arg Phe Thr Val Ser Arg Asp Asn Ala Lys Asn Leu Val Tyr
65                  70                  75                  80

Leu Gln Met Asn Ser Leu Lys Pro Glu Asp Thr Ala Val Tyr Tyr Cys
                85                  90                  95

Ala Ala Asp Pro Ser Arg Trp Tyr Phe Cys Ser Ser Asp Ser Asn Pro
            100                 105                 110

Asn Thr Phe Asp Ser Trp Gly Gln Gly Thr Gln Val Thr Val Ser Ser
        115                 120                 125

Gly Ser Glu Gln Lys Leu Ile Ser Glu Glu Asp Leu
    130                 135                 140
```

<210> SEQ ID NO 76
<211> LENGTH: 136
<212> TYPE: PRT
<213> ORGANISM: Lama glama

<400> SEQUENCE: 76

```
Gln Val Gln Leu Val Glu Ser Gly Gly Gly Leu Ala Gln Ala Gly Ala
1               5                   10                  15

Ser Leu Arg Leu Ser Cys Val Ala Ser Gly Arg Thr Phe Glu Ser Tyr
            20                  25                  30

Pro Met Gly Trp Phe Arg Gln Ala Pro Gly Lys Glu Arg Glu Phe Val
        35                  40                  45

Gly Ala Ile Ser Trp Asn Gly Gly Val Ile Asp Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Asn Leu Lys Pro Glu Asp Thr Ala Ile Tyr Tyr Cys
                85                  90                  95

Ala Thr Lys Thr Arg Gly Gly Asp Trp Arg Ser Gly Lys Asn Trp Asn
            100                 105                 110

Tyr Trp Gly Gln Gly Thr Gln Val Thr Val Ser Ser Gly Ser Glu Gln
        115                 120                 125

Lys Leu Ile Ser Glu Glu Asp Leu
    130                 135
```

<210> SEQ ID NO 77
<211> LENGTH: 139
<212> TYPE: PRT
<213> ORGANISM: Lama glama

<400> SEQUENCE: 77

```
Gln Val Gln Leu Val Glu Ser Gly Gly Gly Leu Val Gln Ala Gly Gly
1               5                   10                  15

Ser Leu Arg Leu Ser Cys Ala Ala Ser Gly His Ala Ser Ser Thr Tyr
            20                  25                  30

Thr Met Gly Trp Phe Arg Gln Ala Pro Gly Lys Glu Arg Glu Phe Val
        35                  40                  45
```

```
Ser Gly Ile Asn Trp Ser Asp Asp Ser Thr Ser Tyr Ala Glu Ser Val
    50                  55                  60

Lys Gly Arg Phe Thr Ile Ser Arg Asp Gly Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Leu Gln Tyr Gly Trp Arg Trp Ser Trp Asp Asp Gly Ser Ala Arg
            100                 105                 110

Asp Met Arg Tyr Trp Gly Lys Gly Thr Gln Val Thr Val Ser Ser Gly
        115                 120                 125

Ser Glu Gln Lys Leu Ile Ser Glu Glu Asp Leu
    130                 135


<210> SEQ ID NO 78
<211> LENGTH: 134
<212> TYPE: PRT
<213> ORGANISM: Lama glama

<400> SEQUENCE: 78

Gln Val Gln Leu Val Glu Ser Gly Gly Gly Leu Val Gln Ala Gly Gly
1               5                   10                  15

Ser Leu Arg Leu Ser Cys Ala Ala Ala Gly Arg Thr Phe Ser Thr Tyr
            20                  25                  30

Ala Arg Gly Trp Phe Arg Gln Ala Pro Gly Lys Glu Arg Glu Phe Val
        35                  40                  45

Ala Ile Leu Thr Arg Gly Ser Asp Ala Tyr Tyr Ala Asp Ser Val Arg
    50                  55                  60

Gly Arg Phe Thr Ile Ser Arg Asp Ser Ala Thr Asn Thr Val Tyr Leu
65                  70                  75                  80

Gln Met Thr Ser Leu Lys Pro Glu Asp Thr Ala Val Tyr Tyr Cys Ala
                85                  90                  95

Ala Ser Thr Gly Tyr Gly Thr Asn Ser Arg Tyr Asp Tyr Asp Tyr Trp
            100                 105                 110

Gly Gln Gly Thr Gln Val Thr Val Ser Ser Arg Ser Glu Gln Lys Leu
        115                 120                 125

Ile Ser Glu Glu Asp Leu
    130


<210> SEQ ID NO 79
<211> LENGTH: 34
<212> TYPE: DNA
<213> ORGANISM: Artificial Sequence
<220> FEATURE:
<223> OTHER INFORMATION: Primer

<400> SEQUENCE: 79

accaaggtca tgaatgacta tgcacgtaaa acag                              34


<210> SEQ ID NO 80
<211> LENGTH: 34
<212> TYPE: DNA
<213> ORGANISM: Artificial Sequence
<220> FEATURE:
<223> OTHER INFORMATION: Primer

<400> SEQUENCE: 80

ctgttttacg tgcatagtca ttcatgacct tggt                              34


<210> SEQ ID NO 81
```

-continued

```
<211> LENGTH: 34
<212> TYPE: DNA
<213> ORGANISM: Artificial Sequence
<220> FEATURE:
<223> OTHER INFORMATION: Primer

<400> SEQUENCE: 81

accaaggtca tgaatgacta tgcacgtaaa acag                                34
```